US010479824B2

(12) United States Patent
Lawson et al.

(10) Patent No.: US 10,479,824 B2
(45) Date of Patent: Nov. 19, 2019

(54) SINGLE CHAIN FC POLYPEPTIDES

(75) Inventors: Alastair David Griffiths Lawson, Berkshire (GB); Paul Edward Stephens, Berkshire (GB)

(73) Assignee: UCB BIOPHARMA SPRL, Brussels (BE)

( * ) Notice: Subject to any disclaimer, the term of this patent is extended or adjusted under 35 U.S.C. 154(b) by 1110 days.

(21) Appl. No.: 12/374,213

(22) PCT Filed: Jul. 24, 2007

(86) PCT No.: PCT/GB2007/002842
§ 371 (c)(1),
(2), (4) Date: Jul. 13, 2009

(87) PCT Pub. No.: WO2008/012543
PCT Pub. Date: Jan. 31, 2008

(65) Prior Publication Data
US 2009/0304696 A1    Dec. 10, 2009

(30) Foreign Application Priority Data

Jul. 25, 2006  (GB) .................................. 0614780.5

(51) Int. Cl.
*C07K 16/00*  (2006.01)

(52) U.S. Cl.
CPC .................................. *C07K 16/00* (2013.01)

(58) Field of Classification Search
None
See application file for complete search history.

(56) References Cited

U.S. PATENT DOCUMENTS

| | | | |
|---|---|---|---|
| 6,165,745 A | 12/2000 | Ward et al. | |
| 6,534,036 B1 * | 3/2003 | Collinge | A61K 49/0058 424/184.1 |
| 7,666,622 B2 * | 2/2010 | Sharma et al. | 435/69.1 |
| 2003/0176352 A1 * | 9/2003 | Min et al. | 514/14 |
| 2003/0215427 A1 * | 11/2003 | Jensen | 424/93.21 |
| 2004/0033561 A1 * | 2/2004 | O'Keefe | C07H 21/04 435/69.1 |
| 2004/0062763 A1 * | 4/2004 | Mosser | C07K 16/1203 424/131.1 |
| 2005/0106222 A1 * | 5/2005 | Ailor et al. | 424/443 |
| 2005/0227324 A1 * | 10/2005 | Huang | C07K 16/283 435/69.1 |
| 2008/0260738 A1 * | 10/2008 | Moore et al. | 424/134.1 |
| 2009/0252729 A1 * | 10/2009 | Farrington et al. | 424/135.1 |
| 2009/0281028 A1 * | 11/2009 | Sullivan et al. | 514/12 |
| 2009/0291885 A1 * | 11/2009 | Sullivan et al. | 514/12 |
| 2009/0299044 A1 * | 12/2009 | Sullivan et al. | 536/23.53 |
| 2009/0305399 A1 * | 12/2009 | Sullivan et al. | 435/325 |
| 2009/0318341 A1 * | 12/2009 | Sullivan et al. | 514/12 |

FOREIGN PATENT DOCUMENTS

| | | |
|---|---|---|
| WO | WO2005001025 | 1/2005 |
| WO | WO2005077981 | 8/2005 |

OTHER PUBLICATIONS

Timmermann et al (FEBS Letters, 468:120-124, 2000).*
Greenwood et al (Ther. Imm., 1:247-255, 1994).*
Pluckthun et al (FEBS Letters, 462:307-312, 1999).*
Mariuzza et al. (Annu. Rev. Biophys. Biophys. Chem., 16: 139-159, 1987).*
Gussow et al (Methods in Enzymology, 203: 99-121, 1991).*
Casset et al (Biochemical and Biophysical Research Communications, 307:198-205, 2003).*
Greenwood, J. et al., Engineering Multiple-Domain Forms of the Therapeutic Antibody CAMPATH-IH: Effects on Complement Lysis, Therapeutic Immunology, 1994, pp. 247-255, vol. 1, London.
Dumont, Jennifer et al., Monomeric Fc Fusions: Impact on Pharmacokinetic and Biological Activity of Protein Therapeutics, Biodrugs, 2006, pp. 151-160, vol. 20.
Bitonti, Alan J. et al., Pulmonary Delivery of an Erythropoietin Fc Fusion Protein in Non-Human Primates Through an Immunoglobulin Transport Pathway, Proceedings of the National Academy of Sciences of USA, Jun. 29, 2004, pp. 9763-9768, vol. 101, No. 26, Washington D.C.
Low, S.C. et al., Oral and Pulmonary Delivery of FSH-Fc Fusion Proteins Via Neonatal Fc Receptor-Mediated Transcytosis, Human Reproduction, Jul. 2005, pp. 1805-1813, vol. 20.
International Search Report dated Oct. 19, 2007.
"Antibody"—"Isotypes," (visited Sep. 11, 2015) <https://en.wikipedia.org/wiki/Antibody> p. 1-20.
https://en.wikipedia.org/wiki/Immunoglobulin_G (last visited Sep. 15, 2015): "Immunoglobulin G (IgG) is a type of antibody. It is a protein complex composed of four peptide chains—two identical heavy chains and two identical light chains arranged in a Y-shape typical of antibody monomers", p. 1-4.

* cited by examiner

*Primary Examiner* — Brad Duffy
(74) *Attorney, Agent, or Firm* — McDonnell Boehnen Hulbert & Berghoff LLP

(57) ABSTRACT

The present invention relates to single chain polypeptides comprising one or more immunoglobulin Fc domains. In particular the present invention relates to single-chain Fc polypeptides in which at least one functional Fc domain is formed within the polypeptide chain.

9 Claims, 11 Drawing Sheets

Figure 1:
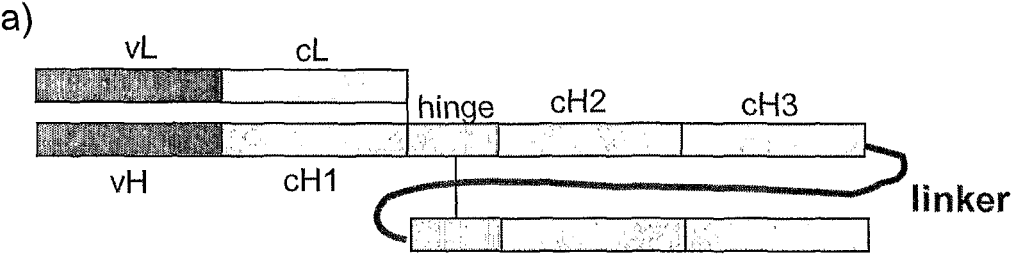
Figure 1:
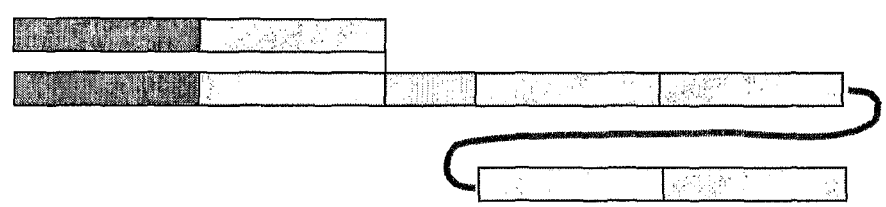
Figure 1:
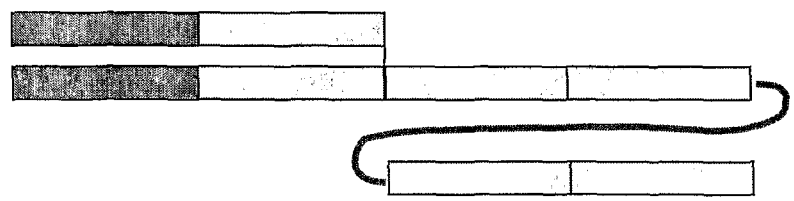

Specification includes a Sequence Listing.

a)

b)

c)

a)

b)

c)

a)

b)

c)

Figure 6 a)

*EPKSCDKTHTCPPCPA*PELLGGPSVFLFPPKPKDTLMISRTPEVTCVVVDVSHEDPEVKFNWYVDGVEVHNAKTKPREEQYNSTYRVVSVLTVLHQDWLNGKEYKC
KVSNKALPAPIEKTISKAKGQPREPQVYTLPPSRDELTKNQVSLTCLVKGFYPSDIAVEWESNGQPENNYKTTPPVLDSGSFFLYSKLTVDKSRWQQGNVFSCSV
MHEALHNHYTQKSLSLSPGKGGSSTASGSGSGGSTAGSSGGASSGGSTGSGTGGASSGGASGASG*EPKSCDKTHTCPPCPA*PELLGGPSVFL
FPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVLDSGSFFLYSKLTVDKSRWQQGNVFSCSVMHEALHNHYTQKSLSLSPGK b)

*EPKSSDKTHTSPPS*PAPELLGGPSVFLFPPKPKDTLMISRTPEVTCVVVDVSHEDPEVKFNWYVDGVEVHNAKTKPREEQYNSTYRVVSVLTVLHQDWLNGKEYKC
KVSNKALPAPIEKTISKAKGQPREPQVYTLPPSRDELTKNQVSLTCLVKGFYPSDIAVEWESNGQPENNYKTTPPVLDSGSFFLYSKLTVDKSRWQQGNVFSCSV
MHEALHNHYTQKSLSLSPGKGGSSTAGSSGSGGSTAGSSGGASSGGSTGSGTGGASSGGASGAPELLGGPSVFLFPPKPKDTLMISRTP
EVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSGSFFLYSKLTVDKSRWQQGNVFSCSVMHEALHNHYTQKSLSLSPGK c)

APELLGGPSVFLFPPKPKDTLMISRTPEVTCVVVDVSHEDPEVKFNWYVDGVEVHNAKTKPREEQYNSTYRVVSVLTVLHQDWLNGKEYKCCKVSNKALPAPIEKTI
SKAKGQPREPQVYTLPPSRDELTKNQVSLTCLVKGFYPSDIAVEWESNGQPENNYKTTPPVLDSGSFFLYSKLTVDKSRWQQGNVFSCSVMHEALHNHYTQKSLS
LSPGKGGSSTASGSGSGGSTAGSSGGAGSSGGSTTAGGSASGSGSTGSGTGGASSGGASGASGAPELLGGPSVFLFPPKPKDTLMISRTPEVTCVVVDVSHEDPE
VKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIA
VEWESNGQPENNYKTTPPVLDSGSFFLYSKLTVDKSRWQQGNVFSCSVMHEALHNHYTQKSLSLSPGK

Figure 6, Continuation d)

*EPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKC*
KVSNKALPAPIEKTISKAKGGGSGGGGSGGGGS*EPKSCDKTHTCPPCPAPELLGGPSVFLFPPKPKDTLMISRTPEVTCVVVDVSHEDPEVKFNW*
*YVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWES*
NGQPENNYKTTPPVLDSDGSFFLYSKLTVDKSRWQQGNVFSCSVMHEALHNHYTQKSLSLSPGKGGGGSGGGGSGGGGSGQPREPQVYTLPPSRDE
LTKNQVSLTCLVKGFYPSDIAVEWESNGQPENNYKTTPPVLDSDGSFFLYSKLTVDKSRWQQGNVFSCSVMHEALHNHYTQKSLSLSPGK e)

*EPKSSDKTHTSPPSPAPELLGGPSVFLFPPKPKDTLMISRTPEVTCVVVDVSHEDPEVKFNWYVDGVEVHNAKTKPREEQYNSTYRVVSVLTVLHQDWLNGKEYKC*
KVSNKALPAPIEKTISKAKGGGSGGGGSGGGGSAPELLGGPSVFLFPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGKGGGGSGGGGSGGGGSGQPREPQVYTLPPSRDELTKNQVSLTCLVKGF
YPSDIAVEWESNGQPENNYKTTPPVLDSDGSFFLYSKLTVDKSRWQQGNVFSCSVMHEALHNHYTQKSLSLSPGK f)

APELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTI
SKAKGGGGSGGGGSGGGGSAPELLGGPSVFLFPPKPKDTLMISRTPEVTCVVVDVSHEDPEVKFNWYVDGVEVHNAKTKPREEQYNSTYRVVSVLT
VLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVD
KSRWQQGNVFSCSVMHEALHNHYTQKSLSLSPGKGGGGSGGGGSGGGGSGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNHYTQKSLSLSPGK

SINGLE CHAIN FC POLYPEPTIDES

This is a National Stage of International Application No. PCT/ GB07/02842, filed Jul. 24, 2007.

The present invention relates to single chain polypeptides comprising one or more immunoglobulin Fc domains. In particular the present invention relates to single-chain polypeptides in which at least one functional Fc domain is formed within the chain.

Immunoglobulins are bivalent Y-shaped molecules comprising two identical heavy chains and two identical light chains. Disulfide bonds link together the heavy and light chain pairs as well as the two heavy chains. Each chain consists of one variable domain that varies in sequence and is responsible for antigen binding, these are known as the $V_H$ and $V_L$ domains for the heavy and light chains respectively. Each chain also consists of at least one constant domain. In the light chain there is a single constant domain ($C_L$) and in the heavy chain there are at least three ($C_H1$, $C_H2$ and $C_H3$), sometimes four ($C_H4$) depending on the isotype. In humans there are five different classes or isotypes of antibodies including IgA (which includes IgA1 and IgA2), IgD, IgE, IgG (which includes subclasses IgG1, IgG2, IgG3 and IgG4) and IgM.

The Fc domain of an antibody typically comprises at least the last two heavy chain constant region domains of each chain which dimerise to form the Fc domain. The Fc domain is responsible for providing antibody effector functions, including determining antibody half-life and distribution throughout the body, ability to fix complement and binding to cell surface Fc receptors. The properties of Fc domains have made them useful therapeutic agents and Fc domains have been fused to other non-antibody proteins, such as receptor proteins e.g. etanercept. Fc domain fusions have also been used as research reagents, 'Fc tags', which facilitate fusion protein detection and purification. In addition, a number of alternative antibody structures comprising Fc domains have also been described see for example Dumont et al., 2006, Biodrugs, 20(3) 151-160, WO2005001025, WO2005077981, WO2005017148 and Hayden et al., 1994, Therapeutic Immunology, 1, 3-15. WO2005077981 describes antibodies in which each chain comprises two Fc domains i.e. each antibody chain comprises in linear sequence CH2 CH3 CH2 CH3 and these domains dimerise to form two functional Fc domains to provide enhanced effector functions. WO2005017148 and Hayden et al. supra describe single chain polypeptides comprising a single-chain Fv fused to half of an Fc domain i.e. sc-Fv-CH2 CH3. These polypeptides can exist as both monomers or dimers.

The binding specificity of antibodies has made these useful therapeutic agents, however, bivalent molecules such as antibodies are often inappropriate targeting agents for certain cell surface antigens. Bivalent binding can cause the target cell to undergo co-stimulation, activation and/or antigenic modulation, thereby offering the cell a means of evading complement and the various effector cells recruited by the Fc domain of the antibody. Instead, in order to target such cell surface antigens antibodies have typically been conjugated to drugs or toxins that kill the cells upon internalization.

In contrast, univalent antibody fragments do not cause antigenic modulation as no redistribution of surface antigen occurs and hence no co-stimulation and no internalization. It would be desirable therefore to retain the natural effector functions of an antibody in such fragments and thus avoid the need for costly and time consuming attachment of drugs or toxins. An example of one such antibody fragment was produced by proteolytic cleavage of a rabbit IgG by Glennie and Stevenson, 1982, Nature, 295, 712-713. The fragment comprised only a single Fab binding site but retained the entire Fc domain. The fragment was produced by papain digestion of a rabbit IgG antibody A12 allotypic variant which is glycosylated on one chain, making that chain resistant to papain digestion, thus allowing one Fab arm to be retained. The fragment produced was demonstrated to be more effective in invoking complement mediated lysis of cells than the whole IgG. Similar fragments have been produced from human IgG by proteolytic digestion (Michaelsen and Natvig, Scand. J. Immunology, 1973, 2, 299-312; Michaelsen and Natvig, Scand. J. Immunology, 1972, 1, 255-268) and by chemical cleavage (Wines and Easterbrook-Smith, Molecular Immunology, 1991, 28, 8, 855-863). These fragments are not practical to produce on a commercial scale as the use of proteolysis requires long preparation times and results in low yields and mixed products.

WO20050010125 describes hybrid proteins comprising two polypeptide chains, the first polypeptide chain comprising an Fc region and a biologically active molecule and the second polypeptide chain comprising an Fc region without the biologically active molecule of the first chain. The two chains are produced separately and are either allowed to dimerise or are chemically conjugated together. Although this achieves the desired functional molecule, the preparation is complex and involves low yielding chromatographic procedures.

Surprisingly we have now found that it possible to produce a functional Fc domain as a single-chain polypeptide. The polypeptides of the present invention therefore have the advantage that they can be produced recombinantly in large amounts and can be linked by any suitable means to any other molecule, such as a binding domain. Further, as the antibody constant domains form an Fc domain within the chain, the polypeptides of the present invention are not prone to dimerization thus, where desired, bi-valent binding domains can be avoided.

Accordingly the present invention provides a single chain polypeptide comprising two CH2 domains and two CH3 domains characterized in that said CH2 and CH3 domains form a functional Fc domain within the chain. The functional Fc domain in the single-chain polypeptides of the present invention is not formed by dimerization of two chains i.e. the two CH2 domains and two CH3 domains are present in a single chain and form a functional Fc domain within the single chain. Accordingly the present invention provides a single chain polypeptide comprising two CH2 domains and two CH3 domains characterized in that said CH2 and CH3 domains form a functional Fc domain within the chain and not by dimerization with another polypeptide chain. Accordingly, in the single chain polypeptide of the present invention a first CH2 domain is dimerized with a second CH2 domain and a first CH3 domain is dimerized with a second CH3 domain within the polypeptide chain.

The term 'functional' as used herein refers to the ability of the Fc domain formed within the single chain polypeptide to provide one or more effector functions usually associated with Fc domains although it will be appreciated that other functions may be engineered into such domains. Examples of effector functions include determining the half-life and/or distribution of the Fc polypeptide throughout the body, the ability of the Fc polypeptide to fix complement and the ability of the Fc polypeptide to bind to cell surface Fc receptors. Examples of such effector functions include but are not limited to, antibody-dependent cellular cytotoxicity (ADCC), antibody-dependent cellular phagocytosis (ADCP) and complement-dependent cytotoxicity (CDC).

The Fc domain of the present invention comprises four or more constant domains which may be derived from any suitable species and/or class of antibody. Preferably the constant domains are human. In humans there are five different classes or isotypes of antibodies including IgA (which includes IgA1 and IgA2), IgD, IgE, IgG (which includes subclasses IgG1, IgG2, IgG3 and IgG4) and IgM. Any suitable Fc domain may be used depending on the effector functions required. Typically the term Fc domain as used herein refers to the last two constant region immunoglobulin domains of IgA, IgD and IgG (CH2 and CH3) and the last three constant region domains of IgE and IgM (CH2, CH3 and CH4), although it will be appreciated that in certain circumstances not all the domains may be required, for example in the case of IgE or IgM only CH2 and CH3 domains may be sufficient. It will also be appreciated that more than one Fc domain may be formed within the single chain Fc polypeptide and that these Fc domains may be derived from the same or different isotypes.

The residues in antibody domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

In one embodiment the Fc domain is derived from IgA and the single-chain Fc polypeptide comprises two Cα2 domains and two Cα3 domains.

In one embodiment the Fc domain is derived from IgM and the single-chain Fc polypeptide comprises two Cμ2 domains, two Cμ3 domains and two Cμ4 domains.

In one embodiment the Fc domain is derived from IgD and the single-chain Fc polypeptide comprises two Cδ2 domains and two Cδ3 domains.

In one embodiment the Fc domain is derived from IgE and the single-chain Fc polypeptide comprises two Cε2 domains, two Cε3 domains and two Cε4 domains.

Preferably the Fc domain of the present invention is derived from an IgG and the single-chain Fc polypeptide comprises two Cγ2 and two Cγ3 domains. The preferred sequences for the Cγ2 domain of IgG1, IgG2, IgG3 and IgG4 for use in the present invention are provided in SEQ ID NOS: 2, 15, 28 and 41 respectively and the preferred sequences for the Cγ3 domain of IgG1, IgG2, IgG3 and IgG4 for use in the invention are provided in SEQ ID NOS: 3, 16, 29 and 42 respectively.

Accordingly, in one embodiment the present invention provides a single chain polypeptide comprising two Cγ2 domains and two Cγ3 domains characterized in that said Cγ2 and Cγ3 domains form a functional Fc domain within the chain i.e. a first Cγ2 domain dimerizes with a second Cγ2 domain and a first Cγ3 domain dimerizes with a second Cγ3 domain within the polypeptide chain It will be appreciated that the constant region domains for use in producing the Fc domain of the present invention may include variants of the naturally occurring constant domains described herein above. Such variants may comprise one or more amino acid variations compared to wild type constant domains. In one example the Fc domain of the present invention comprises at least one constant domain which varies in sequence from the wild type constant domain. It will be appreciated that the variant constant domains may be longer or shorter than the wild type constant domain. Preferably the variant constant domains are at least 50% identical or similar to a wild type constant domain. The term "Identity", as used herein, indicates that at any particular position in the aligned sequences, the amino acid residue is identical between the sequences. The term "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);
lysine, arginine and histidine (amino acids having basic side chains);
aspartate and glutamate (amino acids having acidic side chains);
asparagine and glutamine (amino acids having amide side chains); and
cysteine and methionine (amino acids having sulphur-containing side chains).

Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). In one example the variant constant domains are at least 60% identical or similar to a wild type constant domain. In another example the variant constant domains are at least 70% identical or similar. In another example the variant constant domains are at least 80% identical or similar. In another example the variant constant domains are at least 90% identical or similar. In another example the variant constant domains are at least 95% identical or similar.

In one embodiment the variant constant domains provide equivalent Fc effector functions compared to the wild type Fc domain. In one embodiment the variant constant domains provide improved effector functions. In one embodiment the variant constant domains provide altered effector functions. In one example the Fc domain provides no effector functions other than extended half-life. In one example the Fc domain provides FcR binding but not C1q binding. In one example the Fc domain provides C1q binding but not FcR binding.

A number of Fc variant polypeptides are known in the art, see for example Idusogie et al., Journal of Immunology, 2000, 164, 4178-4184 and Shields et al., Journal of Biological Chemistry, 2001, 276, 9, 6591-6604. A comprehensive list of Fc variants is provided by WO2005077981 (see in particular, paragraph number 80) and these are incorporated herein by reference.

Examples of Fc variants include in IgG1 N314Q (or N297Q), T318A (T299A), A349S (A330S) with P350A (P331A), L247A (L234A) with L248A (L235A) or P348A (P329A) (number in brackets is EU numbering). Where the IgG4 Fc domain is used the S241P (S228P) mutation may be used (Angal et al., Molecular Immunology, 1993, 30 (1), 105-108). It will be appreciated that any suitable variant may be produced and tested using routine methods known in the art.

The CH2, CH3 and where present CH4 domains of the single-chain Fc polypeptide of the present invention are linked in the single polypeptide chain such that they can still form a functional Fc domain within the chain. Accordingly any suitable amino acid linkers may be used to link these constant domains provided they allow a functional Fc domain to form within the single-chain polypeptide. Suitable amino acids for use in linkers of the present invention include, but are not limited to, small flexible amino acids such as Gly, Ser, Ala and Thr. In one embodiment the linker comprises or consists of glycine residues. In one embodiment the linker comprises or consists of serine residues. In one embodiment the linker comprises or consists of alanine residues. In one embodiment the linker comprises or consists of threonine residues. In one embodiment the linker comprises or consists of glycine and serine residues. In one embodiment the linker comprises or consists of glycine, serine and alanine residues. In one embodiment the linker comprises or consists of glycine, serine, alanine and threonine residues. For the avoidance of doubt, it is understood that all permutations of glycine and/or serine and/or alanine and/or threonine residues are included. In one example the linker comprises or consists of 30-80% glycine residues and 20-70% serine residues. In one example the linker comprises or consists of 35-50% glycine residues; 30-40% serine residues; 5-15% threonine residues and 10-20% alanine residues. In one example the amino acid residues are randomly distributed within the linker.

Specific examples of suitable linkers include glycine-serine polymers comprising for example repeats of sequences such as GS, GSGGS (SEQ ID NO: 92), GGGGS (SEQ ID NO: 93) and GGGS (SEQ ID NO: 94).

In one embodiment the Fc domain of the single chain polypeptide of the present invention comprises two CH2 domains and two CH3 domains.

In one embodiment the present invention provides a single chain Fc polypeptide comprising two CH2 domains and two CH3 domains wherein in N— to C-terminal sequence, a first CH2 domain is linked at its C-terminus to the N-terminus of a first CH3 domain and said first CH3 domain is linked at its C-terminus via a linker to the N-terminus of a second CH2 domain which is linked at its C-terminus to the N-terminus a second CH3 domain (as shown in FIG. 1).

In one embodiment the first CH2 domain is directly linked i.e. genetically fused at its C-terminus to the N-terminus of the first CH3 domain.

In one embodiment the second CH2 domain is directly linked i.e. genetically fused at its C-terminus to the N-terminus of the second CH3 domain.

Examples of suitable CH2 domains genetically fused to CH3 domain(s) are given in SEQ ID NOS: 5, 18, 31 and 44.

In one embodiment a linker is employed to link the C-terminus of the first CH2 domain to the N-terminus of the first CH3 domain.

In one embodiment a linker is employed to link the C-terminus of the second CH2 domain to the N-terminus of the second CH3 domain.

Where a linker is used to link (i) the C-terminus of the first CH2 domain to the N-terminus of the first CH3 domain and/or (ii) the C-terminus of the second CH2 domain to the N-terminus of the second CH3 domain the linker will be of sufficient length to allow a functional Fc domain to form within the chain. Typically the linker will only be a few amino acids in length, preferably less than 10 amino acids in length. Where a linker is used in both (i) and (ii) above the two linkers may be the same or different. Preferably the linkers will be approximately the same length.

The linker used to link the C-terminus of the first CH3 domain to the N-terminus of the second CH2 domain will be sufficiently long to allow a functional Fc domain to form within the chain i.e. it will be sufficiently long to allow a first CH2 domain to dimerise with a second CH2 domain and a first CH3 domain to dimerise with a second CH3 domain within the polypeptide chain. In one embodiment the linker is around 30-100 amino acids in length, in another embodiment the linker is around 40 to 100 amino acids in length. In one embodiment the linker is around 40 to 90 amino acids in length. In one embodiment the linker is around 40 to 80 amino acids in length, preferably 40 to 70 amino acids in length. Suitable amino acids for use in these linkers are described herein above. In one example the linker comprises or consists of 35-50% glycine residues; 30-40% serine residues; 5-15% threonine residues and 10-20% alanine residues. In one example the amino acid residues are randomly distributed within the linker. An example of a suitable linker is provided in SEQ ID NO:62. In one embodiment the linker may comprise, preferably towards its C-terminus one or more cysteine residues. In one embodiment the linker may comprise at its C-terminus the sequence of all or part of the hinge region of an antibody or variant thereof comprising one or more cysteine residues. Examples of suitable hinge sequences for use in the linkers of the present invention are provided in U.S. Pat. No. 5,677,425, WO9915549, WO9825971 and WO2005003171 and these are incorporated herein by reference. Other examples of suitable hinges are provided in SEQ ID NOs:53-57. Accordingly, in one example the linker of SEQ ID NO:62 further comprises at its C-terminus any one of the sequences provided in SEQ ID NOs: 53-57. In this embodiment, the linker is around 30 to 130 amino acids in length. In one embodiment the linker is around 50 to 100 amino acids in length. In one embodiment the linker is around 50 to 80 amino acids in length.

Figure 2:
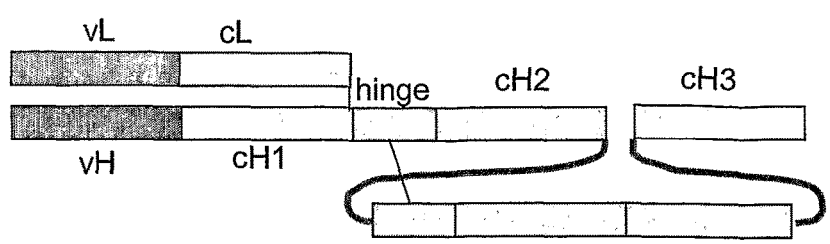
Figure 2:
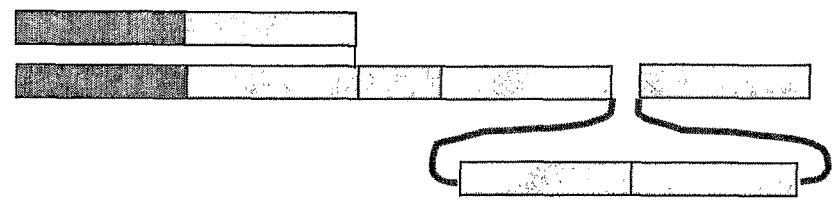
Figure 2:
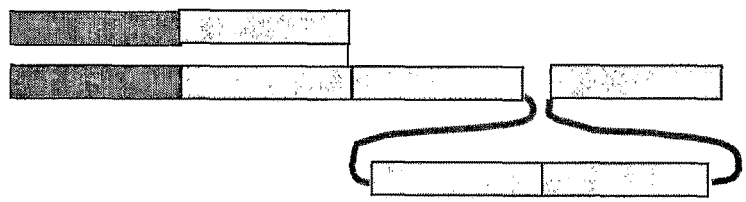

In another embodiment, the present invention provides a single chain Fc polypeptide comprising two CH2 domains and two CH3 domains wherein in N— to C-terminal sequence a first CH2 domain is linked at its C-terminus via a linker to the N-terminus of a second CH2 domain and said second CH2 domain is linked at its C-terminus to the N-terminus of a first CH3 domain and said first CH3 domain is linked at its C-terminus to the N-terminus of a second CH3 domain via a linker (as shown in FIG. 2).

In one embodiment the second CH2 domain is genetically fused at its C-terminus to the N-terminus of the first CH3 domain.

In one embodiment the C-terminus of the second CH2 domain is connected by a linker to the N-terminus of the first CH3 domain.

Where a linker is used to link the C-terminus of the second CH2 domain to the N-terminus of the first CH3 domain the linker will be of sufficient length to allow a functional Fc domain to form within the chain. Typically the linker will only be a few amino acids in length, preferably less than 10 amino acids in length.

The linker used to link the C-terminus of the first CH2 domain to the N-terminus of the second CH2 domain and the linker used to link the C-terminus of the first CH3 domain to the N-terminus of the second CH3 domain will be sufficiently long to allow a functional Fc domain to form within the chain. It will be appreciated that these two linkers may be the same or different in both composition and/or length. In one embodiment one or both of the linkers is between 15 and 50 amino acids in length. In one embodiment one or both of the linkers is between 15 and 40 amino acids in length. In one embodiment one or both of the linkers is between 20 and 40 amino acids in length. In another embodiment one or both of the linkers is between 20 and 35 amino acids in length. Suitable amino acids for use in these linkers are described herein above. In one example one or both of the linkers comprises or consists of 50-80% glycine residues and 10-30% serine residues. In one example the amino acid residues are randomly distributed within the linker. In one example the linker comprises the sequence (GGGGS)n where n=3 to 8. In one embodiment the linker between the C-terminus of the first CH2 domain and the N-terminus of the second CH2 domain comprises the sequence (GGGGS)n where n=5 (SEQ ID NO:63). In one embodiment the linker between the C-terminus of the first CH3 domain and the N-terminus of the second CH3 domain comprises the sequence (GGGGS)n where n=5 (SEQ ID NO:63).

In one embodiment the linker between the first CH2 domain and the second CH2 domain comprises, preferably towards its C-terminus, one or more cysteine residues. In one embodiment the linker comprises all or part of an antibody hinge sequence or variant thereof as described herein above. Accordingly, in one embodiment the linker between the C-terminus of the first CH2 domain and the N-terminus of the second CH2 domain having the sequence given in SEQ ID NO:63 further comprises at its C-terminus any one of the hinge sequences provided in SEQ ID NOs 53-57. In this embodiment the linker between the C-terminus of the first CH2 domain and the N-terminus of the second CH2 domain is between 25 and 90 amino acids in length. In one embodiment this linker is between 25 and 80 amino acids in length. In one embodiment this linker is between 25 and 70 amino acids in length. In one embodiment this linker is between 25 and 60 amino acids in length. In one embodiment this linker is between 25 and 50 amino acids in length. In one embodiment this linker is between 25 and 40 amino acids in length.

In one embodiment the Fc domain of the single chain Fc polypeptide of the present invention comprises two CH2 domains, two CH3 domains and one or two CH4 domains, preferably two.

Figure 3:
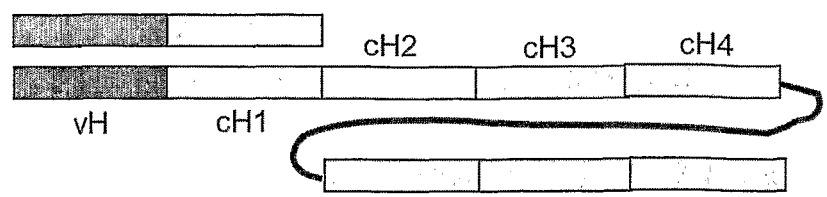
Figure 3:
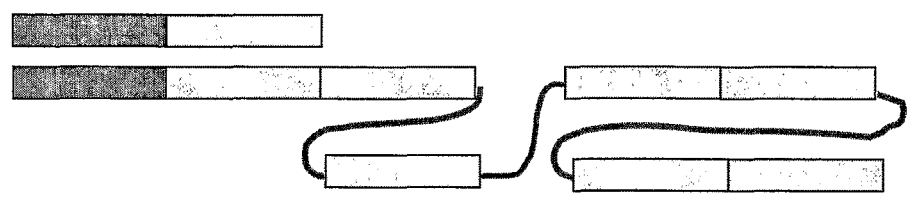
Figure 3:
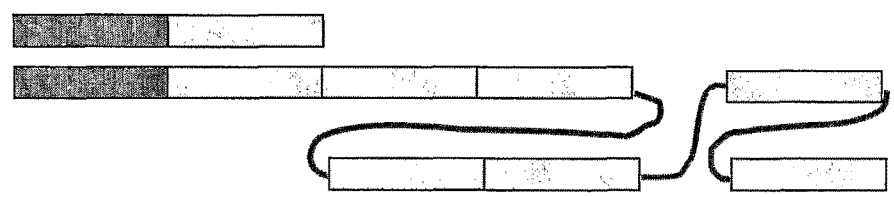

In one embodiment the present invention provides a single chain Fc polypeptide comprising two CH2 domains, two CH3 domains and two CH4 domains wherein in N— to C-terminal sequence, a first CH2 domain is linked at its C-terminus to the N-terminus of a first CH3 domain, said first CH3 domain is linked at its C-terminus to the N-terminus of a first CH4 domain and said first CH4 domain is linked at its C-terminus via a linker to the N-terminus of a second CH2 domain which is linked at its C-terminus to the N-terminus of a second CH3 domain which is linked at its C-terminus to the N-terminus of a second CH4 domain (see for example FIG. 3a).

In one embodiment one or more of the following domains are directly linked i.e. genetically fused (i) the C-terminus of the first CH2 domain to the N-terminus of the first CH3 domain (ii) the C-terminus of the second CH2 domain to the N-terminus of the second CH3 domain (iii) the C-terminus of the first CH3 domain to the N-terminus of the first CH4 domain (iv) the C-terminus of the second CH3 domain to the N-terminus of the second CH4 domain.

In one embodiment one or more of the following domains are connected by a linker (v) the C-terminus of the first CH2 domain to the N-terminus of the first CH3 domain (vi) the C-terminus of the second CH2 domain to the N-terminus of the second CH3 domain (vii) the C-terminus of the first CH3 domain to the N-terminus of the first CH4 domain (viii) the C-terminus of the second CH3 domain to the N-terminus of the second CH4 domain.

Where a linker is present between any one of (v, vi, vii or viii) this linker will be of sufficient length to allow a functional Fc domain to form within the chain. Typically the linker will only be a few amino acids in length. Where there is more than one linker it will be appreciated that these may be the same or different. Preferably the linkers will be approximately the same length.

The linker used to link the C-terminus of the first CH4 domain to the N-terminus of the second CH2 domain will be sufficiently long to allow a functional Fc domain to form within the chain. In one embodiment the linker is around 50-100 amino acids in length, in another embodiment the linker is around 60 to 100 amino acids in length. In one embodiment the linker is around 70 to 100 amino acids in length, preferably 80 to 100 amino acids in length. Suitable amino acids for use in these linkers have been described herein above. In one embodiment the linker may comprise, preferably towards its C-terminus, one or more cysteine residues. In one embodiment the linker comprises all or part of an antibody hinge sequence or variant thereof as described herein above.

In another embodiment, the present invention provides a single chain Fc polypeptide comprising two CH2 domains, two CH3 domains and two CH4 domains wherein in N— to C-terminal sequence a first CH2 domain is linked at its C-terminus via a linker to the N-terminus of a second CH2 domain and said second CH2 domain is linked at its C-terminus to the N-terminus of a first CH3 domain and said first CH3 domain is linked at its C-terminus to the N-terminus of a first CH4 domain which is linked at its C-terminus, via a linker, to the N-terminus of a second CH3 domain which is linked at its C-terminus to the N-terminus of a second CH4 domain (see for example FIG. 3b).

In one embodiment one or more of the following domains are directly linked i.e. genetically fused (i) the C-terminus of the second CH2 domain to the N-terminus of the first CH3 domain (ii) the C-terminus of the first CH3 domain to the N-terminus of the first CH4 domain (iii) the C-terminus of the second CH3 domain to the N-terminus of the second CH4 domain.

In one embodiment one or more of the following domains are connected by a linker (i) the C-terminus of the second CH2 domain to the N-terminus of the first CH3 domain (ii) the C-terminus of the first CH3 domain to the N-terminus of the first CH4 domain (iii) the C-terminus of the second CH3 domain to the N-terminus of the second CH4 domain.

Where a linker is present between one or more of (i) the C-terminus of the second CH2 domain and the N-terminus of the first CH3 domain (ii) the C-terminus of the first CH3 domain and the N-terminus of the first CH4 domain (iii) the C-terminus of the second CH3 domain and the N-terminus of the second CH4 domain the linker will be of sufficient length to allow a functional Fc domain to form within the chain. Typically the linker will only be a few amino acids in length. Where there is more than one linker it will be appreciated that these may be the same or different. Preferably the linkers will be approximately the same length.

The linker between the C-terminus of the first CH2 domain and the N-terminus of the second CH2 domain and the linker between the C-terminus of the first CH4 domain and the N-terminus of the second CH3 domain will be sufficiently long to allow a functional Fc domain to form within the chain. Suitable amino acids for these linkers have been described herein above.

The linker between the C-terminus of the first CH2 domain and the N-terminus of the second CH2 domain is typically between 15 and 40 amino acids in length. In another embodiment the linker is between 20 and 35 amino acids in length. In one embodiment the linker between the C-terminus of the first CH2 domain and the N-terminus of the second CH2 domain comprises the sequence (GGGGS)n where n=5 (SEQ ID NO:63).

In one embodiment the linker between the first CH2 domain and the second CH2 domain comprises, preferably towards its C-terminus, one or more cysteine residues. In one embodiment the linker comprises all or part of an antibody hinge sequence or variant thereof as described herein above which may comprise one or more cysteine residues. Suitable hinge sequences include those provided in SEQ ID NOs 53-57.

The linker between the C-terminus of the first CH4 domain and the N-terminus of the second CH3 domain is typically around 30-100 amino acids in length, in another embodiment the linker is around 40 to 100 amino acids in length. In one embodiment the linker is around 40 to 80 amino acids in length, preferably 40 to 70 amino acids in length. An example of a suitable linker is provided in SEQ ID NO:62.

In another embodiment, the present invention provides a single chain Fc polypeptide comprising two CH2 domains, two CH3 domains and two CH4 domains wherein in N— to C-terminal sequence a first CH2 domain is linked at its C-terminus to the N-terminus of a first CH3 domain and said first CH3 domain is linked at its C-terminus via a linker to the N-terminus of a second CH2 domain and said second CH2 domain is linked at its C-terminus to the N-terminus of a second CH3 domain which is linked at its C-terminus to the N-terminus of a first CH4 domain which is linked at its C-terminus, via a linker, to the N-terminus of a second CH4 domain (see for example FIG. 1c).

In one embodiment one or more of the following domains are directly linked i.e. genetically fused (i) the C-terminus of the first CH2 domain and the N-terminus of the first CH3 domain (ii) the C-terminus of the second CH2 domain and the N-terminus of the second CH3 domain (iii) the C-terminus of the second CH3 domain and the N-terminus of the first CH4 domain.

In one embodiment one or more of the following domains are connected by a linker (i) the C-terminus of the first CH2 domain and the N-terminus of the first CH3 domain (ii) the C-terminus of the second CH2 domain and the N-terminus of the second CH3 domain (iii) the C-terminus of the second CH3 domain and the N-terminus of the first CH4 domain.

Where a linker is present between one or more of (i) the C-terminus of the first CH2 domain and the N-terminus of the first CH3 domain (ii) the C-terminus of the second CH2 domain and the N-terminus of the second CH3 domain (iii) the C-terminus of the second CH3 domain and the N-terminus of the first CH4 domain the linker will be of sufficient length to allow a functional Fc domain to form within the chain. Typically the linker will only be a few amino acids in length. Where there is more than one linker it will be appreciated that these may be the same or different. Preferably the linkers will be approximately the same length.

The linker between the C-terminus of the first CH3 domain and the N-terminus of the second CH2 domain and the linker between the C-terminus of the first CH4 domain and the N-terminus of the second CH4 domain will be of sufficient length to allow a functional Fc domain to form within the chain.

The linker between the C-terminus of the first CH4 domain and the N-terminus of the second CH4 domain is typically between 15 and 40 amino acids in length. In another embodiment the linker is between 20 and 35 amino acids in length. In one embodiment the linker between the C-terminus of the first CH4 domain and the N-terminus of the second CH4 domain comprises the sequence (GGGGS)n where n=5 (SEQ ID NO:63).

The linker between the C-terminus of the first CH3 domain and the N-terminus of the second CH2 domain is typically around 30-100 amino acids in length, in another embodiment the linker is around 40 to 100 amino acids in length. In one embodiment the linker is around 40 to 80 amino acids in length, preferably 40 to 70 amino acids in length. An example of a suitable linker is provided in SEQ ID NO:62.

In one embodiment the linker between the first CH3 domain and the second CH2 domain comprises, preferably towards its C-terminus, one or more cysteine residues. In one embodiment this linker comprises all or part of an antibody hinge sequence or variant thereof as described herein above which may comprise one or more cysteine residues. Suitable hinge sequences include SEQ ID NOs 53-57.

In one embodiment the single chain Fc polypeptide of the present invention further comprises an amino acid linker genetically fused to the N-terminus of the first CH2 domain. The linker may comprise any suitable amino acids and be of any suitable length. In one embodiment the linker comprises one or more cysteine residues. In one embodiment the linker genetically fused to the N-terminus of the first CH2 domain comprises all or part of an antibody hinge sequence or variant thereof as described herein above. In one embodiment the linker comprises the sequence given in any one of SEQ ID NOs:53-57. In one embodiment one or more of the cysteine residues present in the linker are disulphide linked to one or more cysteine residues present in any one of the following linkers where present (i) the linker which connects the C-terminus of the first CH3 domain and the N-terminus of the second CH2 domain (see for example FIG. 1a) (ii) the linker which connects the C-terminus of the first CH2 domain to the N-terminus of the second CH2 domain (see for example FIG. 2a) or (iii) the linker which connects the C-terminus of the first CH4 domain to the N-terminus of the second CH2 domain.

In another embodiment the linker fused to the N-terminus may comprise all or part of the hinge region of an antibody or variant thereof in which one or more cysteines have been substituted for another amino acid, preferably serine. Examples of suitable linkers of this type are provided in SEQ ID NOs: 58-61.

Examples of single chain Fc polypeptides according to the present invention are provided for IgG1, 2, 3 and 4 in SEQ ID NOS: 8-13, 21-26, 34-39 and 47-52 respectively. See also FIG. 6 for examples of IgG1 sequences. The invention also extends to variants of these sequences as set out herein above. In one example the present invention provides a single chain Fc polypeptide comprising a sequence having at least 70% identity or similarity to any one of the sequences given in SEQ ID NOS: 8-13, 21-26, 34-39 and 47-52. In another example a single chain Fc polypeptide of the present invention comprises a sequence having at least 80% identity or similarity to any one of the sequences given in SEQ ID NOS: 8-13, 21-26, 34-39 and 47-52. In another example a single chain Fc polypeptide of the present invention comprises a sequence having at least 90% identity or similarity to any one of the sequences given in SEQ ID NOS: 8-13, 21-26, 34-39 and 47-52. In another example a single chain Fc polypeptide of the present invention comprises a sequence having at least 95% or 98% identity or similarity to any one of the sequences given in SEQ ID NOS: 8-13, 21-26, 34-39 and 47-52.

In one embodiment the single chain Fc polypeptide of the present invention further comprises a CH1 domain fused optionally via a hinge to the N-terminus of the first CH2 domain. Examples of suitable CH1 domains are provided in SEQ ID NOs 1, 14, 27 and 40.

The single chain Fc polypeptides of the present invention can be used in a number of applications, including therapeutic, diagnostic and research applications. Preferably the single chain Fc polypeptides of the present invention further comprise one or more other molecules which may be fused or otherwise linked at the N and/or C-terminus and/or elsewhere on the polypeptide. Such molecules include, but are not limited to, nucleic acids, small molecules, carbohydrates, proteins and peptides, including for example receptor proteins, antibodies and antibody fragments. The single-chain Fc polypeptide may be linked to another molecule, optionally via a linker (amino acid or chemical), by any suitable means known in the art, including for example, chemical conjugation, chemical cross-linking or genetic fusion. In one embodiment the single chain Fc polypeptide comprises a cysteine containing linker, such as an antibody hinge, at its N-terminus and one of these free cysteines is used as a site of attachment for another molecule, preferably a biologically active molecule as described below.

In one embodiment the single-chain Fc polypeptides of the present invention are used as an Fc tag, for example to aid protein purification and/or protein detection. Accordingly in one embodiment the single-chain Fc polypeptide further comprises at its N-terminus all or part of another protein. Such Fc fusions advantageously do not dimerise unlike currently available Fc fusions thus ensuring that the fusion protein remains monomeric. In certain applications, where it is desirable to be able to remove the Fc domain, for example after purification, the single-chain Fc polypeptide may be linked to another protein via a cleavable linker.

In one embodiment the single-chain Fc polypeptide of the present invention is linked at its N and/or C-terminus to a biologically active molecule. The biologically active molecule may be any protein or other suitable molecule, including nucleic acids, small molecules, carbohydrates, receptor proteins or immunoglobulins. Some examples of biologically active molecules include enzymes, antibody fragments, domain antibodies, single chain antibodies, aptamers, Microbodies™, binding agents based on protein scaffolds (see for example Nygren and Uhlen, 1997, Current Opinion in Structural Biology, 7, 463-469) versabodies, avimers, adnectins, anticalins, phylomers, aptamers, cyclic peptides, peptides, antiviral agents, hemostatic agents and cytokines and growth factors such as EPO, RANTES, interleukins such as IL-1, IL-2, IL-3, IL-4, IL-5, IL-6, IL-8, IL-12, IL-13, IL-16 or IL-17, interferons such as interferon α, interferon β or interferon γ, tumour necrosis factor-α, tumor necrosis factor-β, colony stimulating factors such as G-CSF or GM-CSF.

In one embodiment the biologically active molecule brings the single-chain Fc polypeptide of the present invention into contact with a desired target, for example a target protein. In one embodiment the biologically active molecule binds to a desired target protein. In one example the target protein is a cell-associated protein, for example a cell surface protein on cells such as bacterial cells, yeast cells, T-cells, endothelial cells or tumour cells, or it may be a soluble protein. Target proteins may also be any medically relevant protein such as those proteins upregulated during disease or infection, for example receptors and/or their corresponding ligands. Particular examples of cell surface proteins include adhesion molecules, for example integrins such as β1 integrins e.g. VLA-4, E-selectin, P selectin or L-selectin, CD2, CD3, CD4, CD5, CD7, CD8, CD11a, CD11b, CD18, CD19, CD20, CD23, CD25, CD33, CD38, CD40, CD45, CDW52, CD69, CD134 (OX40), ICOS, BCMP7, CD137, CD27L, CD28, CD40L, CTLA-4, CD22, CDCP1, DPCR1, DPCR1, dudulin2, FLJ20584, FLJ40787, HEK2, KIAA0634, KIAA0659, KIAA1246, KIAA1455, LTBP2, LTK, MAL2, MRP2, nectin-like2, NKCC1, PTK7, RAIG1, TCAM1, SC6, BCMP101, BCMP84, BCMP11, DTD, carcinoembryonic antigen (CEA), human milk fat globulin (HMFG1 and 2), MHC Class I and MHC Class II antigens, and VEGF, and where appropriate, receptors thereof.

In one embodiment the target protein is a soluble protein. Soluble proteins include interleukins such as IL-1, IL-2, IL-3, IL-4, IL-5, IL-6, IL-8, IL-12, IL-13, IL-16 or IL-17, viral proteins for example respiratory syncytial virus or cytomegalovirus proteins, immunoglobulins, such as IgE, interferons such as interferon α, interferon β or interferon γ, tumour necrosis factor-α, tumor necrosis factor-β, colony stimulating factors such as G-CSF or GM-CSF, and platelet derived growth factors such as PDGF-α, and PDGF-β and where appropriate receptors thereof.

In one embodiment the single-chain Fc polypeptides of the present invention may be used to functionally alter the activity of a particular protein to which the biologically active molecule binds. For example the single-chain Fc polypeptide may neutralize, antagonize or agonize the activity of a protein. In one embodiment the binding of the single-chain Fc polypeptide to a cell via the biologically active molecule results in cell killing e.g. via complement mediated cytotoxicity.

In one embodiment the biologically active molecule is a monovalent binding domain, in particular, a monovalent protein such as a receptor or fragment thereof or an immunoglobulin or fragment thereof.

In one embodiment the biologically active molecule is a receptor that may be naturally expressed on a cell surface or inside the cell. Examples of suitable receptors include, but are not limited to, viral receptors, cytokine receptors, growth factor receptors, hormone receptors and bacterial receptors. It will be appreciated that the term 'receptor' as used herein also includes suitable fragments of such receptors, an example of which includes the extracellular domain of a receptor. In one example the receptor is the human gp130 receptor or a cytokine binding fragment thereof, such as domain 1, 2 and/or 3. In one example the biologically active molecule comprises domain 1 of the gp130 receptor or a fragment thereof. In one example the biologically active molecule comprises amino acids 1 to 125 of SEQ ID NO:91. In one example the biologically active molecule comprises domain 2 and domain 3 of the gp130 receptor. In one example the biologically active molecule comprises domain 1, domain 2 and domain 3 of the gp130 receptor. It will also be appreciated that the term 'receptor' as used herein includes modified forms of naturally occurring receptors, including for example amino acid substitutions, additions or deletions. In one example a receptor comprising two chains may be produced as a single chain and linked to a single chain Fc polypeptide of the present invention. In one example the receptor may comprise all or part of the extracellular domains of the alpha and beta chains of the T cell receptor (TCR). Preferably these alpha and beta extracellular domains are linked in a single chain by a suitable linker which is in turn linked to a single chain Fc polypeptide of the present invention.

Preferably the monovalent binding protein is an antibody fragment. Examples of suitable antibody fragments include but are not limited to, scFv, Fab, Fab', $V_{HH}$, Fv, Vκ, VH, Vλ, epitope-binding fragments of any of the above. Examples of suitable antibody fragments include those described in Adair and Lawson, 2005. Therapeutic antibodies. *Drug Design Reviews—Online* 2(3):209-217, WO2005003169, WO2005003170 and WO2005003171.

An antibody fragment for use in the present invention can be derived from any class (e.g. IgG, IgE, IgM, IgD or IgA) or subclass of immunoglobulin molecule and may be obtained from any species including for example mouse, rat, shark, rabbit, pig, hamster, camel, llama, goat or human.

In one embodiment the antibody fragment is a monoclonal, humanized and/or chimeric antibody fragment.

Humanized antibodies are antibody molecules having one or more complementarity determining regions (CDRs) from a non-human species and a framework region from a human immunoglobulin molecule which optionally comprises one or more donor residues from the non-human species (see, for example, U.S. Pat. No. 5,585,089).

Chimeric antibodies have been genetically engineered so that the light and heavy chain genes are composed of immunoglobulin gene segments belonging to different species. Preferably the heavy and light chain constant regions are human and the variable regions are derived from another species.

Monoclonal antibodies may be prepared by any method known in the art such as the hybridoma technique (Kohler & Milstein, *Nature*, 1975, 256, 495-497), the trioma technique, the human B-cell hybridoma technique (Kozbor et al., *Immuunology Today*, 1983, 4, 72) and the EBV-hybridoma technique (Cole et al., "Monoclonal Antibodies and Cancer Therapy", pp. 77-96, Alan R. Liss, Inc., 1985).

Antibodies may also be obtained by any other suitable method such as those described in Babcook, J. et al., *Proc. Natl. Acad. Sci. USA*, 1996, 93 (15), 7843-7848, WO 92/02551, WO2004/051268 and WO2004/106377.

An antibody fragment for use in the present invention may be obtained from any whole antibody, especially a whole monoclonal antibody, using any suitable enzymatic cleavage and/or digestion techniques, for example by treatment with pepsin. Alternatively antibody fragments may be prepared by the use of recombinant DNA techniques involving the manipulation and re-expression of DNA encoding antibody variable and/or constant regions. Standard molecular biology techniques may be used to modify, add or delete amino acids or domains as desired. Any alterations to the variable or constant regions are still encompassed by the terms 'variable' and 'constant' regions as used herein.

The methods for creating and manufacturing antibodies and antibody fragments are well known in the art (see for example, Boss et al., U.S. Pat. No. 4,816,397; Cabilly et al., U.S. Pat. No. 6,331,415; Shrader et al., WO 92/02551; Ward et al., 1989, Nature, 341, 544; Orlandi et al., 1989, Proc. Natl. Acad. Sci. USA, 86, 3833; Riechmann et al., 1988, Nature, 322, 323; Bird et al, 1988, Science, 242, 423; Queen et al., U.S. Pat. No. 5,585,089; Adair, WO91/09967; Mountain and Adair, 1992, Biotechnol. Genet. Eng. Rev, 10, 1-142; Verma et al., 1998, Journal of Immunological Methods, 216, 165-181).

Antibody fragments for use in the present invention may possess a native or a modified hinge region comprising one or more cysteines. The native hinge region is the hinge region normally associated with the $C_H1$ domain of the antibody molecule. A modified hinge region is any hinge that differs in length and/or composition from the native hinge region. Such hinges can include hinge regions from other species, such as human, mouse, rat, rabbit, shark, pig, hamster, camel, llama or goat hinge regions. Other modified hinge regions may comprise a complete hinge region derived from an antibody of a different class or subclass from that of the $C_H1$ domain. Thus, for instance, a $C_H1$ domain of class γ1 may be attached to a hinge region of class γ4. Alternatively, the modified hinge region may comprise part of a natural hinge or a repeating unit in which each unit in the repeat is derived from a natural hinge region. In a further alternative, the natural hinge region may be altered by converting one or more cysteine or other residues into neutral residues, such as serine or alanine, or by converting suitably placed residues into cysteine residues. By such means the number of cysteine residues in the hinge region may be increased or decreased. Other modified hinge regions may be entirely synthetic and may be designed to possess desired properties such as length, cysteine composition and flexibility.

A number of modified hinge regions have already been described for example, in U.S. Pat. No. 5,677,425, WO9915549, WO9825971 and WO2005003171 and these are incorporated herein by reference. In one example the protein for use in the present invention is a Fab' fragment with a native or a modified hinge region.

In one example, one or more cysteines may be engineered into the antibody fragments of the present invention, for example to create surface exposed cysteine(s) (U.S. Pat. No. 5,219,996). Thus by using suitable engineering techniques the number of cysteines in an antibody fragment may be modified in order to provide a specific number of sites for example for effector molecule attachment.

In one embodiment the single chain-Fc polypeptide of the present invention further comprises an antibody fragment.

In one embodiment the antibody fragment is a single chain-Fv polypeptide. In one embodiment the single chain-Fc polypeptide of the present invention further comprises a single-chain Fv polypeptide. In one embodiment the C-terminus of the VH domain of the sc-Fv is genetically fused to the N-terminus of the first CH2 domain, optionally via one of the linkers described herein above. In one embodiment the C-terminus of the VL domain of the sc-Fv is genetically fused to the N-terminus of the first CH2 domain, optionally via one of the linkers described herein above.

In one embodiment the biologically active molecule is a Fab or Fab' (See for example FIG. 1). In one embodiment the single chain-Fc polypeptide of the present invention further comprises an antibody Fab or Fab' fragment. In one embodiment the C-terminus of the VH—CH1 chain of the Fab or Fab' is genetically fused to the N-terminus of a single-chain Fc polypeptide of the present invention. In this embodiment the VL-CL chain of the Fab or Fab' is linked to the VH—CH1 chain by a disulphide bond, preferably the native interchain disulphide bond. In one embodiment the C-terminus of the VL-CL chain of the Fab or Fab' is genetically fused to the N-terminus of a single-chain Fc polypeptide of the present invention. In this embodiment the VH—CH1 chain of the Fab or Fab' is linked to the VL-CL by a disulphide bond, preferably the native interchain disulphide bond.

The single chain Fc polypeptide of the present invention may have one or more effector molecules attached. Effector molecules may be attached by any suitable method, for example by chemical conjugation or genetic fusion.

The term 'effector molecule' as used herein includes, for example, antineoplastic agents, drugs, toxins (such as enzymatically active toxins of bacterial or plant origin and fragments thereof e.g. ricin and fragments thereof) biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy. It will be appreciated that an effector molecule may comprise a single effector molecule or two or more such molecules so linked as to form a single moiety that can be attached to a protein using the process of the present invention.

Particular antineoplastic agents include cytotoxic and cytostatic agents for example alkylating agents, such as nitrogen mustards (e.g. chlorambucil, melphalan, mechlorethamine, cyclosphophamide, or uracil mustard) and derivatives thereof, triethylenephosphoramide, triethylenethiophosphor-amide, busulphan, or cisplatin; antimetabolites, such as methotrexate, fluorouracil, floxuridine, cytarabine, mercaptopurine, thioguanine, fluoroacetic acid, or fluorocitric acid, antibiotics, such as bleomycins (e.g. bleomycin sulphate), doxorubicin, daunorubicin, mitomycins (e.g. mitomycin C), actionmycins (e.g. dactinomycin) plicamyin, calicheamicin and derivatives thereof, or esperamicin and derivatives thereof; mitotic inhibitors, such as etoposide, vincristine or vinblastine and derivatives thereof; alkaloids such as ellipticine; polyols such as taxicin-I or taxicin-II; hormones, such as androgens (e.g. dromostanolone or testolactone), progestins (e.g. megestrol acetate or medroxyprogesterone acetate), estrogens (e.g. dimethylstilbestrol diphosphate, polyestradiol phosphate or estramustine phosphate) or antiestrogens (e.g. tamoxifen); anthraquinones, such as mitoxantrone, ureas, such as hydroxyurea; hydrazines, such as procarbazine; or imidazoles, such as dacarbazine.

Chelated metals include chelates of di- or tripositive metals having a coordination number from 2 to 8 inclusive. Particular examples of such metals include technetium (Tc), rhenium (Re), cobalt (Co), copper (Cu), gold (Au), silver (Ag), lead (Pb), bismuth (Bi), indium (In), gallium (Ga), yttrium (Y), terbium (Tb), gadolinium (Gd), and scandium (Sc). In general the metal is preferably a radionuclide. Particular radionuclides include $^{99m}$Tc, $^{186}$Re, $^{188}$Re, $^{58}$Co, $^{60}$Co, $^{67}$Cu, $^{195}$Au, $^{199}$Au, $^{110}$Ag, $^{203}$Pb, $^{206}$Bi, $^{207}$Bi, $^{111}$In, $^{67}$Ga, $^{68}$Ga, $^{88}$Y, $^{90}$Y, $^{160}$Tb, $^{153}$Gd and $^{47}$Sc.

The chelated metal may be for example one of the above types of metal chelated with any suitable polyadentate chelating agent, for example acyclic or cyclic polyamines, polyethers, (e.g. crown ethers and derivatives thereof); polyamides; porphyrins; and carbocyclic derivatives.

In general, the type of chelating agent will depend on the metal in use. One particularly useful group of chelating agents in conjugates according to the invention, however, are acyclic and cyclic polyamines, especially polyaminocarboxylic acids, for example diethylenetriaminepentaacetic acid and derivatives thereof, and macrocyclic amines, e.g. cyclic tri-aza and tetra-aza derivatives (for example as described in International Patent Specification No. WO 92/22583); and polyamides, especially desferriox-amine and derivatives thereof.

Other effector molecules include other proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, albumin, toxins such as abrin, ricin A, pseudomonas exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factors.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741, 900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, rhodamine red, rhodamine green, B-phycoerythrin, R-phycoerythrin, allophycosyanin, Texas red, Pacific blue, Marina blue, Oregon green and the Alexa Fluor series 350, 405, 430, 488, 500, 514, 532, 546, 555, 568, 594, 610, 633, 647, 660, 680, 700 and 750; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

Synthetic or naturally occurring polymers for use as effector molecules include, for example optionally substituted straight or branched chain polyalkylene, polyalkenylene, or polyoxyalkylene polymers or branched or unbranched polysaccharides, e.g. a homo- or hetero-polysaccharide such as lactose, amylose, dextran, starch or glycogen. Particular optional substituents which may be present on the above-mentioned synthetic polymers include one or more hydroxy, methyl or methoxy groups. Particular examples of synthetic polymers include optionally substituted straight or branched chain poly(ethyleneglycol), poly (propyleneglycol), poly(vinylalcohol) or derivatives thereof, especially optionally substituted poly(ethyleneglycol) such as methoxypoly(ethyleneglycol) or derivatives thereof.

"Derivatives" as used herein is intended to include reactive derivatives, for example thiol-selective reactive groups such as an α-halocaraboxylic acid or ester, e.g. iodoacetamide, an imide, e.g. maleimide, a vinyl sulphone or disulphide malemides and the like. The reactive group may be linked directly or through a linker segment to the polymer. It will be appreciated that the residue of such a group will in some instances form part of the product as the linking group between the protein and the polymer.

It will be appreciated that one or more other domains or biologically active molecules may be genetically fused or otherwise conjugated to the C-terminus of the single-chain polypeptide.

In one embodiment the single-chain Fc polypeptide further comprises a transmembrane domain fused to the C-terminus of the single chain Fc polypeptide. The transmembrane domain allows the single-chain Fc polypeptides to be expressed on the surface of a cell. Accordingly, appropriate transmembrane domains may be used depending on the cell type of interest. A number of different transmembrane domains have been described, see for example WO97/ 23613, WO99/00494, WO99/57268, WO00/63374 and WO00/63373. Other examples of suitable transmembrane domains include the natural transmembrane domains with which immunoglobulins are expressed on the surface of B cells, see for example the sequences given in SEQ ID NOs: 65, 68, 71, 74, 77, 80, 83 and 86. In one embodiment the transmembrane domains are connected to the C-terminus of the single chain Fc polypeptide via a linker. In one embodiment this is the natural linker with which immunoglobulins are expressed on the surface of B cells, see for example the sequences given in SEQ ID NOs: 64, 67, 70, 73, 76, 79, 82 and 85.

In one embodiment the present invention provides a single-chain Fc polypeptide which further comprises a transmembrane domain and one or more signaling domains. In one embodiment the present invention provides a single-chain Fc polypeptide further comprising a transmembrane domain fused to the C-terminus, optionally via a linker, which is in turn fused at its C-terminus to one or more signaling domains. Suitable signaling domains are well known in the art and appropriate signaling and transmembrane domains may be chosen in order to obtain the desired expression and/or signaling in the cell in which the single-chain Fc is expressed.

In one example the intracellular domains are the natural intracellular domains with which immunoglobulins are expressed on the surface of B cells, see for example the sequences given in SEQ ID NOs: 66, 69, 72, 75, 78, 81, 84 and 87.

Examples of suitable signaling domains have also been described in WO97/23613, WO99/00494, WO99/57268, WO00/63372, WO00/63374, WO00/63373, WO01/32709, WO01/32866, WO01/32867, WO02/33101 and WO2004/039840.

In one embodiment where the single chain Fc polypeptide also comprises a biological molecule as described herein above, fused to its N-terminus, the single-chain Fc polypeptide can be used as a chimeric receptor protein. Such single-chain Fc polypeptides have the advantageous property that they do not dimerise on the surface of the cell and accordingly avoid inappropriate signaling in the absence of bound ligand.

The present invention also provides an isolated DNA sequence encoding any one of the single chain Fc polypeptides of the present invention. The DNA sequences of the present invention may comprise synthetic DNA, for instance produced by chemical processing, cDNA, genomic DNA or any combination thereof.

DNA sequences which encode a single chain Fc polypeptide of the present invention can be obtained by methods well known to those skilled in the art. For example, DNA sequences coding for part or all of the antibody Fc domains may be synthesized as desired from the determined DNA sequences or on the basis of the corresponding amino acid sequences. DNA coding for antibody Fc constant domains is widely available to those skilled in the art and can be readily synthesized on the basis of their known amino acid sequences.

Standard techniques of molecular biology may be used to prepare DNA sequences coding for the single chain Fc polypeptide of the present invention. Desired DNA sequences may be synthesized completely or in part using oligonucleotide synthesis techniques. Site-directed mutagenesis and polymerase chain reaction (PCR) techniques may be used as appropriate.

The present invention also relates to a cloning or expression vector comprising one or more DNA sequences of the present invention. Accordingly, provided is a cloning or expression vector comprising one or more DNA sequences encoding a single chain Fc polypeptide of the present invention. In one embodiment the cloning or expression vector comprises a single DNA sequence, encoding the entire single chain Fc polypeptide and optionally all or part of the biologically active molecule e.g. a scFv or $V_{HH}$. In another embodiment the cloning or expression vector comprises two DNA sequences, for example the first DNA sequence encoding the single chain Fc polypeptide and one chain of biologically active molecule, eg. VH—CH1 and the second DNA sequence encoding a second chain of the biologically active molecule domain e.g. VL-CL. Preferably, a vector according to the present invention comprises an appropriate leader sequence, such as an antibody leader sequence.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more cloning or expression vectors comprising one or more DNA sequences encoding a single chain Fc polypeptide of the present invention. Any suitable host cell/vector system may be used for expression of the DNA sequences encoding the single chain Fc polypeptide of the present invention. Bacterial, for example *E. coli*, and other microbial systems may be used or eukaryotic, for example mammalian, host cell expression systems may also be used. Suitable mammalian host cells include NS0, CHO, myeloma or hybridoma cells.

The present invention also provides a process for the production of a single chain Fc polypeptide according to the present invention comprising culturing a host cell containing a vector of the present invention under conditions suitable for leading to expression of protein from DNA encoding the single chain Fc polypeptide of the present invention, and isolating the single chain Fc polypeptide.

The single chain Fc polypeptide may comprise only a single chain and where this is expressed alone or as a genetic fusion to the biologically active molecule only a single polypeptide coding sequence needs to be used to transfect the host cells for example, scFvscFc. For production of single-chain Fc polypeptides comprising a biologically active molecule which comprises two or more chains the cell line may be transfected with two or more vectors, a first vector encoding the single chain Fc polypeptide fused to a first chain of the biologically active molecule (e.g. VH—CH1) and a second vector encoding a second chain of the biologically active molecule (e.g. VL-CL). Alternatively, a single vector may be used, the vector including sequences encoding both chains of the biologically active molecule where one of the chains is fused to the single chain Fc polypeptide.

Once produced the single-chain Fc polypeptide of the present invention may be purified where necessary using any suitable method known in the art including, for example chromatography techniques such as ion exchange, size exclusion, protein A or hydrophobic interaction chromatography.

The size of the single-chain Fc polypeptide may be confirmed by conventional methods known in the art such as size exclusion chromatography and non-reducing SDS-PAGE. Such techniques can be used to confirm that the scFc has not dimerized. If dimers are detected then the monomeric single-chain Fc polypeptides may be purified away from the dimeric species using conventional chromatography techniques as described above.

The functionality of the single-chain Fc polypeptides of the present invention may be determined using any suitable method known in the art depending on the effector functions required, including those methods provided in the Examples. Suitable assays include Fc receptor binding assays, complement fixing assays, co-stimulation assays, cell killing assays, cytotoxicity assays and cytostatis assays. In addition, half-life can be measured using suitable pharmacokinetic methods known in the art.

Further, where the biologically active molecule binds to a surface protein and targets the single-chain Fc polypeptide to this surface expressed protein, other functional assays, such as cell killing assays (e.g. complement mediated cytotoxicity assays) may also be used. Accordingly, suitable functional assays may be readily established by one skilled in the art to determine whether the desired function is achieved.

The single chain Fc polypeptides of the present invention are useful in the treatment and/or prophylaxis of disease. Accordingly, the present invention also provides a pharmaceutical or diagnostic composition comprising a single chain Fc polypeptide of the present invention in combination with one or more of a pharmaceutically acceptable excipient, diluent or carrier. Accordingly, provided is the use of a single chain Fc polypeptide of the invention for the manufacture of a medicament. The composition will usually be supplied as part of a sterile, pharmaceutical composition that will normally include a pharmaceutically acceptable carrier. A pharmaceutical composition of the present invention may additionally comprise a pharmaceutically-acceptable adjuvant.

The present invention also provides a process for preparation of a pharmaceutical or diagnostic or research reagent composition comprising adding and mixing the single chain Fc polypeptide of the present invention together with one or more of a pharmaceutically acceptable excipient, diluent or carrier.

The single-chain Fc polypeptide may be the sole active ingredient in the pharmaceutical or diagnostic composition or may be accompanied by other active ingredients including for example other antibody or non-antibody ingredients including for example anti-inflammatories and chemotherapeutic agents.

The pharmaceutical compositions preferably comprise a therapeutically effective amount of the single-chain Fc polypeptide of the invention. The term "therapeutically effective amount" as used herein refers to an amount of a therapeutic agent needed to treat, ameliorate or prevent a targeted disease or condition, or to exhibit a detectable therapeutic or preventative effect. For any single-chain Fc polypeptide, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 50 mg/kg, preferably 0.1 mg/kg to 20 mg/kg.

Pharmaceutical compositions may be conveniently presented in unit dose forms containing a predetermined amount of an active agent of the invention per dose.

Compositions may be administered individually to a patient or may be administered in combination (e.g. simultaneously, sequentially or separately) with other agents, drugs or hormones.

The dose at which the single-chain Fc polypeptide of the present invention is administered depends on the nature of the condition to be treated, the extent of the inflammation present and on whether the antibody molecule is being used prophylactically or to treat an existing condition.

The frequency of dose will depend on the half-life of the single-chain Fc polypeptide and the duration of its effect. If the single-chain Fc polypeptide has a short half-life (e.g. 2 to 10 hours) it may be necessary to give one or more doses per day. Alternatively, if the single-chain Fc polypeptide has a long half life (e.g. 2 to 15 days) it may only be necessary to give a dosage once per day, once per week or even once every 1 or 2 months.

The pharmaceutically acceptable carrier should not itself induce the production of antibodies harmful to the individual receiving the composition and should not be toxic. Suitable carriers may be large, slowly metabolized macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Preferred forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilizing and/or dispersing agents. Alternatively, the single-chain Fc polypeptide may be in dry form, for reconstitution before use with an appropriate sterile liquid.

Once formulated, the compositions of the invention can be administered directly to the subject. The subjects to be treated can be animals. However, it is preferred that the compositions are adapted for administration to human subjects.

The pharmaceutical compositions of this invention may be administered by any number of routes including, but not limited to, oral, pulmonary, intravenous, intramuscular, intra-arterial, intramedullary, intrathecal, intraventricular, transdermal, transcutaneous (for example, see WO 98/20734), subcutaneous, intraperitoneal, intranasal, enteral, topical, sublingual, intravaginal or rectal routes. Hyposprays and nebulisers may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be a single-chain Fc polypeptide. As such, it will be susceptible to degradation in the gastrointestinal tract. Thus, if the composition is to be administered by a route using the gastrointestinal tract, the composition will need to contain agents which protect the single-chain Fc polypeptide from degradation but which release the single-chain Fc polypeptide once it has been absorbed from the gastrointestinal tract.

A thorough discussion of pharmaceutically acceptable carriers is available in Remington's Pharmaceutical Sciences (Mack Publishing Company, N.J. 1991).

It is also envisaged that the single-chain Fc polypeptide of the present invention will be administered by use of gene therapy. In order to achieve this, DNA sequences encoding the single chain Fc polypeptide under the control of appropriate DNA components are introduced into a patient such that the single chain Fc polypeptide is expressed from the DNA sequence(s) and assembled in situ. Alternatively the single-chain Fc polypeptide may be transfected ex vivo into appropriate cells, such as T cells. Examples of suitable methods for ex vivo transfections are described in WO2004/039840.

The present invention also provides a single-chain Fc polypeptide for use in the treatment or prophylaxis of a pathological disorder that is selected from the group consisting of infections (viral, bacterial, fungal and parasitic), endotoxic shock associated with infection, arthritis, rheumatoid arthritis, asthma, pelvic inflammatory disease, Alzheimer's Disease, Crohn's disease, Peyronie's Disease, coeliac disease, gallbladder disease, Pilonidal disease, peritonitis, psoriasis, vasculitis, surgical adhesions, stroke, Type I Diabetes, lyme arthritis, meningoencephalitis, immune mediated inflammatory disorders of the central and peripheral nervous system such as multiple sclerosis and Guillain-Barr syndrome, other autoimmune disorders, pancreatitis, trauma (surgery), graft-versus-host disease, transplant rejection, cancer (both solid tumours such as melanomas, hepatoblastomas, sarcomas, squamous cell carcinomas, transitional cell cancers, ovarian cancers and hematologic malignancies and in particular acute myelogenous leukaemia, chronic myelogenous leukemia, gastric cancer and colon cancer), heart disease including ischaemic diseases such as myocardial infarction as well as atherosclerosis, intravascular coagulation, bone resorption, osteoporosis, periodontitis and hypochlorhydia.

Preferably the present invention provides a single-chain Fc polypeptide for use in the control of inflammatory diseases and cancer. Preferably, the single-chain Fc polypeptide can be used to reduce the inflammatory process or cancer or to prevent the inflammatory process or cancer.

EXAMPLES

The present invention will now be described by way of example, in which reference is made to:

FIG. 1(a)-(c): A diagrammatic representation of three examples of single chain Fc polypeptide according to the present invention which comprise an antibody Fab fragment and in which a linker connects the C-terminus of the first CH3 domain and the N-terminus of the second CH2 domain.

FIG. 2(a)-(c): A diagrammatic representation of three examples of single chain Fc polypeptide which comprise an antibody Fab fragment and in which a linker connects the C-terminus of the first CH2 domain to the N-terminus of the second CH2 domain and another linker connects the C-terminus of the first CH3 domain to the N-terminus of the second CH3 domain.

FIG. 3(a)-(c): A diagrammatic representation of three examples of single chain Fc polypeptide which comprise an antibody Fab fragment and in which:
(a) a linker connects the C-terminus of the first CH4 domain to the N-terminus of the second CH2 domain.
(b) a first linker connects the C-terminus of the first CH2 domain to the N-terminus of the second CH2 domain, a second linker connects the C-terminus of the second CH2 domain to the N-terminus of the first CH3 domain and a third linker connects the C-terminus of the first CH4 domain to the N-terminus of the second CH3 domain.
(c) a first linker connects the C-terminus of the first CH3 domain to the N-terminus of the second CH2 domain, a second linker connects the C-terminus of the second CH3 domain to the N-terminus of the first CH4 domain and a third linker connects the C-terminus of the first CH4 domain to the N-terminus of the second CH4 domain.

Figure 4A:
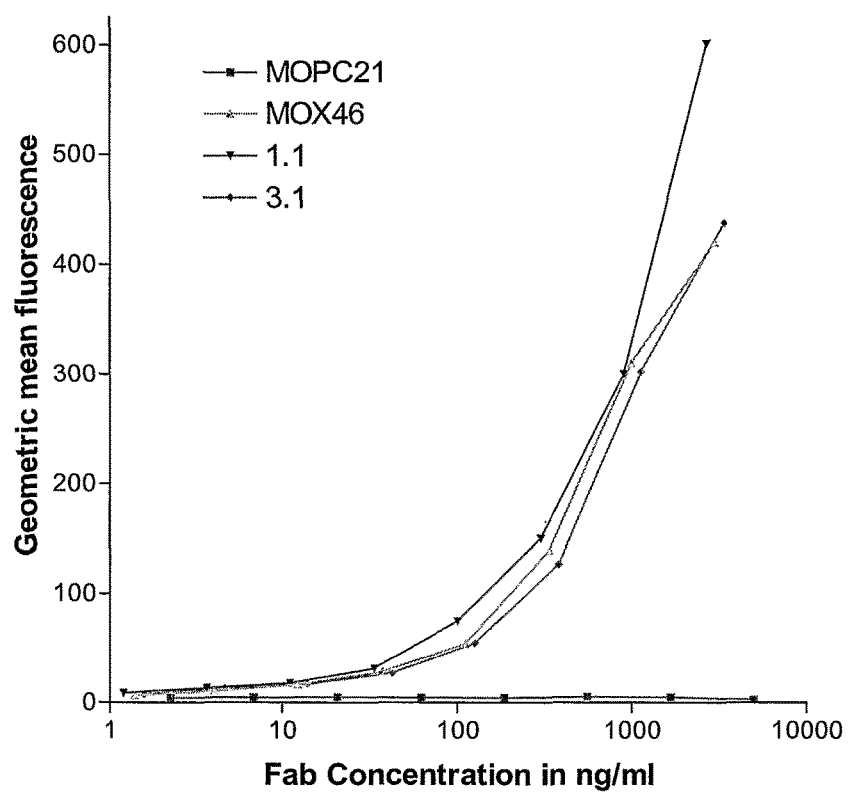
Figure 4B:
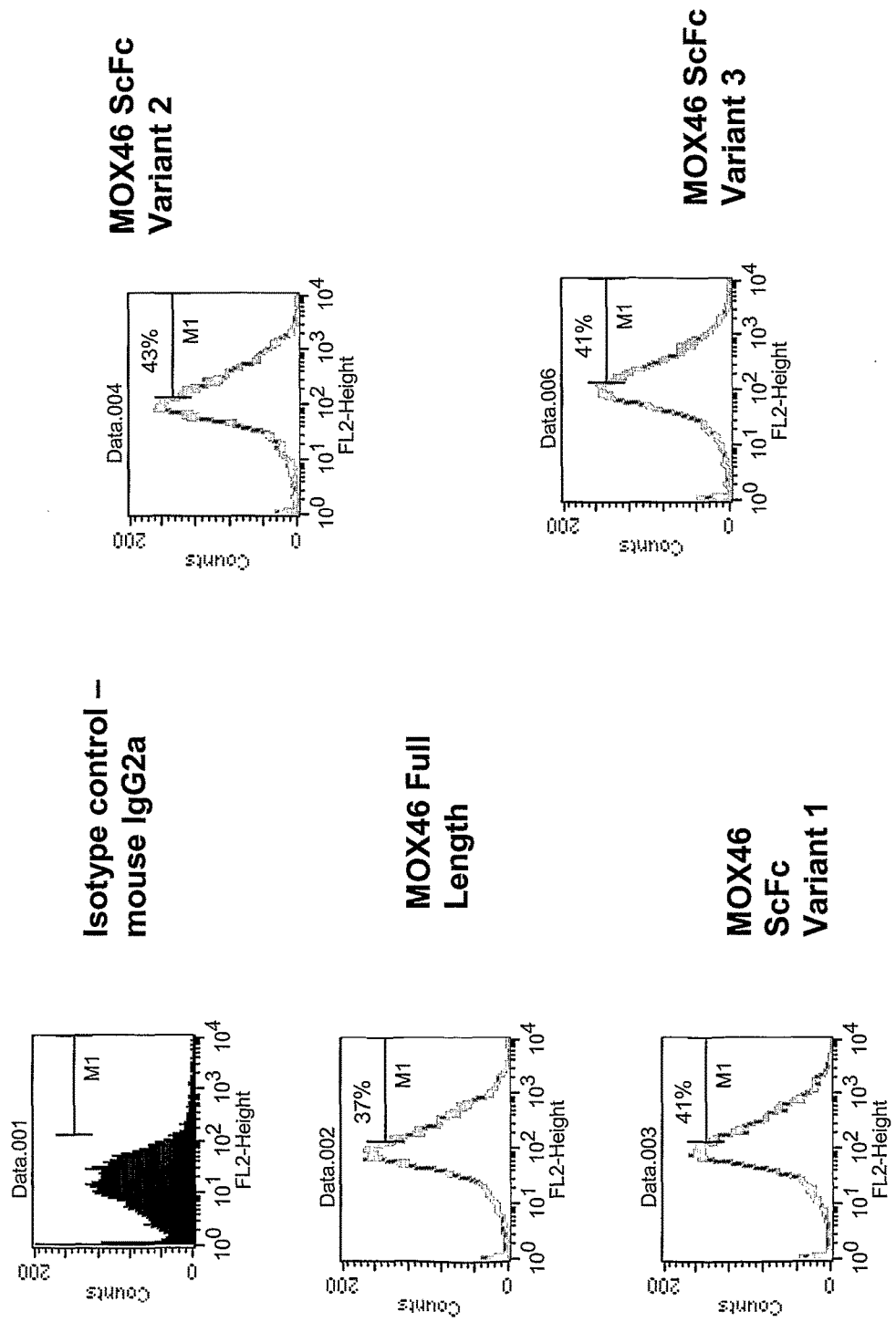

FIGS. 4a and 4b: demonstrate that the single chain Fc polypeptides bind to antigen recombinantly expressed on the surface of NS0 cells (FIG. 4a) and naturally expressed on the surface of activated T cells (FIG. 4b).

Figure 5A:
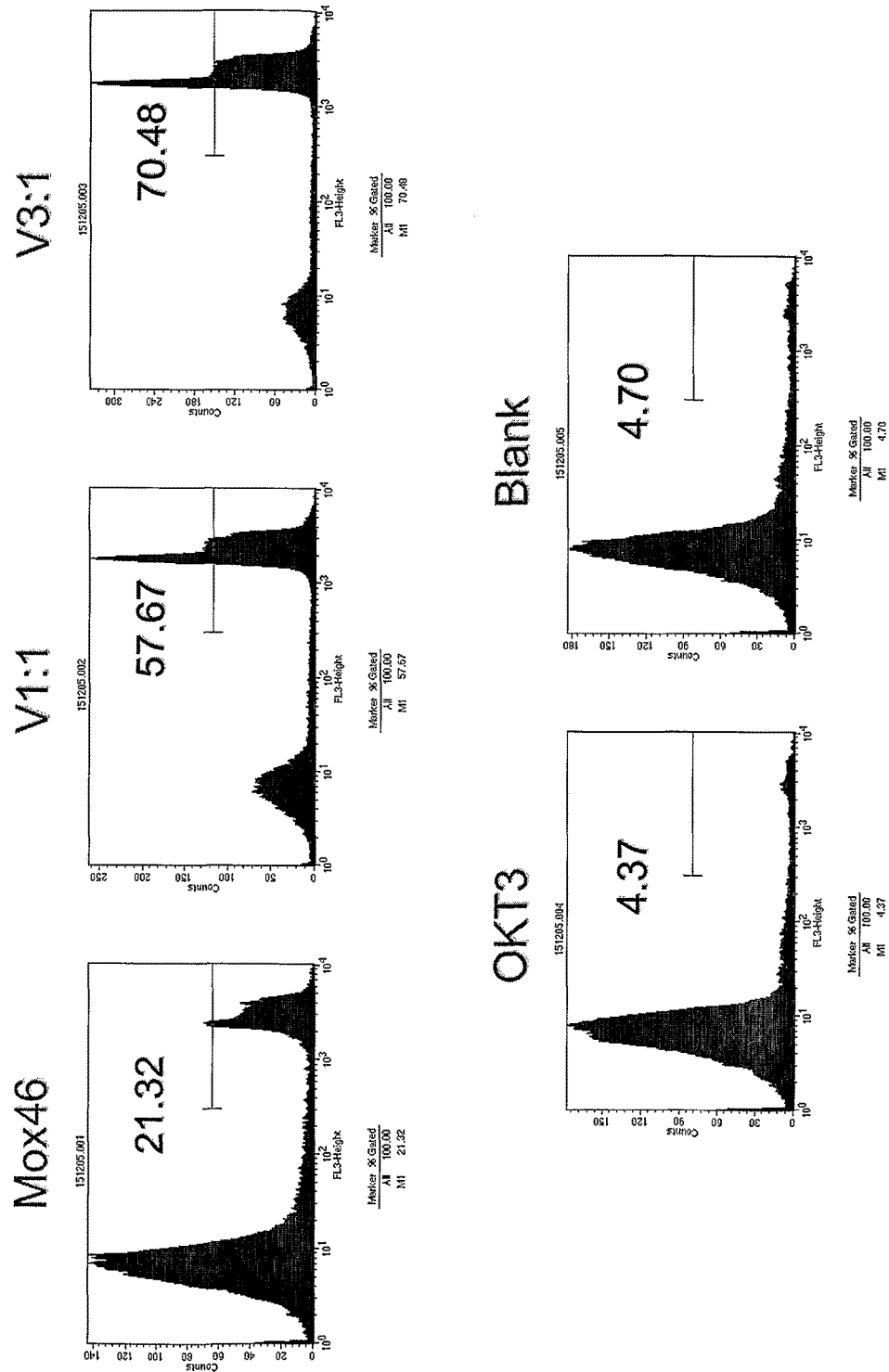

FIGS. 5a and b: show the ability of the single chain Fc polypeptides to induce cytotoxicity of NS0 cells in the presence of complement (a) but not in the absence of complement (b).

Figure 5B:
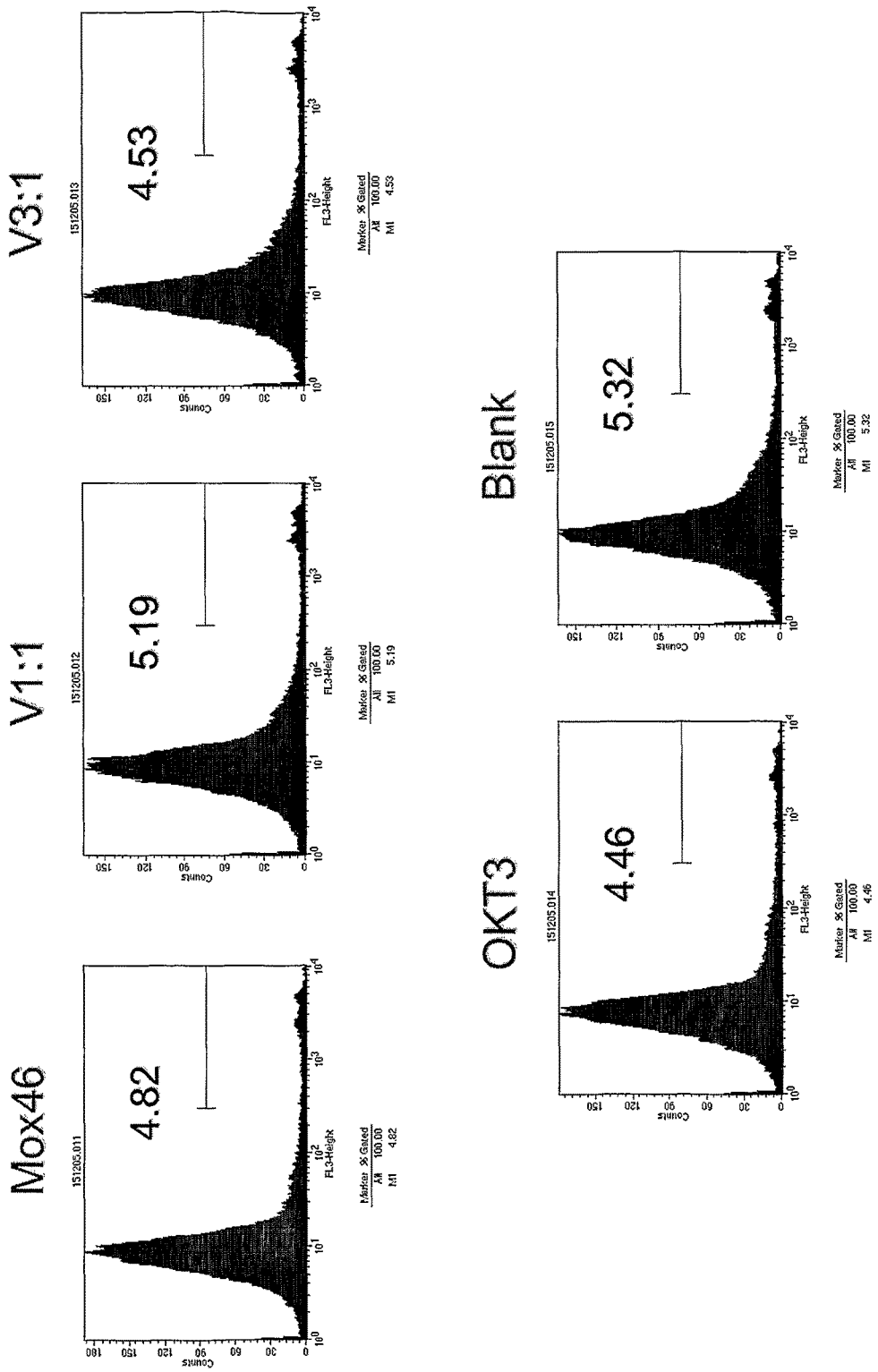
Figure 5C:
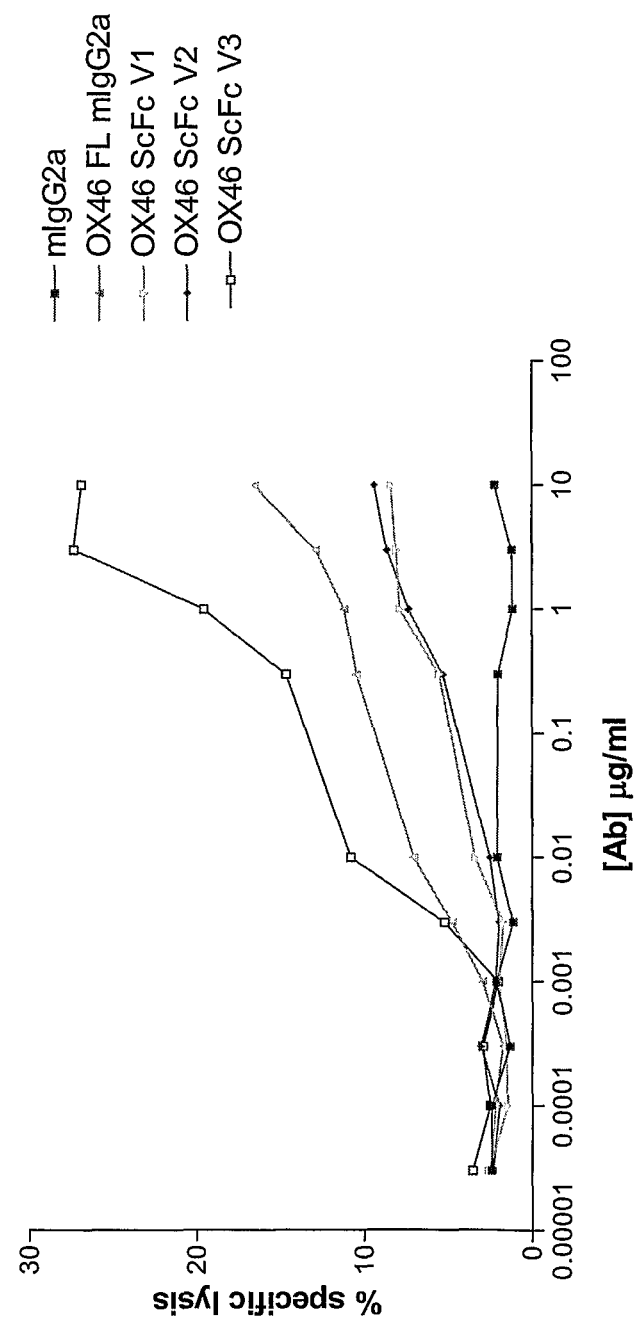
Figure 5D:
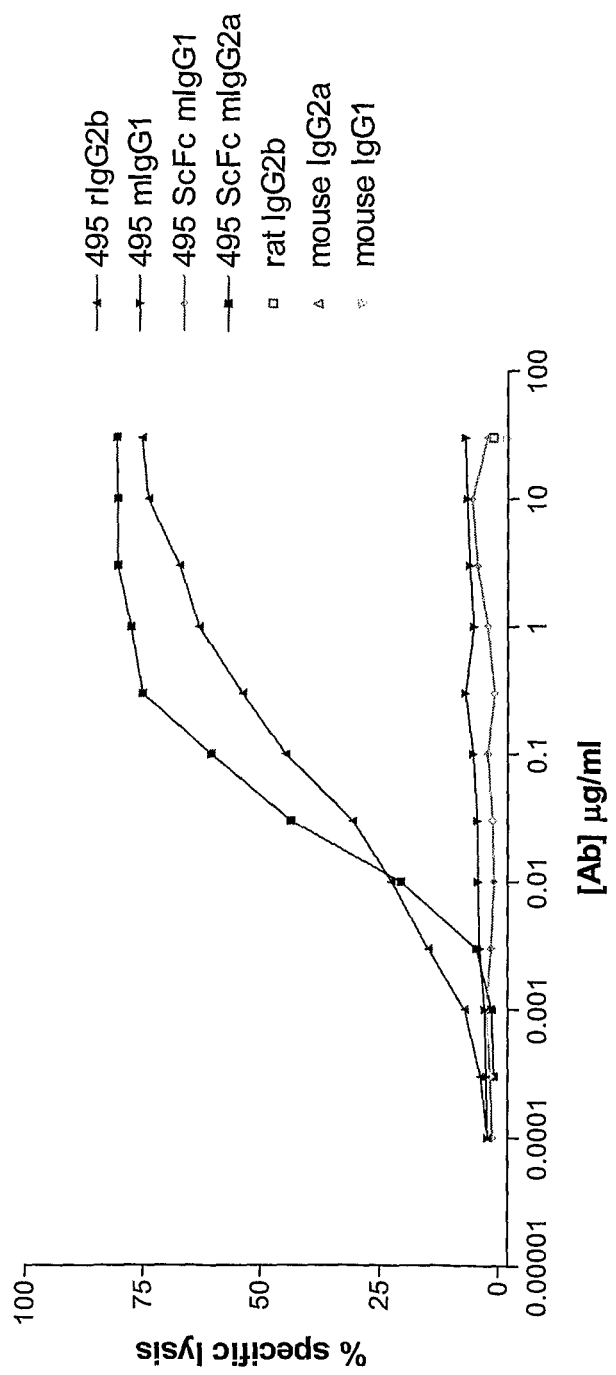

FIGS. 5c and 5d: show the ability of the single chain Fc polypeptides to induce complement-dependent cytotoxicity of activated T cells.

FIG. 6: Example sequences of single chain Fc polypeptides derived from IgG1. Hinge sequences are in italics and linkers are underlined.
(a) format as shown in FIG. 1(a) (SEQ ID NO: 9)
(b) format as shown in FIG. 1(b) (SEQ ID NO: 10)
(c) format as shown in FIG. 1(c) (SEQ ID NO: 8)
(d) format as shown in FIG. 2(a) (SEQ ID NO: 11)
(e) format as shown in FIG. 2(b) (SEQ ID NO: 12)
(f) format as shown in FIG. 2(c) (SEQ ID NO: 13)

EXAMPLE 1

Three murine single chain Fc polypeptides comprising a biologically active molecule at the N-terminus were designed in which the biologically active molecule was an antibody Fab fragment. The variable regions of the Fab fragment were derived from murine antibody, Mox46, that binds to a cell surface protein antigen. The Fc domains were derived from murine IgG2a and the three different versions of these domains are shown below. The linker sequences are underlined. Hinge sequences are in italics and where these constitute part of the linker sequence they are in italics and underlined.

Version 1 SEQ ID NO:88 (format as illustrated in FIG. 2b). The cysteines in the hinge between CH1 and CH2 have been substituted for serines.

*EPRGPTIKPSPPSKSP*APNLLGGPSVFIFPPKIKDVLMISLSPIVTCVVV

DVSEDDPDVQISWFVNNVEVHTAQTQTHREDYNSTLRVVSALPIQHQDWM

SGKEFKCKVNNKDLPAPIERTISKPK<u>GGGGSGGGGSGGGGSGGGGSGGGG</u>

<u>S</u>APNLLGGPSVFIFPPKIKDVLMISLSPIVTCVVVDVSEDDPDVQISWFV

NNVEVHTAQTQTHREDYNSTLRVVSALPHQHQDWMSGKEFKCKVNNKDLP

APIERTISKPKGSVRAPQVYVLPPPEEEMTKKQVTLTCMVTDFMPEDIYV

EWTNNGKTELNYKNTEPVLDSDGSYFMYSKLRVEKKNWVERNSYSCSVVH

EGLHNHHTTKSFSRTPGK<u>GGGGSGGGGSGGGGSGGGGSGGGGS</u>GSVRAPQ

VYLPPPEEEMTKKQVTLTCMVTDFMPEDIYVEWTNNGKTELNYKNTEPVL

DSDGSYFMYSKLRVEKKNWVERNSYSCSVVHEGLHNHHTTKSFSRTPGK

Version 2 SEQ ID NO: 89 (format as illustrated in FIG. 2a)

*EPRGPTIKPCP*APNLLGGPSVFIFPPKIKDVLMISLSPIVTCVVDVSEDD

PDVQISWFVNVEVHTAQTQTHREDYNSTLRVVSALPIQHQDWMSGKEFKC

KVNNKDLPAPIERTISKPK<u>GGGGSGGGGSGGGGSGGGGSGGGGS</u>*EPRGPT*

*IKPCP*APNLLGGPSVFIFPPKIKDVLMISLSPIVTCVVVDVSEDDPDVQI

SWFVNNVEVHTAQTQTHREDYNSTLRVVSALPIQHQDWMSGKEFCKVNN

KDLPAPIERTISKPKGSVRAPQVYVLPPPEEEMTKKQVTLTCMVTDFMPE

DIYVEWTNNGKTELNYKNTEPVLDSDGSYFMYSKLRVEKKNWVERNSYSC

SVVHEGLHNHHTTKSFSRTPGK<u>GGGGSGGGGSGGGGSGGGGSGGGGS</u>GSV

RAPQVYVLPPPEEEMTKKQVTLTCMVTDFMPEDIYVEWTNNGKTELNYKN

TEPVLDSDGSYFMYSKLRVEKKNWVERNSYSCSVVHEGLHNHHTTKSFSR

TPGK

Version 3 SEQ ID NO: 90 (format as illustrated in FIG. 1a). Linker comprises a truncated hinge 'PCP'.

*EPRGPTIKPCP*APNLLGGPSVFIFPPKIKDVLMISLSPIVTCVVVDVSED

DPDVQISWFVNNVEVHTAQTQTHREDYNSTLRVVSALPIQHQDWMSGKEF

KCKVNNKDLPAPIERTISKPKGSVRAPQVYVLPPPEEEMTKKQVTLTCMV

TDFMPEDIYVEWTNNGKTELNYKNTEPVLDSDGSYFMYSKLRVEKKNWVE

RNSYSCSVVHEGLHNHHTTKSFSRTPGK<u>GGSSTASGSGSGGSGTAGSSGG</u>

<u>AGSSGGSTTAGGSASGSGSTGSGTGGASSGGASGASGPCP</u>APNLLGGPSV

FIFPPKIKDVLMISLSPIVTCVVVDSEDDPDVQISWFVNNVEVHTAQTQ

THREDYNSTLRVVSALPIQHQDWMSGKEFKCKVNNKDLPAPIERTISKPK

GSVRAPQVYVLPPPEEEMTKKQVTLTCMVTDFMPEDIYVEWTNNGKTELN

YKNTEPVLDSDGSYFMYSKLRVEKKNWVERNSYSCSVVHEGLHNHHTTKS

FSRTPGK

The DNA encoding each of the single chain Fc polypeptides was synthesized with the same biologically active molecule at the N-terminus i.e. the VHCH1 domain from antibody MOX46.

The single chain Fc polypeptides comprising versions 1, 2 and 3 above were expressed in a pVAX vector (Invitrogen) in HEK293 cells (a human embryonic kidney epithelial cell line) using an antibody leader sequence (from mouse antibody B72.3 (Whittle et al., 1987, Protein Eng. 1(6) 499-505)). The VLCL chain of the MOX46 Fab fragment was produced in the same cell but in a separate vector. The resulting single chain Fc polypeptides were purified using protein A.

EXAMPLE 2

Antigen Binding

The ability of the single-chain Fc polypeptides (versions 1 and 3) to bind to antigen was compared to the same antibody variable regions (from the MOX46 antibody) expressed in a murine IgG1 framework and an irrelevant IgG. Recombinant NSO cells expressing the antigen on their surface ($5 \times 10^5$) were incubated with 100 µl of the single chain Fc polypeptides for 30 minutes at 4° C. The control was MOPC21 which was titrated from 5 µg/ml down in 1/3 dilutions. The MOX46 IgG and the single-chain Fc constructs were titrated in 1/3 dilutions. The cells were washed twice in Dulbecco's PBS containing 5% FCS and 0.1% sodium azide and then 100 µl of anti-mouse heavy and light chain PE labelled (Jackson) antibody diluted 1/250 was added for 30 minutes at 4° C. The cells were washed once more as before and analyzed by flow cytometry.

Both of the single-chain Fc constructs tested bound antigen (1.1 and 3.1), as did the MOX46 IgG. The irrelevant control did not bind to the antigen. See FIG. 4a.

The ability of the single chain Fc polypeptides (versions 1, 2 and 3) to bind antigen was also tested using the methods described above however primary activated T cells which naturally express the antigen on their surface were used instead of recombinant NS0 cells. The primary activated T cells were produced as follows: $1 \times 10^6$ D011 splenocytes were cultured with 200 ng/ml ovalbumin peptide 323-329 for 3 days, washed and resuspended in twice the volume of medium for a further 2 days. The activated cells were then purified by negatively isolating the CD4 T cells.

All three single-chain Fc constructs bound antigen, as did the MOX46 IgG. The irrelevant control did not bind to the antigen. See FIG. 4b.

EXAMPLE 3

Fc Receptor Binding

The ability of the single-chain Fc versions 1 and 3 to bind to Fc receptors CD64 (FcγRII) and CD32 (FcγRI) was determined by BIAcore. CD64 and CD32 were immobilized (approx 1000RU each) by amine coupling chemistry on flow cells 2 and 3 (respectively) of a standard CM5 Biacore chip. Flow cell 1 was set up as a reference flow cell to check for background binding. The single-chain Fc proteins were then injected in sequence over the chip to look for binding activity. All samples were run undiluted and at 1:2 and 1:5 dilutions. Background binding was insignificant with all samples.

Both versions 1 and 3 of the single-chain Fc were found to bind to both CD64 and CD32.

EXAMPLE 4

Complement-Dependent Cytotoxicity Assay using Recombinant NS0 Cells

Single-chain Fc versions 1 and 3 were tested for their ability to cause complement-mediated cytotoxicity of cells to which they were bound.

A recombinant NS0 line expressing the relevant antigen on its surface (5×10⁶) cells/ml media were mixed with 50 μl/ml baby rabbit complement (Serotec C12CA). Prior to use, the complement was reconstituted with 2 ml ice cold tissue culture grade distilled water. It was used within one hour of reconstitution and was maintained on ice until use. The agents tested were at a concentration of 2 μg/ml and plated onto a 96 well plate (Costar) in 100 μl volumes in duplicate. 100 μl of the cell/complement mix was added per well and the plate incubated at 37° C. for 4 hours. Cytotoxicity was assessed by uptake of the vital stain, propidium iodide (PI) by FACS. A stock solution of 20 mg/ml PI (Molecular Probes P-1304MP) was prepared in distilled water and then diluted in RPMI 1640 to give a final concentration in the well of 3 μg/ml. The cells were incubated for 10 min at RT in the dark, before being analyzed by flow cytometry.

FIG. 5a (with complement) and FIG. 5b (without complement) show that the both versions 1 and 3 of the single-chain Fc polypeptides (1.1 and 3.1) induce complement-dependent cytotoxicity.

EXAMPLE 5

Complement-Dependent Cytotoxicity Assay using Activated T Cells (i) Single chain Fc versions 1, 2 and 3 were tested for their ability to cause complement-mediated cytotoxicity of activated T cells which express the antigen bound by the MOX46 antibody on their surface. The methods used were as described in Example 4 except primary activated T cells were used instead of NS0 cells and these were produced as described in Example 2.

% specific lysis of cells was calculated as follows:

% PI positive cells in experimental condition−background % PI positive cells maximum % PI positive cells (lysis buffer)−background % PI positive cells All three versions of the single chain Fc polypeptides were found to induce complement-dependent cytotoxicity (FIG. 5c).

(ii) Another single chain Fc polypeptide (version 3) comprising an antibody Fab fragment derived from murine antibody, 495, that binds to a different cell surface protein antigen was produced as both an IgG1 and IgG2a format using murine Fc regions. The ability of these scFc proteins to cause complement-mediated cytotoxicity of activated T cells which express the antigen bound by the 495 antibody on their surface was tested. The methods used were as described in Example 4 except primary activated T cells were used which were produced as described in Example 2.

FIG. 5d clearly illustrates that as expected only the IgG2a format of the single chain Fc and the IgG2b format of the whole antibody 495 were able to induce complement-dependent cytotoxicity. The IgG1 formats were unable to induce complement-dependent cytotoxicity.

EXAMPLE 6

Receptor-scFc Fusion

The human gp130 receptor domain 1 was cloned as a single chain Fc (mouse gamma 1) fusion protein using the single chain Fc format illustrated in FIG. 1a. The sequence of the fusion protein is shown below.

Gp130 domain 1 scFc fusion protein (SEQ ID NO:91)

```
KLATMSVPTQ VLGLLLLWLT DARCELLDPC GYISPESPVV

QLHSNFTAVC VLKEKCMDYF HVNANYIVWK TNHFTIPKEQ

YTIINRTASS VTFTDIASLN IQLTCNILTF GQLEQNVYGI

TIISGSSAVP RDGGSKPGIC TVPEVSSVFI FPPKPKDVLT

ITLTPKVTCV VVDISKDDPE VQFSWFVDDV EVHTAQTQPR

EEQFNSTFRS VSELPIMHQD WLNGKEFKCR VNSAAFPAPI

EKTISKTKGR PKAPQVYTIP PPKEQMAKDK VSLTCMITDF

FPEDITVEWQ WNGQPAENYK NTQPIMDTDG SYFVYSKLNV

QKSNWSAGNT FTCSVLHEGL HNHHTEKSLS HSPGKGGSST

ASGSGSGGSG TAGSSGGAGS SGGSTTAGGS ASGSGSTGSG

TGGASSGGAS GASGVPRDGG SKPGICTVPE VSSVFIFPPK

PKDVLTITLT PKVTCVVVDI SKDDPEVQFS WFVDDVEVHT

AQTQPREEQF NSTFRSVSEL PIMHQDWLNG KEFKCRVNSA

AFPAPIEKTI SKTKGRPKAP QVYTIPPPKE QMAKDKVSLT

CMITDFFPED ITVEWQWNGQ PAENYKNTQP IMDTDGSYFV

YSKLNVQKSN WEAGNTFTCS VLHEGLHNHH TEKSLSHSPG

K*
```

The sequence in bold represents the gp130 receptor domain 1 (amino acids 1 to 125 of SEQ ID NO:91). The linker sequence is underlined. Hinge sequences are in italics and where they constitute part of the linker they are in italics and underlined. The sequence 'SSA' between the C-terminus of the gp130 domain 1 and the first hinge sequence are amino acids required to introduce the necessary Xho1 restriction site for cloning purposes.

The constructs were transiently expressed in a mammalian cell system (CHO L761) using a pVAX vector and the B72.3 mouse signal sequence. A western blot was prepared using the resulting scFc protein and the blot was probed with an anti-mouse Fc HRP (Jackson 115-035-071) and also with the biotinylated polyclonal anti gp130 (R&D BAF228), revealed with a strep-HRP. A protein corresponding to the predicted size of the gp130 domain 1 fusion protein was detected on the western blot. Previous attempts to express the gp130 domain 1 on its own or with a his tag attached had been unsuccessful. Fusion of the gp130 domain 1 to the single chain Fc polypeptide enabled the gp130 domain 1 to be expressed.

It will of course be understood that the present invention has been described by way of example only, is in no way meant to be limiting, and that modifications of detail can be made within the scope of the claims hereinafter. Preferred features of each embodiment of the invention are as for each of the other embodiments mutatis mutandis. All publications, including but not limited to patents and patent applications, cited in this specification are herein incorporated by reference as if each individual publication were specifically and individually indicated to be incorporated by reference herein as though fully set forth.

The invention claimed is:

1. An isolated monovalent polypeptide, comprising a single chain Fc polypeptide, and a monovalent binding domain;
wherein the single chain Fc polypeptide N to C-terminal sequence is:
a first CH2 domain linked via its C-terminus to an N-terminus of a first CH3 domain, and the first CH3 domain is linked at its C-terminus via at least one amino acid linker comprising repeat units of GSGGS (SEQ ID NO:92), GGGGS (SEQ ID NO:93), and GGGS (SEQ ID NO94) to the N-terminus of a second CH2 domain and the second CH2 domain linked at its C-terminus to the N-terminus of a second CH3 domain;
wherein the single chain Fc polypeptide does not contain cysteine amino acid residues in a hinge region;
wherein Fc domains in the single chain Fc polypeptide consist of two CH2 domains and two CH3 domains, wherein the first CH2 domain is intra-molecularly dimerised with the second CH2 domain and the first CH3 domain is intra-molecularly dimerised with the second CH3 domain within the single chain Fc polypeptide;
wherein the two CH2 domains and the two CH3 domains form a functional Fc domain within the single chain Fc polypeptide via at least one linker of 15 to 50 or 30 to 130 amino acids in length, or combinations thereof; and
wherein the single chain Fc polypeptide is linked at its N terminus to one biologically active molecule that is a monovalent binding protein selected from the group consisting of scFv, Fab, Fab', $V_{HH}$, and Fv, with the proviso that when the single chain polypeptide Fc is linked to the biologically active molecule via a linker, the linker does not contain cysteine amino acid residues.

2. The polypeptide of claim 1, wherein the at least one linker forming the functional single chain Fc polypeptide optionally comprises one or more amino acids selected from glycine, serine, alanine and threonine.

3. The polypeptide of claim 2, wherein the at least one linker forming the functional single chain Fc polypeptide comprises the sequence given in SEQ ID NO:62.

4. The polypeptide of claim 3, wherein the linker comprises all or part of an antibody hinge sequence or a modified antibody hinge sequence.

5. The polypeptide of claim 1, wherein the biologically active molecule and the single chain Fc polypeptide are linked by a peptide linker of between 1 and 100 amino acids in length.

6. The polypeptide of claim 1 to which one or more effector molecules are attached.

7. A pharmaceutical composition comprising the single chain Fc polypeptide of claim 1, in combination with one or more of a pharmaceutically acceptable excipient, diluent or carrier.

8. The pharmaceutical composition of claim 7, additionally comprising other active ingredients.

9. The polypeptide of claim 1, wherein the linker is 50 to 100 amino acids in length.

* * * * *

SEQUENCE LISTING

<160> NUMBER OF SEQ ID NOS: 94

<210> SEQ ID NO 1
<211> LENGTH: 98
<212> TYPE: PRT
<213> ORGANISM: Homo sapiens

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 2
<211> LENGTH: 110
<212> TYPE: PRT
<213> ORGANISM: Homo sapiens

<400> SEQUENCE: 2

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
                100                 105                 110

<210> SEQ ID NO 3
<211> LENGTH: 107
<212> TYPE: PRT
<213> ORGANISM: Homo sapiens

<400> SEQUENCE: 3

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

```
Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105
```

<210> SEQ ID NO 4
<211> LENGTH: 208
<212> TYPE: PRT
<213> ORGANISM: Artificial sequence
<220> FEATURE:
<223> OTHER INFORMATION: CH1CH2

<400> SEQUENCE: 4

```
Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Ala Pro Glu Leu Leu Gly Gly Pro Ser Val Phe Leu Phe Pro
            100                 105                 110

Pro Lys Pro Lys Asp Thr Leu Met Ile Ser Arg Thr Pro Glu Val Thr
        115                 120                 125

Cys Val Val Val Asp Val Ser His Glu Asp Pro Glu Val Lys Phe Asn
130                 135                 140

Trp Tyr Val Asp Gly Val Glu Val His Asn Ala Lys Thr Lys Pro Arg
145                 150                 155                 160

Glu Glu Gln Tyr Asn Ser Thr Tyr Arg Val Val Ser Val Leu Thr Val
                165                 170                 175

Leu His Gln Asp Trp Leu Asn Gly Lys Glu Tyr Lys Cys Lys Val Ser
            180                 185                 190

Asn Lys Ala Leu Pro Ala Pro Ile Glu Lys Thr Ile Ser Lys Ala Lys
        195                 200                 205
```

<210> SEQ ID NO 5
<211> LENGTH: 217
<212> TYPE: PRT
<213> ORGANISM: Homo sapiens

<400> SEQUENCE: 5

```
Ala Pro Glu Leu Leu Gly Gly Pro Ser Val Phe Leu Phe Pro Pro Lys
  1               5                  10                  15

Pro Lys Asp Thr Leu Met Ile Ser Arg Thr Pro Glu Val Thr Cys Val
             20                  25                  30

Val Val Asp Val Ser His Glu Asp Pro Glu Val Lys Phe Asn Trp Tyr
         35                  40                  45

Val Asp Gly Val Glu Val His Asn Ala Lys Thr Lys Pro Arg Glu Glu
     50                  55                  60

Gln Tyr Asn Ser Thr Tyr Arg Val Val Ser Val Leu Thr Val Leu His
```

```
            65                  70                  75                  80
    Gln Asp Trp Leu Asn Gly Lys Glu Tyr Lys Cys Lys Val Ser Asn Lys
                    85                  90                  95

Ala Leu Pro Ala Pro Ile Glu Lys Thr Ile Ser Lys Ala Lys Gly Gln
                    100                 105                 110

Pro Arg Glu Pro Gln Val Tyr Thr Leu Pro Pro Ser Arg Asp Glu Leu
                    115                 120                 125

Thr Lys Asn Gln Val Ser Leu Thr Cys Leu Val Lys Gly Phe Tyr Pro
                    130                 135                 140

Ser Asp Ile Ala Val Glu Trp Glu Ser Asn Gly Gln Pro Glu Asn Asn
    145                 150                 155                 160

Tyr Lys Thr Thr Pro Pro Val Leu Asp Ser Asp Gly Ser Phe Phe Leu
                    165                 170                 175

Tyr Ser Lys Leu Thr Val Asp Lys Ser Arg Trp Gln Gln Gly Asn Val
                    180                 185                 190

Phe Ser Cys Ser Val Met His Glu Ala Leu His Asn His Tyr Thr Gln
                    195                 200                 205

Lys Ser Leu Ser Leu Ser Pro Gly Lys
                    210                 215

<210> SEQ ID NO 6
<211> LENGTH: 315
<212> TYPE: PRT
<213> ORGANISM: Artificial sequence
<220> FEATURE:
<223> OTHER INFORMATION: CH1CH2CH3

<400> SEQUENCE: 6

Ala Ser Thr Lys Gly Pro Ser Val Phe Pro Leu Ala Pro Ser Ser Lys
    1               5                   10                  15

Ser Thr Ser Gly Gly Thr Ala Ala Leu Gly Cys Leu Val Lys Asp Tyr
                    20                  25                  30

Phe Pro Glu Pro Val Thr Val Ser Trp Asn Ser Gly Ala Leu Thr Ser
                    35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Gln Thr
    65                  70                  75                  80

Tyr Ile Cys Asn Val Asn His Lys Pro Ser Asn Thr Lys Val Asp Lys
                    85                  90                  95

Lys Val Ala Pro Glu Leu Leu Gly Gly Pro Ser Val Phe Leu Phe Pro
                    100                 105                 110

Pro Lys Pro Lys Asp Thr Leu Met Ile Ser Arg Thr Pro Glu Val Thr
                    115                 120                 125

Cys Val Val Val Asp Val Ser His Glu Asp Pro Glu Val Lys Phe Asn
                    130                 135                 140

Trp Tyr Val Asp Gly Val Glu Val His Asn Ala Lys Thr Lys Pro Arg
    145                 150                 155                 160

Glu Glu Gln Tyr Asn Ser Thr Tyr Arg Val Val Ser Val Leu Thr Val
                    165                 170                 175

Leu His Gln Asp Trp Leu Asn Gly Lys Glu Tyr Lys Cys Lys Val Ser
                    180                 185                 190

Asn Lys Ala Leu Pro Ala Pro Ile Glu Lys Thr Ile Ser Lys Ala Lys
                    195                 200                 205

Gly Gln Pro Arg Glu Pro Gln Val Tyr Thr Leu Pro Pro Ser Arg Asp
```

```
                210                 215                 220
Glu Leu Thr Lys Asn Gln Val Ser Leu Thr Cys Leu Val Lys Gly Phe
225                 230                 235                 240

Tyr Pro Ser Asp Ile Ala Val Glu Trp Glu Ser Asn Gly Gln Pro Glu
                245                 250                 255

Asn Asn Tyr Lys Thr Thr Pro Pro Val Leu Asp Ser Asp Gly Ser Phe
                260                 265                 270

Phe Leu Tyr Ser Lys Leu Thr Val Asp Lys Ser Arg Trp Gln Gln Gly
                275                 280                 285

Asn Val Phe Ser Cys Ser Val Met His Glu Ala Leu His Asn His Tyr
                290                 295                 300

Thr Gln Lys Ser Leu Ser Leu Ser Pro Gly Lys
305                 310                 315

<210> SEQ ID NO 7
<211> LENGTH: 330
<212> TYPE: PRT
<213> ORGANISM: Homo sapiens

<400> SEQUENCE: 7

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270
```

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 8
<211> LENGTH: 493
<212> TYPE: PRT
<213> ORGANISM: Artificial sequence
<220> FEATURE:
<223> OTHER INFORMATION: Format 1c

<400> SEQUENCE: 8

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys Gly Gly Ser Ser Thr Ala Ser
    210                 215                 220

Gly Ser Gly Ser Gly Gly Ser Gly Thr Ala Gly Ser Ser Gly Gly Ala
225                 230                 235                 240

Gly Ser Ser Gly Gly Ser Thr Thr Ala Gly Ser Ala Ser Gly Ser
                245                 250                 255

Gly Ser Thr Gly Ser Gly Thr Gly Gly Ala Ser Ser Gly Gly Ala Ser
            260                 265                 270

Gly Ala Ser Gly Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
    290                 295                 300
```

```
Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490

<210> SEQ ID NO 9
<211> LENGTH: 523
<212> TYPE: PRT
<213> ORGANISM: Artificial sequence
<220> FEATURE:
<223> OTHER INFORMATION: Format 1a

<400> SEQUENCE: 9

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175
```

```
Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
        210                 215                 220

Ser Leu Ser Leu Ser Pro Gly Lys Gly Gly Ser Ser Thr Ala Ser Gly
225                 230                 235                 240

Ser Gly Ser Gly Gly Ser Gly Thr Ala Gly Ser Ser Gly Ala Gly
                245                 250                 255

Ser Ser Gly Gly Ser Thr Thr Ala Gly Gly Ser Ala Ser Gly Ser Gly
            260                 265                 270

Ser Thr Gly Ser Gly Thr Gly Gly Ala Ser Gly Gly Ala Ser Gly
                275                 280                 285

Ala Ser Gly Glu Pro Lys Ser Cys Asp Lys Thr His Thr Cys Pro Pro
        290                 295                 300

Cys Pro Ala Pro Glu Leu Leu Gly Gly Pro Ser Val Phe Leu Phe Pro
305                 310                 315                 320

Pro Lys Pro Lys Asp Thr Leu Met Ile Ser Arg Thr Pro Glu Val Thr
                325                 330                 335

Cys Val Val Val Asp Val Ser His Glu Asp Pro Glu Val Lys Phe Asn
                340                 345                 350

Trp Tyr Val Asp Gly Val Glu Val His Asn Ala Lys Thr Lys Pro Arg
            355                 360                 365

Glu Glu Gln Tyr Asn Ser Thr Tyr Arg Val Val Ser Val Leu Thr Val
370                 375                 380

Leu His Gln Asp Trp Leu Asn Gly Lys Glu Tyr Lys Cys Lys Val Ser
385                 390                 395                 400

Asn Lys Ala Leu Pro Ala Pro Ile Glu Lys Thr Ile Ser Lys Ala Lys
                405                 410                 415

Gly Gln Pro Arg Glu Pro Gln Val Tyr Thr Leu Pro Pro Ser Arg Asp
            420                 425                 430

Glu Leu Thr Lys Asn Gln Val Ser Leu Thr Cys Leu Val Lys Gly Phe
            435                 440                 445

Tyr Pro Ser Asp Ile Ala Val Glu Trp Glu Ser Asn Gly Gln Pro Glu
        450                 455                 460

Asn Asn Tyr Lys Thr Thr Pro Pro Val Leu Asp Ser Asp Gly Ser Phe
465                 470                 475                 480

Phe Leu Tyr Ser Lys Leu Thr Val Asp Lys Ser Arg Trp Gln Gln Gly
                485                 490                 495

Asn Val Phe Ser Cys Ser Val Met His Glu Ala Leu His Asn His Tyr
            500                 505                 510

Thr Gln Lys Ser Leu Ser Leu Ser Pro Gly Lys
        515                 520

<210> SEQ ID NO 10
<211> LENGTH: 508
<212> TYPE: PRT
<213> ORGANISM: Artificial sequence
<220> FEATURE:
<223> OTHER INFORMATION: Format 1b

<400> SEQUENCE: 10

Glu Pro Lys Ser Ser Asp Lys Thr His Thr Ser Pro Pro Ser Pro Ala
1               5                   10                  15
```

```
Pro Glu Leu Leu Gly Gly Pro Ser Val Phe Leu Phe Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Gly Gly Ser Ser Thr Ala Ser Gly
225                 230                 235                 240

Ser Gly Ser Gly Gly Ser Gly Thr Ala Gly Ser Ser Gly Gly Ala Gly
                245                 250                 255

Ser Ser Gly Gly Ser Thr Thr Ala Gly Gly Ser Ala Ser Gly Ser Gly
            260                 265                 270

Ser Thr Gly Ser Gly Thr Gly Gly Ala Ser Ser Gly Gly Ala Ser Gly
        275                 280                 285

Ala Ser Gly Ala Pro Glu Leu Leu Gly Gly Pro Ser Val Phe Leu Phe
    290                 295                 300

Pro Pro Lys Pro Lys Asp Thr Leu Met Ile Ser Arg Thr Pro Glu Val
305                 310                 315                 320

Thr Cys Val Val Val Asp Val Ser His Glu Asp Pro Glu Val Lys Phe
                325                 330                 335

Asn Trp Tyr Val Asp Gly Val Glu Val His Asn Ala Lys Thr Lys Pro
            340                 345                 350

Arg Glu Glu Gln Tyr Asn Ser Thr Tyr Arg Val Val Ser Val Leu Thr
        355                 360                 365

Val Leu His Gln Asp Trp Leu Asn Gly Lys Glu Tyr Lys Cys Lys Val
    370                 375                 380

Ser Asn Lys Ala Leu Pro Ala Pro Ile Glu Lys Thr Ile Ser Lys Ala
385                 390                 395                 400

Lys Gly Gln Pro Arg Glu Pro Gln Val Tyr Thr Leu Pro Pro Ser Arg
                405                 410                 415

Asp Glu Leu Thr Lys Asn Gln Val Ser Leu Thr Cys Leu Val Lys Gly
            420                 425                 430

Phe Tyr Pro Ser Asp Ile Ala Val Glu Trp Glu Ser Asn Gly Gln Pro
```

```
                435                 440                 445
Glu Asn Asn Tyr Lys Thr Thr Pro Val Leu Asp Ser Asp Gly Ser
450                 455                 460

Phe Phe Leu Tyr Ser Lys Leu Thr Val Asp Lys Ser Arg Trp Gln Gln
465                 470                 475                 480

Gly Asn Val Phe Ser Cys Ser Val Met His Glu Ala Leu His Asn His
                485                 490                 495

Tyr Thr Gln Lys Ser Leu Ser Leu Ser Pro Gly Lys
            500                 505

<210> SEQ ID NO 11
<211> LENGTH: 514
<212> TYPE: PRT
<213> ORGANISM: Artificial sequence
<220> FEATURE:
<223> OTHER INFORMATION: Format 2a

<400> SEQUENCE: 11

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gly Gly
        115                 120                 125

Gly Ser Gly Gly Gly Gly Ser Gly Gly Gly Ser Gly Gly Gly Gly
    130                 135                 140

Ser Gly Gly Gly Gly Ser Glu Pro Lys Ser Cys Asp Lys Thr His Thr
145                 150                 155                 160

Cys Pro Pro Cys Pro Ala Pro Glu Leu Leu Gly Gly Pro Ser Val Phe
                165                 170                 175

Leu Phe Pro Pro Lys Pro Lys Asp Thr Leu Met Ile Ser Arg Thr Pro
            180                 185                 190

Glu Val Thr Cys Val Val Val Asp Val Ser His Glu Asp Pro Glu Val
        195                 200                 205

Lys Phe Asn Trp Tyr Val Asp Gly Val Glu Val His Asn Ala Lys Thr
210                 215                 220

Lys Pro Arg Glu Glu Gln Tyr Asn Ser Thr Tyr Arg Val Val Ser Val
225                 230                 235                 240

Leu Thr Val Leu His Gln Asp Trp Leu Asn Gly Lys Glu Tyr Lys Cys
                245                 250                 255

Lys Val Ser Asn Lys Ala Leu Pro Ala Pro Ile Glu Lys Thr Ile Ser
            260                 265                 270

Lys Ala Lys Gly Gln Pro Arg Glu Pro Gln Val Tyr Thr Leu Pro Pro
        275                 280                 285

Ser Arg Asp Glu Leu Thr Lys Asn Gln Val Ser Leu Thr Cys Leu Val
```

-continued

```
                    290                 295                 300
Lys Gly Phe Tyr Pro Ser Asp Ile Ala Val Glu Trp Glu Ser Asn Gly
305                 310                 315                 320

Gln Pro Glu Asn Asn Tyr Lys Thr Thr Pro Val Leu Asp Ser Asp
                        325                 330                 335

Gly Ser Phe Phe Leu Tyr Ser Lys Leu Thr Val Asp Lys Ser Arg Trp
                340                 345                 350

Gln Gln Gly Asn Val Phe Ser Cys Ser Val Met His Glu Ala Leu His
                355                 360                 365

Asn His Tyr Thr Gln Lys Ser Leu Ser Leu Ser Pro Gly Lys Gly Gly
            370                 375                 380

Gly Gly Ser Gly Gly Gly Ser Gly Gly Gly Ser Gly Gly
385                 390                 395                 400

Gly Ser Gly Gly Gly Ser Gly Gln Pro Arg Glu Pro Gln Val Tyr
                405                 410                 415

Thr Leu Pro Pro Ser Arg Asp Glu Leu Thr Lys Asn Gln Val Ser Leu
                420                 425                 430

Thr Cys Leu Val Lys Gly Phe Tyr Pro Ser Asp Ile Ala Val Glu Trp
            435                 440                 445

Glu Ser Asn Gly Gln Pro Glu Asn Asn Tyr Lys Thr Thr Pro Pro Val
450                 455                 460

Leu Asp Ser Asp Gly Ser Phe Phe Leu Tyr Ser Lys Leu Thr Val Asp
465                 470                 475                 480

Lys Ser Arg Trp Gln Gln Gly Asn Val Phe Ser Cys Ser Val Met His
                485                 490                 495

Glu Ala Leu His Asn His Tyr Thr Gln Lys Ser Leu Ser Leu Ser Pro
                500                 505                 510

Gly Lys

<210> SEQ ID NO 12
<211> LENGTH: 499
<212> TYPE: PRT
<213> ORGANISM: Artificial sequence
<220> FEATURE:
<223> OTHER INFORMATION: Format 2b

<400> SEQUENCE: 12

Glu Pro Lys Ser Ser Asp Lys Thr His Thr Ser Pro Pro Ser Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gly Gly
        115                 120                 125

Gly Ser Gly Gly Gly Gly Ser Gly Gly Gly Gly Ser Gly Gly Gly Gly
    130                 135                 140
```

Ser Gly Gly Gly Gly Ser Ala Pro Glu Leu Leu Gly Pro Ser Val
145                 150                 155                 160

Phe Leu Phe Pro Pro Lys Pro Lys Asp Thr Leu Met Ile Ser Arg Thr
                165                 170                 175

Pro Glu Val Thr Cys Val Val Val Asp Val Ser His Glu Asp Pro Glu
            180                 185                 190

Val Lys Phe Asn Trp Tyr Val Asp Gly Val Glu Val His Asn Ala Lys
        195                 200                 205

Thr Lys Pro Arg Glu Glu Gln Tyr Asn Ser Thr Tyr Arg Val Val Ser
210                 215                 220

Val Leu Thr Val Leu His Gln Asp Trp Leu Asn Gly Lys Glu Tyr Lys
225                 230                 235                 240

Cys Lys Val Ser Asn Lys Ala Leu Pro Ala Pro Ile Glu Lys Thr Ile
                245                 250                 255

Ser Lys Ala Lys Gly Gln Pro Arg Glu Pro Gln Val Tyr Thr Leu Pro
            260                 265                 270

Pro Ser Arg Asp Glu Leu Thr Lys Asn Gln Val Ser Leu Thr Cys Leu
        275                 280                 285

Val Lys Gly Phe Tyr Pro Ser Asp Ile Ala Val Glu Trp Glu Ser Asn
290                 295                 300

Gly Gln Pro Glu Asn Asn Tyr Lys Thr Thr Pro Pro Val Leu Asp Ser
305                 310                 315                 320

Asp Gly Ser Phe Phe Leu Tyr Ser Lys Leu Thr Val Asp Lys Ser Arg
                325                 330                 335

Trp Gln Gln Gly Asn Val Phe Ser Cys Ser Val Met His Glu Ala Leu
            340                 345                 350

His Asn His Tyr Thr Gln Lys Ser Leu Ser Leu Ser Pro Gly Lys Gly
        355                 360                 365

Gly Gly Gly Ser Gly Gly Gly Gly Ser Gly Gly Gly Gly Ser Gly Gly
370                 375                 380

Gly Gly Ser Gly Gly Gly Gly Ser Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Tyr Ser Lys Leu Thr Val
450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys

<210> SEQ ID NO 13
<211> LENGTH: 484
<212> TYPE: PRT
<213> ORGANISM: Artificial sequence
<220> FEATURE:
<223> OTHER INFORMATION: Format 2c

<400> SEQUENCE: 13

```
Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gly
            100                 105                 110

Gly Gly Ser Gly Gly Gly Gly Ser Gly Gly Gly Gly Ser Gly Gly Gly
        115                 120                 125

Gly Ser Gly Gly Gly Ser Ala Pro Glu Leu Leu Gly Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Asp Val Ser His Glu Asp Pro
            165                 170                 175

Glu Val Lys Phe Asn Trp Tyr Val Asp Gly Val Glu Val His Asn Ala
                180                 185                 190

Lys Thr Lys Pro Arg Glu Glu Gln Tyr Asn Ser Thr Tyr Arg Val Val
            195                 200                 205

Ser Val Leu Thr Val Leu His Gln Asp Trp Leu Asn Gly Lys Glu Tyr
        210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Arg Asp Glu Leu Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Asp
        290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350

Gly Gly Gly Gly Ser Gly Gly Gly Gly Ser Gly Gly Gly Gly Ser Gly
        355                 360                 365

Gly Gly Ser Gly Gly Gly Gly Ser Gly Gln Pro Arg Glu Pro Gln
    370                 375                 380

Val Tyr Thr Leu Pro Pro Ser Arg Asp Glu Leu Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
```

```
                420             425             430
Pro Val Leu Asp Ser Asp Gly Ser Phe Phe Leu Tyr Ser Lys Leu Thr
            435                 440                 445
Val Asp Lys Ser Arg Trp Gln Gln Gly Asn Val Phe Ser Cys Ser Val
            450                 455                 460
Met His Glu Ala Leu His Asn His Tyr Thr Gln Lys Ser Leu Ser Leu
465                 470                 475                 480
Ser Pro Gly Lys

<210> SEQ ID NO 14
<211> LENGTH: 98
<212> TYPE: PRT
<213> ORGANISM: Homo sapiens

<400> SEQUENCE: 14

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val

<210> SEQ ID NO 15
<211> LENGTH: 109
<212> TYPE: PRT
<213> ORGANISM: Homo sapiens

<400> SEQUENCE: 15

Ala Pro Pro Val Ala Gly Pro Ser Val Phe Leu Phe Pro Pro Lys Pro
1               5                   10                  15
Lys Asp Thr Leu Met Ile Ser Arg Thr Pro Glu Val Thr Cys Val Val
                20                  25                  30
Val Asp Val Ser His Glu Asp Pro Glu Val Gln Phe Asn Trp Tyr Val
            35                  40                  45
Asp Gly Val Glu Val His Asn Ala Lys Thr Lys Pro Arg Glu Glu Gln
        50                  55                  60
Phe Asn Ser Thr Phe Arg Val Val Ser Val Leu Thr Val Val His Gln
65                  70                  75                  80
Asp Trp Leu Asn Gly Lys Glu Tyr Lys Cys Lys Val Ser Asn Lys Gly
                85                  90                  95
Leu Pro Ala Pro Ile Glu Lys Thr Ile Ser Lys Thr Lys
            100                 105

<210> SEQ ID NO 16
<211> LENGTH: 107
<212> TYPE: PRT
<213> ORGANISM: Homo sapiens

<400> SEQUENCE: 16

Gly Gln Pro Arg Glu Pro Gln Val Tyr Thr Leu Pro Pro Ser Arg Glu
```

```
                1               5                   10                  15
            Glu Met Thr Lys Asn Gln Val Ser Leu Thr Cys Leu Val Lys Gly Phe
                            20                  25                  30

Tyr Pro Ser Asp Ile Ala Val Glu Trp Glu Ser Asn Gly Gln Pro Glu
                            35                  40                  45

Asn Asn Tyr Lys Thr Thr Pro Pro Met Leu Asp Ser Asp Gly Ser Phe
                50                      55                  60

Phe Leu Tyr Ser Lys Leu Thr Val Asp Lys Ser Arg Trp Gln Gln Gly
            65                      70                  75                  80

Asn Val Phe Ser Cys Ser Val Met His Glu Ala Leu His Asn His Tyr
                            85                  90                  95

Thr Gln Lys Ser Leu Ser Leu Ser Pro Gly Lys
                            100                 105

<210> SEQ ID NO 17
<211> LENGTH: 207
<212> TYPE: PRT
<213> ORGANISM: Artificial sequence
<220> FEATURE:
<223> OTHER INFORMATION: CH1CH2

<400> SEQUENCE: 17

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Ala Pro Pro Val Ala Gly Pro Ser Val Phe Leu Phe Pro Pro
                100                 105                 110

Lys Pro Lys Asp Thr Leu Met Ile Ser Arg Thr Pro Glu Val Thr Cys
            115                 120                 125

Val Val Val Asp Val Ser His Glu Asp Pro Glu Val Gln Phe Asn Trp
        130                 135                 140

Tyr Val Asp Gly Val Glu Val His Asn Ala Lys Thr Lys Pro Arg Glu
145                 150                 155                 160

Glu Gln Phe Asn Ser Thr Phe Arg Val Val Ser Val Leu Thr Val Val
                165                 170                 175

His Gln Asp Trp Leu Asn Gly Lys Glu Tyr Lys Cys Lys Val Ser Asn
                180                 185                 190

Lys Gly Leu Pro Ala Pro Ile Glu Lys Thr Ile Ser Lys Thr Lys
            195                 200                 205

<210> SEQ ID NO 18
<211> LENGTH: 216
<212> TYPE: PRT
<213> ORGANISM: Homo sapiens

<400> SEQUENCE: 18

Ala Pro Pro Val Ala Gly Pro Ser Val Phe Leu Phe Pro Pro Lys Pro
1               5                   10                  15
```

```
Lys Asp Thr Leu Met Ile Ser Arg Thr Pro Glu Val Thr Cys Val Val
             20                  25                  30

Val Asp Val Ser His Glu Asp Pro Glu Val Gln Phe Asn Trp Tyr Val
         35                  40                  45

Asp Gly Val Glu Val His Asn Ala Lys Thr Lys Pro Arg Glu Glu Gln
 50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                 85                  90                  95

Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Thr Cys Leu Val Lys Gly Phe Tyr Pro Ser
130                 135                 140

Asp Ile Ala Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215

<210> SEQ ID NO 19
<211> LENGTH: 314
<212> TYPE: PRT
<213> ORGANISM: Artificial sequence
<220> FEATURE:
<223> OTHER INFORMATION: CH1CH2CH3

<400> SEQUENCE: 19

Ala Ser Thr Lys Gly Pro Ser Val Phe Pro Leu Ala Pro Cys Ser Arg
1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                 85                  90                  95

Thr Val Ala Pro Pro Val Ala Gly Pro Ser Val Phe Leu Phe Pro Pro
            100                 105                 110

Lys Pro Lys Asp Thr Leu Met Ile Ser Arg Thr Pro Glu Val Thr Cys
        115                 120                 125

Val Val Val Asp Val Ser His Glu Asp Pro Glu Val Gln Phe Asn Trp
130                 135                 140

Tyr Val Asp Gly Val Glu Val His Asn Ala Lys Thr Lys Pro Arg Glu
145                 150                 155                 160
```

```
Glu Gln Phe Asn Ser Thr Phe Arg Val Val Ser Val Leu Thr Val Val
                165                 170                 175

His Gln Asp Trp Leu Asn Gly Lys Glu Tyr Lys Cys Lys Val Ser Asn
            180                 185                 190

Lys Gly Leu Pro Ala Pro Ile Glu Lys Thr Ile Ser Lys Thr Lys Gly
        195                 200                 205

Gln Pro Arg Glu Pro Gln Val Tyr Thr Leu Pro Pro Ser Arg Glu Glu
    210                 215                 220

Met Thr Lys Asn Gln Val Ser Leu Thr Cys Leu Val Lys Gly Phe Tyr
225                 230                 235                 240

Pro Ser Asp Ile Ala Val Glu Trp Glu Ser Asn Gly Gln Pro Glu Asn
                245                 250                 255

Asn Tyr Lys Thr Thr Pro Pro Met Leu Asp Ser Asp Gly Ser Phe Phe
            260                 265                 270

Leu Tyr Ser Lys Leu Thr Val Asp Lys Ser Arg Trp Gln Gln Gly Asn
        275                 280                 285

Val Phe Ser Cys Ser Val Met His Glu Ala Leu His Asn His Tyr Thr
    290                 295                 300

Gln Lys Ser Leu Ser Leu Ser Pro Gly Lys
305                 310

<210> SEQ ID NO 20
<211> LENGTH: 326
<212> TYPE: PRT
<213> ORGANISM: Homo sapiens

<400> SEQUENCE: 20

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
```

```
            210                 215                 220
Pro Gln Val Tyr Thr Leu Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
                275                 280                 285

Leu Thr Val Asp Lys Ser Arg Trp Gln Gln Gly Asn Val Phe Ser Cys
                290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 21
<211> LENGTH: 491
<212> TYPE: PRT
<213> ORGANISM: Artificial sequence
<220> FEATURE:
<223> OTHER INFORMATION: Format 1c

<400> SEQUENCE: 21

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
                20                  25                  30

Val Asp Val Ser His Glu Asp Pro Glu Val Gln Phe Asn Trp Tyr Val
            35                  40                  45

Asp Gly Val Glu Val His Asn Ala Lys Thr Lys Pro Arg Glu Glu Gln
        50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys Gly Gln Pro
                100                 105                 110

Arg Glu Pro Gln Val Tyr Thr Leu Pro Pro Ser Arg Glu Glu Met Thr
            115                 120                 125

Lys Asn Gln Val Ser Leu Thr Cys Leu Val Lys Gly Phe Tyr Pro Ser
130                 135                 140

Asp Ile Ala Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
                180                 185                 190

Ser Cys Ser Val Met His Glu Ala Leu His Asn His Tyr Thr Gln Lys
            195                 200                 205

Ser Leu Ser Leu Ser Pro Gly Lys Gly Gly Ser Thr Ala Ser Gly
        210                 215                 220

Ser Gly Ser Gly Gly Ser Gly Thr Ala Gly Ser Ser Gly Gly Ala Gly
225                 230                 235                 240

Ser Ser Gly Gly Ser Thr Thr Ala Gly Gly Ser Ala Ser Gly Ser Gly
```

```
                245                 250                 255
Ser Thr Gly Ser Gly Thr Gly Gly Ala Ser Ser Gly Gly Ala Ser Gly
            260                 265                 270

Ala Ser Gly Ala Pro Pro Val Ala Gly Pro Ser Val Phe Leu Phe Pro
            275                 280                 285

Pro Lys Pro Lys Asp Thr Leu Met Ile Ser Arg Thr Pro Glu Val Thr
290                 295                 300

Cys Val Val Val Asp Val Ser His Glu Asp Pro Glu Val Gln Phe Asn
305                 310                 315                 320

Trp Tyr Val Asp Gly Val Glu Val His Asn Ala Lys Thr Lys Pro Arg
                325                 330                 335

Glu Glu Gln Phe Asn Ser Thr Phe Arg Val Val Ser Val Leu Thr Val
            340                 345                 350

Val His Gln Asp Trp Leu Asn Gly Lys Glu Tyr Lys Cys Lys Val Ser
            355                 360                 365

Asn Lys Gly Leu Pro Ala Pro Ile Glu Lys Thr Ile Ser Lys Thr Lys
        370                 375                 380

Gly Gln Pro Arg Glu Pro Gln Val Tyr Thr Leu Pro Pro Ser Arg Glu
385                 390                 395                 400

Glu Met Thr Lys Asn Gln Val Ser Leu Thr Cys Leu Val Lys Gly Phe
                405                 410                 415

Tyr Pro Ser Asp Ile Ala Val Glu Trp Glu Ser Asn Gly Gln Pro Glu
            420                 425                 430

Asn Asn Tyr Lys Thr Thr Pro Pro Met Leu Asp Ser Asp Gly Ser Phe
            435                 440                 445

Phe Leu Tyr Ser Lys Leu Thr Val Asp Lys Ser Arg Trp Gln Gln Gly
        450                 455                 460

Asn Val Phe Ser Cys Ser Val Met His Glu Ala Leu His Asn His Tyr
465                 470                 475                 480

Thr Gln Lys Ser Leu Ser Leu Ser Pro Gly Lys
                485                 490

<210> SEQ ID NO 22
<211> LENGTH: 515
<212> TYPE: PRT
<213> ORGANISM: Artificial sequence
<220> FEATURE:
<223> OTHER INFORMATION: Format 1a

<400> SEQUENCE: 22

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
```

```
            115                 120                 125
Val Tyr Thr Leu Pro Pro Ser Arg Glu Glu Met Thr Lys Asn Gln Val
            130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                    165                 170                 175

Pro Met Leu Asp Ser Asp Gly Ser Phe Phe Leu Tyr Ser Lys Leu Thr
                180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
            210                 215                 220

Ser Pro Gly Lys Gly Gly Ser Ser Thr Ala Ser Gly Ser Gly Ser Gly
225                 230                 235                 240

Gly Ser Gly Thr Ala Gly Ser Ser Gly Ala Gly Ser Ser Gly Gly
                    245                 250                 255

Ser Thr Thr Ala Gly Gly Ser Ala Ser Gly Ser Gly Ser Thr Gly Ser
                    260                 265                 270

Gly Thr Gly Gly Ala Ser Ser Gly Gly Ala Ser Gly Ala Ser Gly Glu
                    275                 280                 285

Arg Lys Cys Cys Val Glu Cys Pro Pro Cys Pro Ala Pro Pro Val Ala
            290                 295                 300

Gly Pro Ser Val Phe Leu Phe Pro Pro Lys Pro Lys Asp Thr Leu Met
305                 310                 315                 320

Ile Ser Arg Thr Pro Glu Val Thr Cys Val Val Asp Val Ser His
                    325                 330                 335

Glu Asp Pro Glu Val Gln Phe Asn Trp Tyr Val Asp Gly Val Glu Val
                340                 345                 350

His Asn Ala Lys Thr Lys Pro Arg Glu Glu Gln Phe Asn Ser Thr Phe
            355                 360                 365

Arg Val Val Ser Val Leu Thr Val Val His Gln Asp Trp Leu Asn Gly
            370                 375                 380

Lys Glu Tyr Lys Cys Lys Val Ser Asn Lys Gly Leu Pro Ala Pro Ile
385                 390                 395                 400

Glu Lys Thr Ile Ser Lys Thr Lys Gly Gln Pro Arg Glu Pro Gln Val
                    405                 410                 415

Tyr Thr Leu Pro Pro Ser Arg Glu Glu Met Thr Lys Asn Gln Val Ser
                420                 425                 430

Leu Thr Cys Leu Val Lys Gly Phe Tyr Pro Ser Asp Ile Ala Val Glu
            435                 440                 445

Trp Glu Ser Asn Gly Gln Pro Glu Asn Asn Tyr Lys Thr Thr Pro Pro
            450                 455                 460

Met Leu Asp Ser Asp Gly Ser Phe Phe Leu Tyr Ser Lys Leu Thr Val
465                 470                 475                 480

Asp Lys Ser Arg Trp Gln Gln Gly Asn Val Phe Ser Cys Ser Val Met
                    485                 490                 495

His Glu Ala Leu His Asn His Tyr Thr Gln Lys Ser Leu Ser Leu Ser
                500                 505                 510

Pro Gly Lys
        515

<210> SEQ ID NO 23
```

<211> LENGTH: 503
<212> TYPE: PRT
<213> ORGANISM: Artificial sequence
<220> FEATURE:
<223> OTHER INFORMATION: Format 1b

<400> SEQUENCE: 23

```
Glu Arg Lys Ser Ser Val Glu Ser Pro Ser Ala Pro Pro Val
1               5                   10                  15
Ala Gly Pro Ser Val Phe Leu Phe Pro Pro Lys Pro Lys Asp Thr Leu
            20                  25                  30
Met Ile Ser Arg Thr Pro Glu Val Thr Cys Val Val Val Asp Val Ser
        35                  40                  45
His Glu Asp Pro Glu Val Gln Phe Asn Trp Tyr Val Asp Gly Val Glu
    50                  55                  60
Val His Asn Ala Lys Thr Lys Pro Arg Glu Glu Gln Phe Asn Ser Thr
65                  70                  75                  80
Phe Arg Val Val Ser Val Leu Thr Val Val His Gln Asp Trp Leu Asn
                85                  90                  95
Gly Lys Glu Tyr Lys Cys Lys Val Ser Asn Lys Gly Leu Pro Ala Pro
            100                 105                 110
Ile Glu Lys Thr Ile Ser Lys Thr Lys Gly Gln Pro Arg Glu Pro Gln
        115                 120                 125
Val Tyr Thr Leu Pro Pro Ser Arg Glu Glu Met Thr Lys Asn Gln Val
    130                 135                 140
Ser Leu Thr Cys Leu Val Lys Gly Phe Tyr Pro Ser Asp Ile Ala Val
145                 150                 155                 160
Glu Trp Glu Ser Asn Gly Gln Pro Glu Asn Asn Tyr Lys Thr Thr Pro
                165                 170                 175
Pro Met Leu Asp Ser Asp Gly Ser Phe Phe Leu Tyr Ser Lys Leu Thr
            180                 185                 190
Val Asp Lys Ser Arg Trp Gln Gln Gly Asn Val Phe Ser Cys Ser Val
        195                 200                 205
Met His Glu Ala Leu His Asn His Tyr Thr Gln Lys Ser Leu Ser Leu
    210                 215                 220
Ser Pro Gly Lys Gly Gly Ser Ser Thr Ala Ser Gly Ser Gly Ser Gly
225                 230                 235                 240
Gly Ser Gly Thr Ala Gly Ser Gly Gly Ala Gly Ser Ser Gly Gly
                245                 250                 255
Ser Thr Thr Ala Gly Gly Ser Ala Ser Gly Ser Gly Ser Thr Gly Ser
            260                 265                 270
Gly Thr Gly Gly Ala Ser Ser Gly Gly Ala Ser Gly Ala Ser Gly Ala
        275                 280                 285
Pro Pro Val Ala Gly Pro Ser Val Phe Leu Phe Pro Pro Lys Pro Lys
    290                 295                 300
Asp Thr Leu Met Ile Ser Arg Thr Pro Glu Val Thr Cys Val Val Val
305                 310                 315                 320
Asp Val Ser His Glu Asp Pro Glu Val Gln Phe Asn Trp Tyr Val Asp
                325                 330                 335
Gly Val Glu Val His Asn Ala Lys Thr Lys Pro Arg Glu Glu Gln Phe
            340                 345                 350
Asn Ser Thr Phe Arg Val Val Ser Val Leu Thr Val Val His Gln Asp
        355                 360                 365
Trp Leu Asn Gly Lys Glu Tyr Lys Cys Lys Val Ser Asn Lys Gly Leu
    370                 375                 380
```

```
Pro Ala Pro Ile Glu Lys Thr Ile Ser Lys Thr Lys Gly Gln Pro Arg
385                 390                 395                 400

Glu Pro Gln Val Tyr Thr Leu Pro Pro Ser Arg Glu Met Thr Lys
            405                 410                 415

Asn Gln Val Ser Leu Thr Cys Leu Val Lys Gly Phe Tyr Pro Ser Asp
            420                 425                 430

Ile Ala Val Glu Trp Glu Ser Asn Gly Gln Pro Glu Asn Asn Tyr Lys
            435                 440                 445

Thr Thr Pro Pro Met Leu Asp Ser Asp Gly Ser Phe Phe Leu Tyr Ser
            450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Pro Gly Lys
                500

<210> SEQ ID NO 24
<211> LENGTH: 506
<212> TYPE: PRT
<213> ORGANISM: Artificial sequence
<220> FEATURE:
<223> OTHER INFORMATION: Format 2a

<400> SEQUENCE: 24

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
            35                  40                  45

His Glu Asp Pro Glu Val Gln Phe Asn Trp Tyr Val Asp Gly Val Glu
        50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gly Gly Ser Gly Gly Gly
            115                 120                 125

Gly Gly Ser Gly Gly Gly Gly Ser Gly Gly Gly Gly Ser Gly Gly Gly
        130                 135                 140

Gly Ser Glu Arg Lys Cys Cys Val Glu Cys Pro Pro Cys Pro Ala Pro
145                 150                 155                 160

Pro Val Ala Gly Pro Ser Val Phe Leu Phe Pro Pro Lys Pro Lys Asp
                165                 170                 175

Thr Leu Met Ile Ser Arg Thr Pro Glu Val Thr Cys Val Val Val Asp
            180                 185                 190

Val Ser His Glu Asp Pro Glu Val Gln Phe Asn Trp Tyr Val Asp Gly
        195                 200                 205

Val Glu Val His Asn Ala Lys Thr Lys Pro Arg Glu Glu Gln Phe Asn
    210                 215                 220

Ser Thr Phe Arg Val Val Ser Val Leu Thr Val Val His Gln Asp Trp
225                 230                 235                 240
```

```
Leu Asn Gly Lys Glu Tyr Lys Cys Lys Val Ser Asn Lys Gly Leu Pro
                245                 250                 255

Ala Pro Ile Glu Lys Thr Ile Ser Lys Thr Lys Gly Gln Pro Arg Glu
            260                 265                 270

Pro Gln Val Tyr Thr Leu Pro Pro Ser Arg Glu Glu Met Thr Lys Asn
        275                 280                 285

Gln Val Ser Leu Thr Cys Leu Val Lys Gly Phe Tyr Pro Ser Asp Ile
    290                 295                 300

Ala Val Glu Trp Glu Ser Asn Gly Gln Pro Glu Asn Asn Tyr Lys Thr
305                 310                 315                 320

Thr Pro Pro Met Leu Asp Ser Asp Gly Ser Phe Phe Leu Tyr Ser Lys
                325                 330                 335

Leu Thr Val Asp Lys Ser Arg Trp Gln Gln Gly Asn Val Phe Ser Cys
            340                 345                 350

Ser Val Met His Glu Ala Leu His Asn His Tyr Thr Gln Lys Ser Leu
        355                 360                 365

Ser Leu Ser Pro Gly Lys Gly Gly Gly Ser Gly Gly Gly Ser
    370                 375                 380

Gly Gly Gly Gly Ser Gly Gly Gly Ser Gly Gly Gly Ser Gly
385                 390                 395                 400

Gln Pro Arg Glu Pro Gln Val Tyr Thr Leu Pro Pro Ser Arg Glu Glu
                405                 410                 415

Met Thr Lys Asn Gln Val Ser Leu Thr Cys Leu Val Lys Gly Phe Tyr
            420                 425                 430

Pro Ser Asp Ile Ala Val Glu Trp Glu Ser Asn Gly Gln Pro Glu Asn
        435                 440                 445

Asn Tyr Lys Thr Thr Pro Pro Met Leu Asp Ser Asp Gly Ser Phe Phe
    450                 455                 460

Leu Tyr Ser Lys Leu Thr Val Asp Lys Ser Arg Trp Gln Gln Gly Asn
465                 470                 475                 480

Val Phe Ser Cys Ser Val Met His Glu Ala Leu His Asn His Tyr Thr
                485                 490                 495

Gln Lys Ser Leu Ser Leu Ser Pro Gly Lys
            500                 505

<210> SEQ ID NO 25
<211> LENGTH: 494
<212> TYPE: PRT
<213> ORGANISM: Artificial sequence
<220> FEATURE:
<223> OTHER INFORMATION: Format 2b

<400> SEQUENCE: 25

Glu Arg Lys Ser Ser Val Glu Ser Pro Pro Ser Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95
```

```
Gly Lys Glu Tyr Lys Cys Lys Val Ser Asn Lys Gly Leu Pro Ala Pro
                100                 105                 110

Ile Glu Lys Thr Ile Ser Lys Thr Lys Gly Gly Gly Ser Gly Gly
            115                 120                 125

Gly Gly Ser Gly Gly Gly Ser Gly Gly Gly Ser Gly Gly Gly
    130                 135                 140

Gly Ser Ala Pro Pro Val Ala Gly Pro Ser Val Phe Leu Phe Pro
145                 150                 155                 160

Lys Pro Lys Asp Thr Leu Met Ile Ser Arg Thr Pro Glu Val Thr Cys
                165                 170                 175

Val Val Val Asp Val Ser His Glu Asp Pro Glu Val Gln Phe Asn Trp
            180                 185                 190

Tyr Val Asp Gly Val Glu Val His Asn Ala Lys Thr Lys Pro Arg Glu
        195                 200                 205

Glu Gln Phe Asn Ser Thr Phe Arg Val Val Ser Val Leu Thr Val Val
    210                 215                 220

His Gln Asp Trp Leu Asn Gly Lys Glu Tyr Lys Cys Lys Val Ser Asn
225                 230                 235                 240

Lys Gly Leu Pro Ala Pro Ile Glu Lys Thr Ile Ser Lys Thr Lys Gly
                245                 250                 255

Gln Pro Arg Glu Pro Gln Val Tyr Thr Leu Pro Pro Ser Arg Glu Glu
            260                 265                 270

Met Thr Lys Asn Gln Val Ser Leu Thr Cys Leu Val Lys Gly Phe Tyr
        275                 280                 285

Pro Ser Asp Ile Ala Val Glu Trp Glu Ser Asn Gly Gln Pro Glu Asn
    290                 295                 300

Asn Tyr Lys Thr Thr Pro Pro Met Leu Asp Ser Asp Gly Ser Phe Phe
305                 310                 315                 320

Leu Tyr Ser Lys Leu Thr Val Asp Lys Ser Arg Trp Gln Gln Gly Asn
                325                 330                 335

Val Phe Ser Cys Ser Val Met His Glu Ala Leu His Asn His Tyr Thr
            340                 345                 350

Gln Lys Ser Leu Ser Leu Ser Pro Gly Lys Gly Gly Gly Ser Gly
        355                 360                 365

Gly Gly Gly Ser Gly Gly Gly Gly Ser Gly Gly Gly Ser Gly Gly
    370                 375                 380

Gly Gly Ser Gly Gln Pro Arg Glu Pro Gln Val Tyr Thr Leu Pro Pro
385                 390                 395                 400

Ser Arg Glu Glu Met Thr Lys Asn Gln Val Ser Leu Thr Cys Leu Val
                405                 410                 415

Lys Gly Phe Tyr Pro Ser Asp Ile Ala Val Glu Trp Glu Ser Asn Gly
            420                 425                 430

Gln Pro Glu Asn Asn Tyr Lys Thr Thr Pro Pro Met Leu Asp Ser Asp
        435                 440                 445

Gly Ser Phe Phe Leu Tyr Ser Lys Leu Thr Val Asp Lys Ser Arg Trp
    450                 455                 460

Gln Gln Gly Asn Val Phe Ser Cys Ser Val Met His Glu Ala Leu His
465                 470                 475                 480

Asn His Tyr Thr Gln Lys Ser Leu Ser Leu Ser Pro Gly Lys
                485                 490

<210> SEQ ID NO 26
<211> LENGTH: 482
```

```
<212> TYPE: PRT
<213> ORGANISM: Artificial sequence
<220> FEATURE:
<223> OTHER INFORMATION: Format 2c

<400> SEQUENCE: 26

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys Gly Gly Gly
            100                 105                 110

Gly Ser Gly Gly Gly Gly Ser Gly Gly Gly Gly Ser Gly Gly Gly Gly
            115                 120                 125

Ser Gly Gly Gly Gly Ser Ala Pro Pro Val Ala Gly Pro Ser Val Phe
        130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Gln Phe Asn Trp Tyr Val Asp Gly Val Glu Val His Asn Ala Lys Thr
            180                 185                 190

Lys Pro Arg Glu Glu Gln Phe Asn Ser Thr Phe Arg Val Val Ser Val
        195                 200                 205

Leu Thr Val Val His Gln Asp Trp Leu Asn Gly Lys Glu Tyr Lys Cys
    210                 215                 220

Lys Val Ser Asn Lys Gly Leu Pro Ala Pro Ile Glu Lys Thr Ile Ser
225                 230                 235                 240

Lys Thr Lys Gly Gln Pro Arg Glu Pro Gln Val Tyr Thr Leu Pro Pro
                245                 250                 255

Ser Arg Glu Glu Met Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Met Leu Asp Ser Asp
    290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys Gly Gly
            340                 345                 350

Gly Gly Ser Gly Gly Gly Gly Ser Gly Gly Gly Gly Ser Gly Gly Gly
        355                 360                 365

Gly Ser Gly Gly Gly Gly Ser Gly Gln Pro Arg Glu Pro Gln Val Tyr
    370                 375                 380
```

```
Thr Leu Pro Pro Ser Arg Glu Glu Met Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Met
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
450                 455                 460

Glu Ala Leu His Asn His Tyr Thr Gln Lys Ser Leu Ser Leu Ser Pro
465                 470                 475                 480

Gly Lys

<210> SEQ ID NO 27
<211> LENGTH: 98
<212> TYPE: PRT
<213> ORGANISM: Homo sapiens

<400> SEQUENCE: 27

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val

<210> SEQ ID NO 28
<211> LENGTH: 110
<212> TYPE: PRT
<213> ORGANISM: Homo sapiens

<400> SEQUENCE: 28

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys
            100                 105                 110

<210> SEQ ID NO 29
```

<211> LENGTH: 107
<212> TYPE: PRT
<213> ORGANISM: Homo sapiens

<400> SEQUENCE: 29

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Gly Gln Pro Glu
        35                  40                  45

Asn Asn Tyr Asn Thr Thr Pro Pro Met Leu Asp Ser Asp Gly Ser Phe
50                  55                  60

Phe Leu Tyr Ser Lys Leu Thr Val Asp Lys Ser Arg Trp Gln Gln Gly
65                  70                  75                  80

Asn Ile Phe Ser Cys Ser Val Met His Glu Ala Leu His Asn Arg Phe
                85                  90                  95

Thr Gln Lys Ser Leu Ser Leu Ser Pro Gly Lys
            100                 105

<210> SEQ ID NO 30
<211> LENGTH: 208
<212> TYPE: PRT
<213> ORGANISM: Artificial sequence
<220> FEATURE:
<223> OTHER INFORMATION: CH1CH2

<400> SEQUENCE: 30

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Ala Pro Glu Leu Leu Gly Gly Pro Ser Val Phe Leu Phe Pro
            100                 105                 110

Pro Lys Pro Lys Asp Thr Leu Met Ile Ser Arg Thr Pro Glu Val Thr
        115                 120                 125

Cys Val Val Val Asp Val Ser His Glu Asp Pro Glu Val Gln Phe Lys
130                 135                 140

Trp Tyr Val Asp Gly Val Glu Val His Asn Ala Lys Thr Lys Pro Arg
145                 150                 155                 160

Glu Glu Gln Tyr Asn Ser Thr Phe Arg Val Val Ser Val Leu Thr Val
                165                 170                 175

Leu His Gln Asp Trp Leu Asn Gly Lys Glu Tyr Lys Cys Lys Val Ser
            180                 185                 190

Asn Lys Ala Leu Pro Ala Pro Ile Glu Lys Thr Ile Ser Lys Thr Lys
        195                 200                 205

<210> SEQ ID NO 31
<211> LENGTH: 217

-continued

```
<212> TYPE: PRT
<213> ORGANISM: Homo sapiens

<400> SEQUENCE: 31

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Ser Gly Gln Pro Glu Asn Asn
145                 150                 155                 160

Tyr Asn Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Ile
            180                 185                 190

Phe Ser Cys Ser Val Met His Glu Ala Leu His Asn Arg Phe Thr Gln
        195                 200                 205

Lys Ser Leu Ser Leu Ser Pro Gly Lys
    210                 215

<210> SEQ ID NO 32
<211> LENGTH: 315
<212> TYPE: PRT
<213> ORGANISM: Artificial sequence
<220> FEATURE:
<223> OTHER INFORMATION: CH1CH2CH3

<400> SEQUENCE: 32

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Ala Pro Glu Leu Leu Gly Gly Pro Ser Val Phe Leu Phe Pro
            100                 105                 110

Pro Lys Pro Lys Asp Thr Leu Met Ile Ser Arg Thr Pro Glu Val Thr
```

```
              115                 120                 125
Cys Val Val Asp Val Ser His Glu Asp Pro Glu Val Gln Phe Lys
    130                 135                 140

Trp Tyr Val Asp Gly Val Glu Val His Asn Ala Lys Thr Lys Pro Arg
145                 150                 155                 160

Glu Glu Gln Tyr Asn Ser Thr Phe Arg Val Val Ser Val Leu Thr Val
                165                 170                 175

Leu His Gln Asp Trp Leu Asn Gly Lys Glu Tyr Lys Cys Lys Val Ser
                180                 185                 190

Asn Lys Ala Leu Pro Ala Pro Ile Glu Lys Thr Ile Ser Lys Thr Lys
                195                 200                 205

Gly Gln Pro Arg Glu Pro Gln Val Tyr Thr Leu Pro Pro Ser Arg Glu
    210                 215                 220

Glu Met Thr Lys Asn Gln Val Ser Leu Thr Cys Leu Val Lys Gly Phe
225                 230                 235                 240

Tyr Pro Ser Asp Ile Ala Val Glu Trp Glu Ser Ser Gly Gln Pro Glu
                245                 250                 255

Asn Asn Tyr Asn Thr Thr Pro Pro Met Leu Asp Ser Asp Gly Ser Phe
                260                 265                 270

Phe Leu Tyr Ser Lys Leu Thr Val Asp Lys Ser Arg Trp Gln Gln Gly
                275                 280                 285

Asn Ile Phe Ser Cys Ser Val Met His Glu Ala Leu His Asn Arg Phe
                290                 295                 300

Thr Gln Lys Ser Leu Ser Leu Ser Pro Gly Lys
305                 310                 315

<210> SEQ ID NO 33
<211> LENGTH: 377
<212> TYPE: PRT
<213> ORGANISM: Homo sapiens

<400> SEQUENCE: 33

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
                100                 105                 110

Arg Cys Pro Glu Pro Lys Ser Cys Asp Thr Pro Pro Cys Pro Arg
                115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175
```

-continued

```
Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 34
<211> LENGTH: 493
<212> TYPE: PRT
<213> ORGANISM: Artificial sequence
<220> FEATURE:
<223> OTHER INFORMATION: Format 1c

<400> SEQUENCE: 34

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Ser Gly Gln Pro Glu Asn Asn
145                 150                 155                 160
```

Tyr Asn Thr Thr Pro Pro Met Leu Asp Ser Asp Gly Ser Phe Phe Leu
            165                 170                 175

Tyr Ser Lys Leu Thr Val Asp Lys Ser Arg Trp Gln Gln Gly Asn Ile
        180                 185                 190

Phe Ser Cys Ser Val Met His Glu Ala Leu His Asn Arg Phe Thr Gln
        195                 200                 205

Lys Ser Leu Ser Leu Ser Pro Gly Lys Gly Gly Ser Ser Thr Ala Ser
    210                 215                 220

Gly Ser Gly Ser Gly Ser Gly Thr Ala Gly Ser Ser Gly Gly Ala
225                 230                 235                 240

Gly Ser Ser Gly Gly Ser Thr Thr Ala Gly Gly Ser Ala Ser Gly Ser
                245                 250                 255

Gly Ser Thr Gly Ser Gly Thr Gly Gly Ala Ser Ser Gly Gly Ala Ser
            260                 265                 270

Gly Ala Ser Gly Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
        290                 295                 300

Val Thr Cys Val Val Val Asp Val Ser His Glu Asp Pro Glu Val Gln
305                 310                 315                 320

Phe Lys Trp Tyr Val Asp Gly Val Glu Val His Asn Ala Lys Thr Lys
                325                 330                 335

Pro Arg Glu Glu Gln Tyr Asn Ser Thr Phe Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
    370                 375                 380

Thr Lys Gly Gln Pro Arg Glu Pro Gln Val Tyr Thr Leu Pro Pro Ser
385                 390                 395                 400

Arg Glu Glu Met Thr Lys Asn Gln Val Ser Leu Thr Cys Leu Val Lys
                405                 410                 415

Gly Phe Tyr Pro Ser Asp Ile Ala Val Glu Trp Glu Ser Ser Gly Gln
            420                 425                 430

Pro Glu Asn Asn Tyr Asn Thr Thr Pro Pro Met Leu Asp Ser Asp Gly
        435                 440                 445

Ser Phe Phe Leu Tyr Ser Lys Leu Thr Val Asp Lys Ser Arg Trp Gln
    450                 455                 460

Gln Gly Asn Ile Phe Ser Cys Ser Val Met His Glu Ala Leu His Asn
465                 470                 475                 480

Arg Phe Thr Gln Lys Ser Leu Ser Leu Ser Pro Gly Lys
                485                 490

<210> SEQ ID NO 35
<211> LENGTH: 617
<212> TYPE: PRT
<213> ORGANISM: Artificial sequence
<220> FEATURE:
<223> OTHER INFORMATION: Format 1a

<400> SEQUENCE: 35

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

-continued

```
Glu Pro Lys Ser Cys Asp Thr Pro Pro Cys Pro Arg Cys Pro Glu
            35                  40                  45
Pro Lys Ser Cys Asp Thr Pro Pro Cys Pro Arg Cys Pro Ala Pro
     50                  55                  60
Glu Leu Leu Gly Gly Pro Ser Val Phe Leu Phe Pro Pro Lys Pro Lys
65                   70                  75                  80
Asp Thr Leu Met Ile Ser Arg Thr Pro Glu Val Thr Cys Val Val Val
                 85                  90                  95
Asp Val Ser His Glu Asp Pro Glu Val Gln Phe Lys Trp Tyr Val Asp
             100                 105                 110
Gly Val Glu Val His Asn Ala Lys Thr Lys Pro Arg Glu Glu Gln Tyr
         115                 120                 125
Asn Ser Thr Phe Arg Val Val Ser Val Leu Thr Val Leu His Gln Asp
     130                 135                 140
Trp Leu Asn Gly Lys Glu Tyr Lys Cys Lys Val Ser Asn Lys Ala Leu
145                 150                 155                 160
Pro Ala Pro Ile Glu Lys Thr Ile Ser Lys Thr Lys Gly Gln Pro Arg
                 165                 170                 175
Glu Pro Gln Val Tyr Thr Leu Pro Pro Ser Arg Glu Glu Met Thr Lys
             180                 185                 190
Asn Gln Val Ser Leu Thr Cys Leu Val Lys Gly Phe Tyr Pro Ser Asp
         195                 200                 205
Ile Ala Val Glu Trp Glu Ser Ser Gly Gln Pro Glu Asn Asn Tyr Asn
     210                 215                 220
Thr Thr Pro Pro Met Leu Asp Ser Asp Gly Ser Phe Phe Leu Tyr Ser
225                 230                 235                 240
Lys Leu Thr Val Asp Lys Ser Arg Trp Gln Gln Gly Asn Ile Phe Ser
                 245                 250                 255
Cys Ser Val Met His Glu Ala Leu His Asn Arg Phe Thr Gln Lys Ser
             260                 265                 270
Leu Ser Leu Ser Pro Gly Lys Gly Gly Ser Ser Thr Ala Ser Gly Ser
         275                 280                 285
Gly Ser Gly Gly Ser Gly Thr Ala Gly Ser Ser Gly Gly Ala Gly Ser
     290                 295                 300
Ser Gly Gly Ser Thr Thr Ala Gly Gly Ser Ala Ser Gly Ser Gly Ser
305                 310                 315                 320
Thr Gly Ser Gly Thr Gly Gly Ala Ser Ser Gly Gly Ala Ser Gly Ala
                 325                 330                 335
Ser Gly Glu Leu Lys Thr Pro Leu Gly Asp Thr Thr His Thr Cys Pro
             340                 345                 350
Arg Cys Pro Glu Pro Lys Ser Cys Asp Thr Pro Pro Cys Pro Arg
         355                 360                 365
Cys Pro Glu Pro Lys Ser Cys Asp Thr Pro Pro Cys Pro Arg Cys
     370                 375                 380
Pro Glu Pro Lys Ser Cys Asp Thr Pro Pro Cys Pro Arg Cys Pro
385                 390                 395                 400
Ala Pro Glu Leu Leu Gly Gly Pro Ser Val Phe Leu Phe Pro Pro Lys
                 405                 410                 415
Pro Lys Asp Thr Leu Met Ile Ser Arg Thr Pro Glu Val Thr Cys Val
             420                 425                 430
Val Val Asp Val Ser His Glu Asp Pro Glu Val Gln Phe Lys Trp Tyr
         435                 440                 445
Val Asp Gly Val Glu Val His Asn Ala Lys Thr Lys Pro Arg Glu Glu
```

```
                   450                 455                 460

Gln Tyr Asn Ser Thr Phe Arg Val Val Ser Val Leu Thr Val Leu His
465                 470                 475                 480

Gln Asp Trp Leu Asn Gly Lys Glu Tyr Lys Cys Lys Val Ser Asn Lys
                    485                 490                 495

Ala Leu Pro Ala Pro Ile Glu Lys Thr Ile Ser Lys Thr Lys Gly Gln
                500                 505                 510

Pro Arg Glu Pro Gln Val Tyr Thr Leu Pro Pro Ser Arg Glu Glu Met
            515                 520                 525

Thr Lys Asn Gln Val Ser Leu Thr Cys Leu Val Lys Gly Phe Tyr Pro
530                 535                 540

Ser Asp Ile Ala Val Glu Trp Glu Ser Ser Gly Gln Pro Glu Asn Asn
545                 550                 555                 560

Tyr Asn Thr Thr Pro Pro Met Leu Asp Ser Asp Gly Ser Phe Phe Leu
                565                 570                 575

Tyr Ser Lys Leu Thr Val Asp Lys Ser Arg Trp Gln Gln Gly Asn Ile
            580                 585                 590

Phe Ser Cys Ser Val Met His Glu Ala Leu His Asn Arg Phe Thr Gln
        595                 600                 605

Lys Ser Leu Ser Leu Ser Pro Gly Lys
    610                 615

<210> SEQ ID NO 36
<211> LENGTH: 555
<212> TYPE: PRT
<213> ORGANISM: Artificial sequence
<220> FEATURE:
<223> OTHER INFORMATION: Format 1b

<400> SEQUENCE: 36

Glu Leu Lys Thr Pro Leu Gly Asp Thr Thr His Thr Ser Pro Arg Ser
1               5                   10                  15

Pro Glu Pro Lys Ser Ser Asp Thr Pro Pro Ser Pro Arg Ser Pro
                20                  25                  30

Glu Pro Lys Ser Ser Asp Thr Pro Pro Ser Pro Arg Ser Pro Glu
            35                  40                  45

Pro Lys Ser Ser Asp Thr Pro Pro Ser Pro Arg Ser Pro Ala Pro
        50                  55                  60

Glu Leu Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
            100                 105                 110

Gly Val Glu Val His Asn Ala Lys Thr Lys Pro Arg Glu Glu Gln Tyr
        115                 120                 125

Asn Ser Thr Phe Arg Val Val Ser Val Leu Thr Val Leu His Gln Asp
    130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
```

```
                195                 200                 205
Ile Ala Val Glu Trp Glu Ser Ser Gly Gln Pro Glu Asn Asn Tyr Asn
210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
            260                 265                 270

Leu Ser Leu Ser Pro Gly Lys Gly Gly Ser Ser Thr Ala Ser Gly Ser
        275                 280                 285

Gly Ser Gly Gly Ser Gly Thr Ala Gly Ser Ser Gly Gly Ala Gly Ser
    290                 295                 300

Ser Gly Gly Ser Thr Thr Ala Gly Gly Ser Ala Ser Gly Ser Gly Ser
305                 310                 315                 320

Thr Gly Ser Gly Thr Gly Gly Ala Ser Ser Gly Gly Ala Ser Gly Ala
                325                 330                 335

Ser Gly Ala Pro Glu Leu Leu Gly Gly Pro Ser Val Phe Leu Phe Pro
            340                 345                 350

Pro Lys Pro Lys Asp Thr Leu Met Ile Ser Arg Thr Pro Glu Val Thr
        355                 360                 365

Cys Val Val Val Asp Val Ser His Glu Asp Pro Glu Val Gln Phe Lys
    370                 375                 380

Trp Tyr Val Asp Gly Val Glu Val His Asn Ala Lys Thr Lys Pro Arg
385                 390                 395                 400

Glu Glu Gln Tyr Asn Ser Thr Phe Arg Val Val Ser Val Leu Thr Val
                405                 410                 415

Leu His Gln Asp Trp Leu Asn Gly Lys Glu Tyr Lys Cys Lys Val Ser
            420                 425                 430

Asn Lys Ala Leu Pro Ala Pro Ile Glu Lys Thr Ile Ser Lys Thr Lys
        435                 440                 445

Gly Gln Pro Arg Glu Pro Gln Val Tyr Thr Leu Pro Pro Ser Arg Glu
    450                 455                 460

Glu Met Thr Lys Asn Gln Val Ser Leu Thr Cys Leu Val Lys Gly Phe
465                 470                 475                 480

Tyr Pro Ser Asp Ile Ala Val Glu Trp Glu Ser Ser Gly Gln Pro Glu
                485                 490                 495

Asn Asn Tyr Asn Thr Thr Pro Pro Met Leu Asp Ser Asp Gly Ser Phe
            500                 505                 510

Phe Leu Tyr Ser Lys Leu Thr Val Asp Lys Ser Arg Trp Gln Gln Gly
        515                 520                 525

Asn Ile Phe Ser Cys Ser Val Met His Glu Ala Leu His Asn Arg Phe
    530                 535                 540

Thr Gln Lys Ser Leu Ser Leu Ser Pro Gly Lys
545                 550                 555

<210> SEQ ID NO 37
<211> LENGTH: 608
<212> TYPE: PRT
<213> ORGANISM: Artificial sequence
<220> FEATURE:
<223> OTHER INFORMATION: Format 2a

<400> SEQUENCE: 37

Glu Leu Lys Thr Pro Leu Gly Asp Thr Thr His Thr Cys Pro Arg Cys
```

-continued

```
1               5                   10                  15
Pro Glu Pro Lys Ser Cys Asp Thr Pro Pro Cys Pro Arg Cys Pro
                20                  25                  30

Glu Pro Lys Ser Cys Asp Thr Pro Pro Cys Pro Arg Cys Pro Glu
                35                  40                  45

Pro Lys Ser Cys Asp Thr Pro Pro Cys Pro Arg Cys Pro Ala Pro
            50                  55                  60

Glu Leu Leu Gly Gly Pro Ser Val Phe Leu Phe Pro Pro Lys Pro Lys
65                      70                  75                  80

Asp Thr Leu Met Ile Ser Arg Thr Pro Glu Val Thr Cys Val Val
                    85                  90                  95

Asp Val Ser His Glu Asp Pro Glu Val Gln Phe Lys Trp Tyr Val Asp
                100                 105                 110

Gly Val Glu Val His Asn Ala Lys Thr Lys Pro Arg Glu Glu Gln Tyr
                115                 120                 125

Asn Ser Thr Phe Arg Val Val Ser Val Leu Thr Val Leu His Gln Asp
            130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gly Gly
                    165                 170                 175

Ser Gly Gly Gly Gly Ser Gly Gly Gly Gly Ser Gly Gly Gly Gly Ser
                180                 185                 190

Gly Gly Gly Gly Ser Glu Leu Lys Thr Pro Leu Gly Asp Thr Thr His
                195                 200                 205

Thr Cys Pro Arg Cys Pro Glu Pro Lys Ser Cys Asp Thr Pro Pro
                210                 215                 220

Cys Pro Arg Cys Pro Glu Pro Lys Ser Cys Asp Thr Pro Pro Cys
225                 230                 235                 240

Pro Arg Cys Pro Glu Pro Lys Ser Cys Asp Thr Pro Pro Cys Pro
                    245                 250                 255

Arg Cys Pro Ala Pro Glu Leu Leu Gly Gly Pro Ser Val Phe Leu Phe
                260                 265                 270

Pro Pro Lys Pro Lys Asp Thr Leu Met Ile Ser Arg Thr Pro Glu Val
            275                 280                 285

Thr Cys Val Val Val Asp Val Ser His Glu Asp Pro Glu Val Gln Phe
            290                 295                 300

Lys Trp Tyr Val Asp Gly Val Glu Val His Asn Ala Lys Thr Lys Pro
305                 310                 315                 320

Arg Glu Glu Gln Tyr Asn Ser Thr Phe Arg Val Val Ser Val Leu Thr
                    325                 330                 335

Val Leu His Gln Asp Trp Leu Asn Gly Lys Glu Tyr Lys Cys Lys Val
                340                 345                 350

Ser Asn Lys Ala Leu Pro Ala Pro Ile Glu Lys Thr Ile Ser Lys Thr
            355                 360                 365

Lys Gly Gln Pro Arg Glu Pro Gln Val Tyr Thr Leu Pro Pro Ser Arg
370                 375                 380

Glu Glu Met Thr Lys Asn Gln Val Ser Leu Thr Cys Leu Val Lys Gly
385                 390                 395                 400

Phe Tyr Pro Ser Asp Ile Ala Val Glu Trp Glu Ser Ser Gly Gln Pro
                405                 410                 415

Glu Asn Asn Tyr Asn Thr Thr Pro Pro Met Leu Asp Ser Asp Gly Ser
                420                 425                 430
```

```
Phe Phe Leu Tyr Ser Lys Leu Thr Val Asp Lys Ser Arg Trp Gln Gln
            435                 440                 445

Gly Asn Ile Phe Ser Cys Ser Val Met His Glu Ala Leu His Asn Arg
        450                 455                 460

Phe Thr Gln Lys Ser Leu Ser Leu Ser Pro Lys Gly Gly Gly Gly Gly
465                 470                 475                 480

Ser Gly Gly Gly Gly Ser Gly Gly Gly Gly Ser Gly Gly Gly Gly Ser
                485                 490                 495

Gly Gly Gly Gly Ser Gly Gln Pro Arg Glu Pro Gln Val Tyr Thr Leu
                500                 505                 510

Pro Pro Ser Arg Glu Glu Met Thr Lys Asn Gln Val Ser Leu Thr Cys
            515                 520                 525

Leu Val Lys Gly Phe Tyr Pro Ser Asp Ile Ala Val Glu Trp Glu Ser
        530                 535                 540

Ser Gly Gln Pro Glu Asn Asn Tyr Asn Thr Thr Pro Pro Met Leu Asp
545                 550                 555                 560

Ser Asp Gly Ser Phe Phe Leu Tyr Ser Lys Leu Thr Val Asp Lys Ser
                565                 570                 575

Arg Trp Gln Gln Gly Asn Ile Phe Ser Cys Ser Val Met His Glu Ala
            580                 585                 590

Leu His Asn Arg Phe Thr Gln Lys Ser Leu Ser Leu Ser Pro Gly Lys
        595                 600                 605

<210> SEQ ID NO 38
<211> LENGTH: 546
<212> TYPE: PRT
<213> ORGANISM: Artificial sequence
<220> FEATURE:
<223> OTHER INFORMATION: Format 2b

<400> SEQUENCE: 38

Glu Leu Lys Thr Pro Leu Gly Asp Thr Thr His Thr Ser Pro Arg Ser
1               5                   10                  15

Pro Glu Pro Lys Ser Ser Asp Thr Pro Pro Ser Pro Arg Ser Pro
            20                  25                  30

Glu Pro Lys Ser Ser Asp Thr Pro Pro Ser Pro Arg Ser Pro Glu
        35                  40                  45

Pro Lys Ser Ser Asp Thr Pro Pro Ser Pro Arg Ser Pro Ala Pro
    50                  55                  60

Glu Leu Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
            100                 105                 110

Gly Val Glu Val His Asn Ala Lys Thr Lys Pro Arg Glu Glu Gln Tyr
        115                 120                 125

Asn Ser Thr Phe Arg Val Val Ser Val Leu Thr Val Leu His Gln Asp
    130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gly Gly Gly
                165                 170                 175

Ser Gly Gly Gly Gly Ser Gly Gly Gly Gly Ser Gly Gly Gly Gly Ser
            180                 185                 190
```

```
Gly Gly Gly Gly Ser Ala Pro Glu Leu Leu Gly Gly Pro Ser Val Phe
            195                 200                 205
Leu Phe Pro Pro Lys Pro Lys Asp Thr Leu Met Ile Ser Arg Thr Pro
210                 215                 220
Glu Val Thr Cys Val Val Val Asp Val Ser His Glu Asp Pro Glu Val
225                 230                 235                 240
Gln Phe Lys Trp Tyr Val Asp Gly Val Glu Val His Asn Ala Lys Thr
            245                 250                 255
Lys Pro Arg Glu Glu Gln Tyr Asn Ser Thr Phe Arg Val Val Ser Val
            260                 265                 270
Leu Thr Val Leu His Gln Asp Trp Leu Asn Gly Lys Glu Tyr Lys Cys
            275                 280                 285
Lys Val Ser Asn Lys Ala Leu Pro Ala Pro Ile Glu Lys Thr Ile Ser
            290                 295                 300
Lys Thr Lys Gly Gln Pro Arg Glu Pro Gln Val Tyr Thr Leu Pro Pro
305                 310                 315                 320
Ser Arg Glu Glu Met Thr Lys Asn Gln Val Ser Leu Thr Cys Leu Val
                325                 330                 335
Lys Gly Phe Tyr Pro Ser Asp Ile Ala Val Glu Trp Glu Ser Ser Gly
            340                 345                 350
Gln Pro Glu Asn Asn Tyr Asn Thr Thr Pro Pro Met Leu Asp Ser Asp
            355                 360                 365
Gly Ser Phe Phe Leu Tyr Ser Lys Leu Thr Val Asp Lys Ser Arg Trp
            370                 375                 380
Gln Gln Gly Asn Ile Phe Ser Cys Ser Val Met His Glu Ala Leu His
385                 390                 395                 400
Asn Arg Phe Thr Gln Lys Ser Leu Ser Leu Ser Pro Gly Lys Gly Gly
                405                 410                 415
Gly Gly Ser Gly Gly Gly Gly Ser Gly Gly Gly Gly Ser Gly Gly Gly
            420                 425                 430
Gly Ser Gly Gly Gly Gly Ser Gly Gln Pro Arg Glu Pro Gln Val Tyr
            435                 440                 445
Thr Leu Pro Pro Ser Arg Glu Glu Met Thr Lys Asn Gln Val Ser Leu
            450                 455                 460
Thr Cys Leu Val Lys Gly Phe Tyr Pro Ser Asp Ile Ala Val Glu Trp
465                 470                 475                 480
Glu Ser Ser Gly Gln Pro Glu Asn Asn Tyr Asn Thr Thr Pro Pro Met
                485                 490                 495
Leu Asp Ser Asp Gly Ser Phe Phe Leu Tyr Ser Lys Leu Thr Val Asp
            500                 505                 510
Lys Ser Arg Trp Gln Gln Gly Asn Ile Phe Ser Cys Ser Val Met His
            515                 520                 525
Glu Ala Leu His Asn Arg Phe Thr Gln Lys Ser Leu Ser Leu Ser Pro
530                 535                 540
Gly Lys
545
```

<210> SEQ ID NO 39
<211> LENGTH: 484
<212> TYPE: PRT
<213> ORGANISM: Artificial sequence
<220> FEATURE:
<223> OTHER INFORMATION: Format 2c

<400> SEQUENCE: 39

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys Gly Gly
            100                 105                 110

Gly Gly Ser Gly Gly Gly Gly Ser Gly Gly Gly Gly Ser Gly Gly Gly
            115                 120                 125

Gly Ser Gly Gly Gly Ser Ala Pro Glu Leu Leu Gly Gly Pro Ser
        130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Gln Phe Lys Trp Tyr Val Asp Gly Val Glu Val His Asn Ala
                180                 185                 190

Lys Thr Lys Pro Arg Glu Glu Gln Tyr Asn Ser Thr Phe Arg Val Val
            195                 200                 205

Ser Val Leu Thr Val Leu His Gln Asp Trp Leu Asn Gly Lys Glu Tyr
        210                 215                 220

Lys Cys Lys Val Ser Asn Lys Ala Leu Pro Ala Pro Ile Glu Lys Thr
225                 230                 235                 240

Ile Ser Lys Thr Lys Gly Gln Pro Arg Glu Pro Gln Val Tyr Thr Leu
                245                 250                 255

Pro Pro Ser Arg Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Ser Gly Gln Pro Glu Asn Asn Tyr Asn Thr Thr Pro Pro Met Leu Asp
290                 295                 300

Ser Asp Gly Ser Phe Phe Leu Tyr Ser Lys Leu Thr Val Asp Lys Ser
305                 310                 315                 320

Arg Trp Gln Gln Gly Asn Ile Phe Ser Cys Ser Val Met His Glu Ala
                325                 330                 335

Leu His Asn Arg Phe Thr Gln Lys Ser Leu Ser Leu Ser Pro Gly Lys
            340                 345                 350

Gly Gly Gly Gly Ser Gly Gly Gly Ser Gly Gly Gly Gly Ser Gly
        355                 360                 365

Gly Gly Ser Gly Gly Gly Gly Ser Gly Gln Pro Arg Glu Pro Gln
370                 375                 380

Val Tyr Thr Leu Pro Pro Ser Arg Glu Glu Met Thr Lys Asn Gln Val
385                 390                 395                 400

Ser Leu Thr Cys Leu Val Lys Gly Phe Tyr Pro Ser Asp Ile Ala Val
                405                 410                 415
```

```
Glu Trp Glu Ser Ser Gly Gln Pro Glu Asn Asn Tyr Asn Thr Thr Pro
                420                 425                 430

Pro Met Leu Asp Ser Asp Gly Ser Phe Phe Leu Tyr Ser Lys Leu Thr
        435                 440                 445

Val Asp Lys Ser Arg Trp Gln Gln Gly Asn Ile Phe Ser Cys Ser Val
    450                 455                 460

Met His Glu Ala Leu His Asn Arg Phe Thr Gln Lys Ser Leu Ser Leu
465                 470                 475                 480

Ser Pro Gly Lys

<210> SEQ ID NO 40
<211> LENGTH: 98
<212> TYPE: PRT
<213> ORGANISM: Homo sapiens

<400> SEQUENCE: 40

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val

<210> SEQ ID NO 41
<211> LENGTH: 110
<212> TYPE: PRT
<213> ORGANISM: Homo sapiens

<400> SEQUENCE: 41

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110

<210> SEQ ID NO 42
<211> LENGTH: 107
<212> TYPE: PRT
<213> ORGANISM: Homo sapiens

<400> SEQUENCE: 42
```

```
Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
50                      55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105
```

<210> SEQ ID NO 43
<211> LENGTH: 208
<212> TYPE: PRT
<213> ORGANISM: Artificial sequence
<220> FEATURE:
<223> OTHER INFORMATION: CH1CH2

<400> SEQUENCE: 43

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                      55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Ala Pro Glu Phe Leu Gly Gly Pro Ser Val Phe Leu Phe Pro
            100                 105                 110

Pro Lys Pro Lys Asp Thr Leu Met Ile Ser Arg Thr Pro Glu Val Thr
        115                 120                 125

Cys Val Val Val Asp Val Ser Gln Glu Asp Pro Glu Val Gln Phe Asn
130                     135                 140

Trp Tyr Val Asp Gly Val Glu Val His Asn Ala Lys Thr Lys Pro Arg
145                 150                 155                 160

Glu Glu Gln Phe Asn Ser Thr Tyr Arg Val Val Ser Val Leu Thr Val
                165                 170                 175

Leu His Gln Asp Trp Leu Asn Gly Lys Glu Tyr Lys Cys Lys Val Ser
            180                 185                 190

Asn Lys Gly Leu Pro Ser Ser Ile Glu Lys Thr Ile Ser Lys Ala Lys
        195                 200                 205
```

<210> SEQ ID NO 44
<211> LENGTH: 217
<212> TYPE: PRT
<213> ORGANISM: Homo sapiens

<400> SEQUENCE: 44

Ala Pro Glu Phe Leu Gly Gly Pro Ser Val Phe Leu Phe Pro Pro Lys

```
  1               5                  10                 15
Pro Lys Asp Thr Leu Met Ile Ser Arg Thr Pro Glu Val Thr Cys Val
             20                 25                 30

Val Val Asp Val Ser Gln Glu Asp Pro Glu Val Gln Phe Asn Trp Tyr
             35                 40                 45

Val Asp Gly Val Glu Val His Asn Ala Lys Thr Lys Pro Arg Glu Glu
         50                 55                 60

Gln Phe Asn Ser Thr Tyr Arg Val Val Ser Val Leu Thr Val Leu His
 65                 70                 75                 80

Gln Asp Trp Leu Asn Gly Lys Glu Tyr Lys Cys Lys Val Ser Asn Lys
                 85                 90                 95

Gly Leu Pro Ser Ser Ile Glu Lys Thr Ile Ser Lys Ala Lys Gly Gln
             100                105                110

Pro Arg Glu Pro Gln Val Tyr Thr Leu Pro Pro Ser Gln Glu Glu Met
             115                120                125

Thr Lys Asn Gln Val Ser Leu Thr Cys Leu Val Lys Gly Phe Tyr Pro
         130                135                140

Ser Asp Ile Ala Val Glu Trp Glu Ser Asn Gly Gln Pro Glu Asn Asn
145                150                155                160

Tyr Lys Thr Thr Pro Pro Val Leu Asp Ser Asp Gly Ser Phe Phe Leu
                 165                170                175

Tyr Ser Arg Leu Thr Val Asp Lys Ser Arg Trp Gln Glu Gly Asn Val
             180                185                190

Phe Ser Cys Ser Val Met His Glu Ala Leu His Asn His Tyr Thr Gln
             195                200                205

Lys Ser Leu Ser Leu Ser Leu Gly Lys
             210                215

<210> SEQ ID NO 45
<211> LENGTH: 315
<212> TYPE: PRT
<213> ORGANISM: Artificial sequence
<220> FEATURE:
<223> OTHER INFORMATION: CH1CH2CH3

<400> SEQUENCE: 45

Ala Ser Thr Lys Gly Pro Ser Val Phe Pro Leu Ala Pro Cys Ser Arg
1               5                  10                 15

Ser Thr Ser Glu Ser Thr Ala Ala Leu Gly Cys Leu Val Lys Asp Tyr
             20                 25                 30

Phe Pro Glu Pro Val Thr Val Ser Trp Asn Ser Gly Ala Leu Thr Ser
             35                 40                 45

Gly Val His Thr Phe Pro Ala Val Leu Gln Ser Ser Gly Leu Tyr Ser
         50                 55                 60

Leu Ser Ser Val Val Thr Val Pro Ser Ser Leu Gly Thr Lys Thr
 65                 70                 75                 80

Tyr Thr Cys Asn Val Asp His Lys Pro Ser Asn Thr Lys Val Asp Lys
                 85                 90                 95

Arg Val Ala Pro Glu Phe Leu Gly Gly Pro Ser Val Phe Leu Phe Pro
             100                105                110

Pro Lys Pro Lys Asp Thr Leu Met Ile Ser Arg Thr Pro Glu Val Thr
             115                120                125

Cys Val Val Val Asp Val Ser Gln Glu Asp Pro Glu Val Gln Phe Asn
         130                135                140

Trp Tyr Val Asp Gly Val Glu Val His Asn Ala Lys Thr Lys Pro Arg
```

```
                145                 150                 155                 160
Glu Glu Gln Phe Asn Ser Thr Tyr Arg Val Val Ser Val Leu Thr Val
            165                 170                 175

Leu His Gln Asp Trp Leu Asn Gly Lys Glu Tyr Lys Cys Lys Val Ser
            180                 185                 190

Asn Lys Gly Leu Pro Ser Ser Ile Glu Lys Thr Ile Ser Lys Ala Lys
            195                 200                 205

Gly Gln Pro Arg Glu Pro Gln Val Tyr Thr Leu Pro Pro Ser Gln Glu
            210                 215                 220

Glu Met Thr Lys Asn Gln Val Ser Leu Thr Cys Leu Val Lys Gly Phe
225                 230                 235                 240

Tyr Pro Ser Asp Ile Ala Val Glu Trp Glu Ser Asn Gly Gln Pro Glu
            245                 250                 255

Asn Asn Tyr Lys Thr Thr Pro Pro Val Leu Asp Ser Asp Gly Ser Phe
            260                 265                 270

Phe Leu Tyr Ser Arg Leu Thr Val Asp Lys Ser Arg Trp Gln Glu Gly
            275                 280                 285

Asn Val Phe Ser Cys Ser Val Met His Glu Ala Leu His Asn His Tyr
            290                 295                 300

Thr Gln Lys Ser Leu Ser Leu Ser Leu Gly Lys
305                 310                 315

<210> SEQ ID NO 46
<211> LENGTH: 327
<212> TYPE: PRT
<213> ORGANISM: Homo sapiens

<400> SEQUENCE: 46

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
            165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205
```

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 47
<211> LENGTH: 493
<212> TYPE: PRT
<213> ORGANISM: Artificial sequence
<220> FEATURE:
<223> OTHER INFORMATION: Format 1c

<400> SEQUENCE: 47

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Lys Gly Gly Ser Ser Thr Ala Ser
    210                 215                 220

Gly Ser Gly Ser Gly Gly Ser Gly Thr Ala Gly Ser Ser Gly Gly Ala
225                 230                 235                 240

```
Gly Ser Ser Gly Gly Ser Thr Thr Ala Gly Ser Ala Ser Gly Ser
                245                 250                 255

Gly Ser Thr Gly Ser Gly Thr Gly Gly Ala Ser Ser Gly Gly Ala Ser
            260                 265                 270

Gly Ala Ser Gly Ala Pro Glu Phe Leu Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser Gln Glu Asp Pro Glu Val Gln
305                 310                 315                 320

Phe Asn Trp Tyr Val Asp Gly Val Glu Val His Asn Ala Lys Thr Lys
                325                 330                 335

Pro Arg Glu Glu Gln Phe Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Gly Leu Pro Ser Ser Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Gln Glu Glu Met Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Arg Leu Thr Val Asp Lys Ser Arg Trp Gln
    450                 455                 460

Glu Gly Asn Val Phe Ser Cys Ser Val Met His Glu Ala Leu His Asn
465                 470                 475                 480

His Tyr Thr Gln Lys Ser Leu Ser Leu Gly Lys
                485                 490
```

<210> SEQ ID NO 48
<211> LENGTH: 517
<212> TYPE: PRT
<213> ORGANISM: Artificial sequence
<220> FEATURE:
<223> OTHER INFORMATION: Format 1a

<400> SEQUENCE: 48

```
Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110
```

```
Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
            130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
210                 215                 220

Leu Ser Leu Gly Lys Gly Gly Ser Ser Thr Ala Ser Gly Ser Gly Ser
225                 230                 235                 240

Gly Gly Ser Gly Thr Ala Gly Ser Ser Gly Ala Gly Ser Ser Gly
            245                 250                 255

Gly Ser Thr Thr Ala Gly Gly Ser Ala Ser Gly Ser Gly Ser Thr Gly
            260                 265                 270

Ser Gly Thr Gly Gly Ala Ser Ser Gly Gly Ala Ser Gly Ala Ser Gly
            275                 280                 285

Glu Ser Lys Tyr Gly Pro Pro Cys Pro Ser Cys Pro Ala Pro Glu Phe
            290                 295                 300

Leu Gly Gly Pro Ser Val Phe Leu Phe Pro Pro Lys Pro Lys Asp Thr
305                 310                 315                 320

Leu Met Ile Ser Arg Thr Pro Glu Val Thr Cys Val Val Val Asp Val
                325                 330                 335

Ser Gln Glu Asp Pro Glu Val Gln Phe Asn Trp Tyr Val Asp Gly Val
            340                 345                 350

Glu Val His Asn Ala Lys Thr Lys Pro Arg Glu Glu Gln Phe Asn Ser
            355                 360                 365

Thr Tyr Arg Val Val Ser Val Leu Thr Val Leu His Gln Asp Trp Leu
            370                 375                 380

Asn Gly Lys Glu Tyr Lys Cys Lys Val Ser Asn Lys Gly Leu Pro Ser
385                 390                 395                 400

Ser Ile Glu Lys Thr Ile Ser Lys Ala Lys Gly Gln Pro Arg Glu Pro
            405                 410                 415

Gln Val Tyr Thr Leu Pro Pro Ser Gln Glu Glu Met Thr Lys Asn Gln
            420                 425                 430

Val Ser Leu Thr Cys Leu Val Lys Gly Phe Tyr Pro Ser Asp Ile Ala
            435                 440                 445

Val Glu Trp Glu Ser Asn Gly Gln Pro Glu Asn Asn Tyr Lys Thr Thr
            450                 455                 460

Pro Pro Val Leu Asp Ser Asp Gly Ser Phe Phe Leu Tyr Ser Arg Leu
465                 470                 475                 480

Thr Val Asp Lys Ser Arg Trp Gln Glu Gly Asn Val Phe Ser Cys Ser
            485                 490                 495

Val Met His Glu Ala Leu His Asn His Tyr Thr Gln Lys Ser Leu Ser
            500                 505                 510

Leu Ser Leu Gly Lys
            515
```

<210> SEQ ID NO 49
<211> LENGTH: 505
<212> TYPE: PRT
<213> ORGANISM: Artificial sequence
<220> FEATURE:
<223> OTHER INFORMATION: Format 1b

<400> SEQUENCE: 49

```
Glu Ser Lys Tyr Gly Pro Pro Ser Pro Ser Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys Gly Gly Ser Ser Thr Ala Ser Gly Ser Gly Ser
225                 230                 235                 240

Gly Gly Ser Gly Thr Ala Gly Ser Ser Gly Gly Ala Gly Ser Ser Gly
                245                 250                 255

Gly Ser Thr Thr Ala Gly Gly Ser Ala Ser Gly Ser Gly Ser Thr Gly
            260                 265                 270

Ser Gly Thr Gly Gly Ala Ser Ser Gly Gly Ala Ser Gly Ala Ser Gly
        275                 280                 285

Ala Pro Glu Phe Leu Gly Gly Pro Ser Val Phe Leu Phe Pro Pro Lys
    290                 295                 300

Pro Lys Asp Thr Leu Met Ile Ser Arg Thr Pro Glu Val Thr Cys Val
305                 310                 315                 320

Val Val Asp Val Ser Gln Glu Asp Pro Glu Val Gln Phe Asn Trp Tyr
                325                 330                 335

Val Asp Gly Val Glu Val His Asn Ala Lys Thr Lys Pro Arg Glu Glu
            340                 345                 350

Gln Phe Asn Ser Thr Tyr Arg Val Val Ser Val Leu Thr Val Leu His
        355                 360                 365

Gln Asp Trp Leu Asn Gly Lys Glu Tyr Lys Cys Lys Val Ser Asn Lys
```

```
                370             375              380
Gly Leu Pro Ser Ser Ile Glu Lys Thr Ile Ser Lys Ala Lys Gly Gln
385                 390                 395                 400

Pro Arg Glu Pro Gln Val Tyr Thr Leu Pro Ser Gln Glu Glu Met
            405                 410                 415

Thr Lys Asn Gln Val Ser Leu Thr Cys Leu Val Lys Gly Phe Tyr Pro
            420                 425                 430

Ser Asp Ile Ala Val Glu Trp Glu Ser Asn Gly Gln Pro Glu Asn Asn
            435                 440                 445

Tyr Lys Thr Thr Pro Pro Val Leu Asp Ser Asp Gly Ser Phe Phe Leu
            450                 455                 460

Tyr Ser Arg Leu Thr Val Asp Lys Ser Arg Trp Gln Glu Gly Asn Val
465                 470                 475                 480

Phe Ser Cys Ser Val Met His Glu Ala Leu His Asn His Tyr Thr Gln
                485                 490                 495

Lys Ser Leu Ser Leu Ser Leu Gly Lys
                500                 505

<210> SEQ ID NO 50
<211> LENGTH: 508
<212> TYPE: PRT
<213> ORGANISM: Artificial sequence
<220> FEATURE:
<223> OTHER INFORMATION: Format 2a

<400> SEQUENCE: 50

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
            50                  55                  60

Glu Val His Asn Ala Lys Thr Lys Pro Arg Glu Glu Gln Phe Asn Ser
65              70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gly Gly Gly Ser Gly
            115                 120                 125

Gly Gly Gly Ser Gly Gly Gly Gly Ser Gly Gly Gly Gly Ser Gly Gly
            130                 135                 140

Gly Gly Ser Glu Ser Lys Tyr Gly Pro Pro Cys Pro Ser Cys Pro Ala
145                 150                 155                 160

Pro Glu Phe Leu Gly Gly Pro Ser Val Phe Leu Phe Pro Pro Lys Pro
                165                 170                 175

Lys Asp Thr Leu Met Ile Ser Arg Thr Pro Glu Val Thr Cys Val Val
                180                 185                 190

Val Asp Val Ser Gln Glu Asp Pro Glu Val Gln Phe Asn Trp Tyr Val
            195                 200                 205

Asp Gly Val Glu Val His Asn Ala Lys Thr Lys Pro Arg Glu Glu Gln
            210                 215                 220

Phe Asn Ser Thr Tyr Arg Val Val Ser Val Leu Thr Val Leu His Gln
```

```
                225                 230                 235                 240
Asp Trp Leu Asn Gly Lys Glu Tyr Lys Cys Lys Val Ser Asn Lys Gly
                    245                 250                 255
Leu Pro Ser Ser Ile Glu Lys Thr Ile Ser Lys Ala Lys Gly Gln Pro
                260                 265                 270
Arg Glu Pro Gln Val Tyr Thr Leu Pro Pro Ser Gln Glu Met Thr
                275                 280                 285
Lys Asn Gln Val Ser Leu Thr Cys Leu Val Lys Gly Phe Tyr Pro Ser
                290                 295                 300
Asp Ile Ala Val Glu Trp Glu Ser Asn Gly Gln Pro Glu Asn Asn Tyr
305                 310                 315                 320
Lys Thr Thr Pro Pro Val Leu Asp Ser Asp Gly Ser Phe Phe Leu Tyr
                        325                 330                 335
Ser Arg Leu Thr Val Asp Lys Ser Arg Trp Gln Glu Gly Asn Val Phe
                    340                 345                 350
Ser Cys Ser Val Met His Glu Ala Leu His Asn His Tyr Thr Gln Lys
                355                 360                 365
Ser Leu Ser Leu Ser Leu Gly Lys Gly Gly Gly Ser Gly Gly Gly
            370                 375                 380
Gly Ser Gly Gly Gly Gly Ser Gly Gly Gly Gly Ser Gly Gly Gly Gly
385                 390                 395                 400
Ser Gly Gln Pro Arg Glu Pro Gln Val Tyr Thr Leu Pro Pro Ser Gln
                    405                 410                 415
Glu Glu Met Thr Lys Asn Gln Val Ser Leu Thr Cys Leu Val Lys Gly
                420                 425                 430
Phe Tyr Pro Ser Asp Ile Ala Val Glu Trp Glu Ser Asn Gly Gln Pro
            435                 440                 445
Glu Asn Asn Tyr Lys Thr Thr Pro Pro Val Leu Asp Ser Asp Gly Ser
        450                 455                 460
Phe Phe Leu Tyr Ser Arg Leu Thr Val Asp Lys Ser Arg Trp Gln Glu
465                 470                 475                 480
Gly Asn Val Phe Ser Cys Ser Val Met His Glu Ala Leu His Asn His
                    485                 490                 495
Tyr Thr Gln Lys Ser Leu Ser Leu Ser Leu Gly Lys
                500                 505

<210> SEQ ID NO 51
<211> LENGTH: 496
<212> TYPE: PRT
<213> ORGANISM: Artificial sequence
<220> FEATURE:
<223> OTHER INFORMATION: Format 2b

<400> SEQUENCE: 51

Glu Ser Lys Tyr Gly Pro Pro Ser Pro Ser Pro Ala Pro Glu Phe
1               5                   10                  15
Leu Gly Gly Pro Ser Val Phe Leu Phe Pro Pro Lys Pro Lys Asp Thr
                20                  25                  30
Leu Met Ile Ser Arg Thr Pro Glu Val Thr Cys Val Val Val Asp Val
            35                  40                  45
Ser Gln Glu Asp Pro Glu Val Gln Phe Asn Trp Tyr Val Asp Gly Val
        50                  55                  60
Glu Val His Asn Ala Lys Thr Lys Pro Arg Glu Glu Gln Phe Asn Ser
65                  70                  75                  80
Thr Tyr Arg Val Val Ser Val Leu Thr Val Leu His Gln Asp Trp Leu
```

```
                85                  90                  95
Asn Gly Lys Glu Tyr Lys Cys Lys Val Ser Asn Lys Gly Leu Pro Ser
            100                 105                 110
Ser Ile Glu Lys Thr Ile Ser Lys Ala Lys Gly Gly Gly Ser Gly
            115                 120                 125
Gly Gly Gly Ser Gly Gly Gly Ser Gly Gly Gly Ser Gly Gly
        130                 135                 140
Gly Gly Ser Ala Pro Glu Phe Leu Gly Gly Pro Ser Val Phe Leu Phe
145                 150                 155                 160
Pro Pro Lys Pro Lys Asp Thr Leu Met Ile Ser Arg Thr Pro Glu Val
                165                 170                 175
Thr Cys Val Val Val Asp Val Ser Gln Glu Asp Pro Glu Val Gln Phe
                180                 185                 190
Asn Trp Tyr Val Asp Gly Val Glu Val His Asn Ala Lys Thr Lys Pro
            195                 200                 205
Arg Glu Glu Gln Phe Asn Ser Thr Tyr Arg Val Val Ser Val Leu Thr
            210                 215                 220
Val Leu His Gln Asp Trp Leu Asn Gly Lys Glu Tyr Lys Cys Lys Val
225                 230                 235                 240
Ser Asn Lys Gly Leu Pro Ser Ser Ile Glu Lys Thr Ile Ser Lys Ala
                245                 250                 255
Lys Gly Gln Pro Arg Glu Pro Gln Val Tyr Thr Leu Pro Pro Ser Gln
                260                 265                 270
Glu Glu Met Thr Lys Asn Gln Val Ser Leu Thr Cys Leu Val Lys Gly
                275                 280                 285
Phe Tyr Pro Ser Asp Ile Ala Val Glu Trp Glu Ser Asn Gly Gln Pro
            290                 295                 300
Glu Asn Asn Tyr Lys Thr Thr Pro Pro Val Leu Asp Ser Asp Gly Ser
305                 310                 315                 320
Phe Phe Leu Tyr Ser Arg Leu Thr Val Asp Lys Ser Arg Trp Gln Glu
                325                 330                 335
Gly Asn Val Phe Ser Cys Ser Val Met His Glu Ala Leu His Asn His
            340                 345                 350
Tyr Thr Gln Lys Ser Leu Ser Leu Ser Leu Gly Lys Gly Gly Gly
            355                 360                 365
Ser Gly Gly Gly Ser Gly Gly Gly Ser Gly Gly Gly Ser
        370                 375                 380
Gly Gly Gly Ser Gly Gln Pro Arg Glu Pro Gln Val Tyr Thr Leu
385                 390                 395                 400
Pro Pro Ser Gln Glu Glu Met Thr Lys Asn Gln Val Ser Leu Thr Cys
                405                 410                 415
Leu Val Lys Gly Phe Tyr Pro Ser Asp Ile Ala Val Glu Trp Glu Ser
                420                 425                 430
Asn Gly Gln Pro Glu Asn Asn Tyr Lys Thr Thr Pro Pro Val Leu Asp
                435                 440                 445
Ser Asp Gly Ser Phe Phe Leu Tyr Ser Arg Leu Thr Val Asp Lys Ser
            450                 455                 460
Arg Trp Gln Glu Gly Asn Val Phe Ser Cys Ser Val Met His Glu Ala
465                 470                 475                 480
Leu His Asn His Tyr Thr Gln Lys Ser Leu Ser Leu Ser Leu Gly Lys
                485                 490                 495

<210> SEQ ID NO 52
```

<211> LENGTH: 484
<212> TYPE: PRT
<213> ORGANISM: Artificial sequence
<220> FEATURE:
<223> OTHER INFORMATION: Format 2c

<400> SEQUENCE: 52

| | | | | | | | | | | | | | | | |
|---|---|---|---|---|---|---|---|---|---|---|---|---|---|---|---|
| Ala | Pro | Glu | Phe | Leu | Gly | Gly | Pro | Ser | Val | Phe | Leu | Phe | Pro | Pro | Lys |
| 1 | | | | 5 | | | | | 10 | | | | | 15 | |
| Pro | Lys | Asp | Thr | Leu | Met | Ile | Ser | Arg | Thr | Pro | Glu | Val | Thr | Cys | Val |
| | | | 20 | | | | | 25 | | | | | 30 | | |
| Val | Val | Asp | Val | Ser | Gln | Glu | Asp | Pro | Glu | Val | Gln | Phe | Asn | Trp | Tyr |
| | | 35 | | | | | 40 | | | | | 45 | | | |
| Val | Asp | Gly | Val | Glu | Val | His | Asn | Ala | Lys | Thr | Lys | Pro | Arg | Glu | Glu |
| | 50 | | | | | 55 | | | | | 60 | | | | |
| Gln | Phe | Asn | Ser | Thr | Tyr | Arg | Val | Val | Ser | Val | Leu | Thr | Val | Leu | His |
| 65 | | | | | 70 | | | | | 75 | | | | | 80 |
| Gln | Asp | Trp | Leu | Asn | Gly | Lys | Glu | Tyr | Lys | Cys | Lys | Val | Ser | Asn | Lys |
| | | | | 85 | | | | | 90 | | | | | 95 | |
| Gly | Leu | Pro | Ser | Ser | Ile | Glu | Lys | Thr | Ile | Ser | Lys | Ala | Lys | Gly | Gly |
| | | | 100 | | | | | 105 | | | | | 110 | | |
| Gly | Gly | Ser | Gly | Gly | Gly | Gly | Ser | Gly | Gly | Gly | Gly | Ser | Gly | Gly | Gly |
| | | 115 | | | | | 120 | | | | | 125 | | | |
| Gly | Ser | Gly | Gly | Gly | Gly | Ser | Ala | Pro | Glu | Phe | Leu | Gly | Gly | Pro | Ser |
| | 130 | | | | | 135 | | | | | 140 | | | | |
| Val | Phe | Leu | Phe | Pro | Pro | Lys | Pro | Lys | Asp | Thr | Leu | Met | Ile | Ser | Arg |
| 145 | | | | | 150 | | | | | 155 | | | | | 160 |
| Thr | Pro | Glu | Val | Thr | Cys | Val | Val | Val | Asp | Val | Ser | Gln | Glu | Asp | Pro |
| | | | | 165 | | | | | 170 | | | | | 175 | |
| Glu | Val | Gln | Phe | Asn | Trp | Tyr | Val | Asp | Gly | Val | Glu | Val | His | Asn | Ala |
| | | | 180 | | | | | 185 | | | | | 190 | | |
| Lys | Thr | Lys | Pro | Arg | Glu | Glu | Gln | Phe | Asn | Ser | Thr | Tyr | Arg | Val | Val |
| | | 195 | | | | | 200 | | | | | 205 | | | |
| Ser | Val | Leu | Thr | Val | Leu | His | Gln | Asp | Trp | Leu | Asn | Gly | Lys | Glu | Tyr |
| | 210 | | | | | 215 | | | | | 220 | | | | |
| Lys | Cys | Lys | Val | Ser | Asn | Lys | Gly | Leu | Pro | Ser | Ser | Ile | Glu | Lys | Thr |
| 225 | | | | | 230 | | | | | 235 | | | | | 240 |
| Ile | Ser | Lys | Ala | Lys | Gly | Gln | Pro | Arg | Glu | Pro | Gln | Val | Tyr | Thr | Leu |
| | | | | 245 | | | | | 250 | | | | | 255 | |
| Pro | Pro | Ser | Gln | Glu | Glu | Met | Thr | Lys | Asn | Gln | Val | Ser | Leu | Thr | Cys |
| | | | 260 | | | | | 265 | | | | | 270 | | |
| Leu | Val | Lys | Gly | Phe | Tyr | Pro | Ser | Asp | Ile | Ala | Val | Glu | Trp | Glu | Ser |
| | | 275 | | | | | 280 | | | | | 285 | | | |
| Asn | Gly | Gln | Pro | Glu | Asn | Asn | Tyr | Lys | Thr | Thr | Pro | Pro | Val | Leu | Asp |
| | 290 | | | | | 295 | | | | | 300 | | | | |
| Ser | Asp | Gly | Ser | Phe | Phe | Leu | Tyr | Ser | Arg | Leu | Thr | Val | Asp | Lys | Ser |
| 305 | | | | | 310 | | | | | 315 | | | | | 320 |
| Arg | Trp | Gln | Glu | Gly | Asn | Val | Phe | Ser | Cys | Ser | Val | Met | His | Glu | Ala |
| | | | | 325 | | | | | 330 | | | | | 335 | |
| Leu | His | Asn | His | Tyr | Thr | Gln | Lys | Ser | Leu | Ser | Leu | Ser | Leu | Gly | Lys |
| | | | 340 | | | | | 345 | | | | | 350 | | |
| Gly | Gly | Gly | Gly | Ser | Gly | Gly | Gly | Ser | Gly | Gly | Gly | Gly | Ser | Gly |
| | | 355 | | | | | 360 | | | | | 365 | | | |
| Gly | Gly | Gly | Ser | Gly | Gly | Gly | Gly | Ser | Gly | Gln | Pro | Arg | Glu | Pro | Gln |
| | 370 | | | | | 375 | | | | | 380 | | | | |

```
Val Tyr Thr Leu Pro Pro Ser Gln Glu Met Thr Lys Asn Gln Val
385                 390                 395                 400

Ser Leu Thr Cys Leu Val Lys Gly Phe Tyr Pro Ser Asp Ile Ala Val
            405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Arg Leu Thr
            435                 440                 445

Val Asp Lys Ser Arg Trp Gln Glu Gly Asn Val Phe Ser Cys Ser Val
            450                 455                 460

Met His Glu Ala Leu His Asn His Tyr Thr Gln Lys Ser Leu Ser Leu
465                 470                 475                 480

Ser Leu Gly Lys

<210> SEQ ID NO 53
<211> LENGTH: 15
<212> TYPE: PRT
<213> ORGANISM: Homo sapiens

<400> SEQUENCE: 53

Glu Pro Lys Ser Cys Asp Lys Thr His Thr Cys Pro Pro Cys Pro
1               5                   10                  15

<210> SEQ ID NO 54
<211> LENGTH: 12
<212> TYPE: PRT
<213> ORGANISM: Homo sapiens

<400> SEQUENCE: 54

Glu Arg Lys Cys Cys Val Glu Cys Pro Pro Cys Pro
1               5                   10

<210> SEQ ID NO 55
<211> LENGTH: 62
<212> TYPE: PRT
<213> ORGANISM: Homo sapiens

<400> SEQUENCE: 55

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
                20                  25                  30

Glu Pro Lys Ser Cys Asp Thr Pro Pro Cys Pro Arg Cys Pro Glu
            35                  40                  45

Pro Lys Ser Cys Asp Thr Pro Pro Cys Pro Arg Cys Pro
    50                  55                  60

<210> SEQ ID NO 56
<211> LENGTH: 12
<212> TYPE: PRT
<213> ORGANISM: Homo sapiens

<400> SEQUENCE: 56

Glu Ser Lys Tyr Gly Pro Pro Cys Pro Ser Cys Pro
1               5                   10

<210> SEQ ID NO 57
<211> LENGTH: 3
<212> TYPE: PRT
<213> ORGANISM: Artificial
```

```
<220> FEATURE:
<223> OTHER INFORMATION: Truncated hinge

<400> SEQUENCE: 57

Pro Cys Pro
1

<210> SEQ ID NO 58
<211> LENGTH: 15
<212> TYPE: PRT
<213> ORGANISM: Artificial
<220> FEATURE:
<223> OTHER INFORMATION: IgG1 hinge Cys-Ser

<400> SEQUENCE: 58

Glu Pro Lys Ser Ser Asp Lys Thr His Thr Ser Pro Pro Ser Pro
1               5                   10                  15

<210> SEQ ID NO 59
<211> LENGTH: 12
<212> TYPE: PRT
<213> ORGANISM: Artificial
<220> FEATURE:
<223> OTHER INFORMATION: IgG2 hinge Cys-Ser

<400> SEQUENCE: 59

Glu Arg Lys Ser Ser Val Glu Ser Pro Pro Ser Pro
1               5                   10

<210> SEQ ID NO 60
<211> LENGTH: 62
<212> TYPE: PRT
<213> ORGANISM: Artificial
<220> FEATURE:
<223> OTHER INFORMATION: IgG3 hinge Cys-Ser

<400> SEQUENCE: 60

Glu Leu Lys Thr Pro Leu Gly Asp Thr Thr His Thr Ser Pro Arg Ser
1               5                   10                  15

Pro Glu Pro Lys Ser Ser Asp Thr Pro Pro Ser Pro Arg Ser Pro
            20                  25                  30

Glu Pro Lys Ser Ser Asp Thr Pro Pro Ser Pro Arg Ser Pro Glu
        35                  40                  45

Pro Lys Ser Ser Asp Thr Pro Pro Ser Pro Arg Ser Pro
    50                  55                  60

<210> SEQ ID NO 61
<211> LENGTH: 12
<212> TYPE: PRT
<213> ORGANISM: Artificial
<220> FEATURE:
<223> OTHER INFORMATION: IgG4 hinge Cys-Ser

<400> SEQUENCE: 61

Glu Ser Lys Tyr Gly Pro Pro Ser Pro Ser Ser Pro
1               5                   10

<210> SEQ ID NO 62
<211> LENGTH: 59
<212> TYPE: PRT
<213> ORGANISM: Artificial
<220> FEATURE:
<223> OTHER INFORMATION: Long linker

<400> SEQUENCE: 62
```

Gly Gly Ser Ser Thr Ala Ser Gly Ser Gly Gly Ser Gly Gly Ser Thr
1               5                   10                  15

Ala Gly Ser Ser Gly Gly Ala Gly Ser Ser Gly Gly Ser Thr Thr Ala
                20                  25                  30

Gly Gly Ser Ala Ser Gly Ser Gly Ser Thr Gly Ser Gly Thr Gly Gly
            35                  40                  45

Ala Ser Ser Gly Gly Ala Ser Gly Ala Ser Gly
            50                  55

<210> SEQ ID NO 63
<211> LENGTH: 25
<212> TYPE: PRT
<213> ORGANISM: Artificial
<220> FEATURE:
<223> OTHER INFORMATION: short linker

<400> SEQUENCE: 63

Gly Gly Gly Gly Ser Gly Gly Gly Ser Gly Gly Gly Gly Ser Gly
1               5                   10                  15

Gly Gly Gly Ser Gly Gly Gly Gly Ser
            20                  25

<210> SEQ ID NO 64
<211> LENGTH: 17
<212> TYPE: PRT
<213> ORGANISM: Homo sapiens

<400> SEQUENCE: 64

Glu Leu Gln Leu Glu Glu Ser Cys Ala Glu Ala Gln Asp Gly Glu Leu
1               5                   10                  15

Asp

<210> SEQ ID NO 65
<211> LENGTH: 26
<212> TYPE: PRT
<213> ORGANISM: Homo sapiens

<400> SEQUENCE: 65

Gly Leu Trp Thr Thr Ile Thr Ile Phe Ile Thr Leu Phe Leu Leu Ser
1               5                   10                  15

Val Cys Tyr Ser Ala Thr Val Thr Phe Phe
            20                  25

<210> SEQ ID NO 66
<211> LENGTH: 28
<212> TYPE: PRT
<213> ORGANISM: Homo sapiens

<400> SEQUENCE: 66

Lys Val Lys Trp Ile Phe Ser Ser Val Val Asp Leu Lys Gln Thr Ile
1               5                   10                  15

Ile Pro Asp Tyr Arg Asn Met Ile Gly Gln Gly Ala
            20                  25

<210> SEQ ID NO 67
<211> LENGTH: 17
<212> TYPE: PRT
<213> ORGANISM: Homo sapiens

<400> SEQUENCE: 67

Glu Leu Gln Leu Glu Glu Ser Cys Ala Glu Ala Gln Asp Gly Glu Leu
1               5                   10                  15

Asp

<210> SEQ ID NO 68
<211> LENGTH: 26
<212> TYPE: PRT
<213> ORGANISM: Homo sapiens

<400> SEQUENCE: 68

Gly Leu Trp Thr Thr Ile Thr Ile Phe Ile Thr Leu Phe Leu Leu Ser
1               5                   10                  15

Val Cys Tyr Ser Ala Thr Ile Thr Phe Phe
            20                  25

<210> SEQ ID NO 69
<211> LENGTH: 28
<212> TYPE: PRT
<213> ORGANISM: Homo sapiens

<400> SEQUENCE: 69

Lys Val Lys Trp Ile Phe Ser Ser Val Val Asp Leu Lys Gln Thr Ile
1               5                   10                  15

Val Pro Asp Tyr Arg Asn Met Ile Arg Gln Gly Ala
            20                  25

<210> SEQ ID NO 70
<211> LENGTH: 17
<212> TYPE: PRT
<213> ORGANISM: Homo sapiens

<400> SEQUENCE: 70

Glu Leu Gln Leu Glu Glu Ser Cys Ala Glu Ala Gln Asp Gly Glu Leu
1               5                   10                  15

Asp

<210> SEQ ID NO 71
<211> LENGTH: 26
<212> TYPE: PRT
<213> ORGANISM: Homo sapiens

<400> SEQUENCE: 71

Gly Leu Trp Thr Thr Ile Thr Ile Phe Ile Thr Leu Phe Leu Leu Ser
1               5                   10                  15

Val Cys Tyr Ser Ala Thr Val Thr Phe Phe
            20                  25

<210> SEQ ID NO 72
<211> LENGTH: 28
<212> TYPE: PRT
<213> ORGANISM: Homo sapiens

<400> SEQUENCE: 72

Lys Val Lys Trp Ile Phe Ser Ser Val Val Asp Leu Lys Gln Thr Ile
1               5                   10                  15

Ile Pro Asp Tyr Arg Asn Met Ile Gly Gln Gly Ala
            20                  25

<210> SEQ ID NO 73
<211> LENGTH: 12
<212> TYPE: PRT
<213> ORGANISM: Homo sapiens

<400> SEQUENCE: 73

Glu Gly Glu Val Ser Ala Asp Glu Glu Gly Phe Glu
1               5                   10

<210> SEQ ID NO 74
<211> LENGTH: 26
<212> TYPE: PRT
<213> ORGANISM: Homo sapiens

<400> SEQUENCE: 74

Asn Leu Trp Ala Thr Ala Ser Thr Phe Ile Val Leu Phe Leu Leu Ser
1               5                   10                  15

Leu Phe Tyr Ser Thr Thr Val Thr Leu Phe
            20                  25

<210> SEQ ID NO 75
<211> LENGTH: 3
<212> TYPE: PRT
<213> ORGANISM: Homo sapiens

<400> SEQUENCE: 75

Lys Val Lys
1

<210> SEQ ID NO 76
<211> LENGTH: 10
<212> TYPE: PRT
<213> ORGANISM: Homo sapiens

<400> SEQUENCE: 76

Asp Asp Tyr Thr Thr Phe Asp Asp Val Gly
1               5                   10

<210> SEQ ID NO 77
<211> LENGTH: 26
<212> TYPE: PRT
<213> ORGANISM: Homo sapiens

<400> SEQUENCE: 77

Ser Leu Trp Thr Thr Leu Ser Thr Phe Val Ala Leu Phe Ile Leu Thr
1               5                   10                  15

Leu Leu Tyr Ser Gly Ile Val Thr Phe Ile
            20                  25

<210> SEQ ID NO 78
<211> LENGTH: 3
<212> TYPE: PRT
<213> ORGANISM: Homo sapiens

<400> SEQUENCE: 78

Lys Val Lys
1

<210> SEQ ID NO 79
<211> LENGTH: 32
<212> TYPE: PRT
<213> ORGANISM: Homo sapiens

<400> SEQUENCE: 79

Gly Ser Cys Ser Val Ala Asp Trp Gln Met Pro Pro Tyr Val Val
1               5                   10                  15

Leu Asp Leu Pro Gln Glu Thr Leu Glu Glu Thr Pro Gly Ala Asn
            20                  25              30

```
<210> SEQ ID NO 80
<211> LENGTH: 27
<212> TYPE: PRT
<213> ORGANISM: Homo sapiens

<400> SEQUENCE: 80

Leu Trp Pro Thr Thr Ile Thr Phe Leu Thr Leu Phe Leu Leu Ser Leu
1               5                   10                  15

Phe Tyr Ser Thr Ala Leu Thr Val Thr Ser Val
            20                  25

<210> SEQ ID NO 81
<211> LENGTH: 12
<212> TYPE: PRT
<213> ORGANISM: Homo sapiens

<400> SEQUENCE: 81

Arg Gly Pro Ser Gly Asn Arg Glu Gly Pro Gln Tyr
1               5                   10

<210> SEQ ID NO 82
<211> LENGTH: 32
<212> TYPE: PRT
<213> ORGANISM: Homo sapiens

<400> SEQUENCE: 82

Gly Ser Cys Cys Val Ala Asp Trp Gln Met Pro Pro Tyr Val Val
1               5                   10                  15

Leu Asp Leu Pro Gln Glu Thr Leu Glu Glu Thr Pro Gly Ala Asn
            20                  25                  30

<210> SEQ ID NO 83
<211> LENGTH: 27
<212> TYPE: PRT
<213> ORGANISM: Homo sapiens

<400> SEQUENCE: 83

Leu Trp Pro Thr Thr Ile Thr Phe Leu Thr Leu Phe Leu Leu Ser Leu
1               5                   10                  15

Phe Tyr Ser Thr Ala Leu Thr Val Thr Ser Val
            20                  25

<210> SEQ ID NO 84
<211> LENGTH: 12
<212> TYPE: PRT
<213> ORGANISM: Homo sapiens

<400> SEQUENCE: 84

Arg Gly Pro Ser Gly Lys Arg Glu Gly Pro Gln Tyr
1               5                   10

<210> SEQ ID NO 85
<211> LENGTH: 15
<212> TYPE: PRT
<213> ORGANISM: Homo sapiens

<400> SEQUENCE: 85

Glu Leu Asp Val Cys Val Glu Glu Ala Glu Gly Glu Ala Pro Trp
1               5                   10                  15

<210> SEQ ID NO 86
<211> LENGTH: 27
<212> TYPE: PRT
```

<213> ORGANISM: Homo sapiens

<400> SEQUENCE: 86

Thr Trp Thr Gly Leu Cys Ile Phe Ala Ala Leu Phe Leu Leu Ser Val
1               5                   10                  15

Ser Tyr Ser Ala Ala Leu Thr Leu Leu Met Val
            20                  25

<210> SEQ ID NO 87
<211> LENGTH: 26
<212> TYPE: PRT
<213> ORGANISM: Homo sapiens

<400> SEQUENCE: 87

Gln Arg Phe Leu Ser Ala Thr Arg Gln Gly Arg Pro Gln Thr Ser Leu
1               5                   10                  15

Asp Tyr Thr Asn Val Leu Gln Pro His Ala
            20                  25

<210> SEQ ID NO 88
<211> LENGTH: 500
<212> TYPE: PRT
<213> ORGANISM: Artificial
<220> FEATURE:
<223> OTHER INFORMATION: Format 2b murine

<400> SEQUENCE: 88

Glu Pro Arg Gly Pro Thr Ile Lys Pro Ser Pro Ser Lys Ser Pro
1               5                   10                  15

Ala Pro Asn Leu Leu Gly Gly Pro Ser Val Phe Ile Phe Pro Pro Lys
            20                  25                  30

Ile Lys Asp Val Leu Met Ile Ser Leu Ser Pro Ile Val Thr Cys Val
        35                  40                  45

Val Val Asp Val Ser Glu Asp Asp Pro Asp Val Gln Ile Ser Trp Phe
    50                  55                  60

Val Asn Asn Val Glu Val His Thr Ala Gln Thr Gln Thr His Arg Glu
65                  70                  75                  80

Asp Tyr Asn Ser Thr Leu Arg Val Val Ser Ala Leu Pro Ile Gln His
                85                  90                  95

Gln Asp Trp Met Ser Gly Lys Glu Phe Lys Cys Lys Val Asn Asn Lys
            100                 105                 110

Asp Leu Pro Ala Pro Ile Glu Arg Thr Ile Ser Lys Pro Lys Gly Gly
        115                 120                 125

Gly Gly Ser Gly Gly Gly Ser Gly Gly Gly Ser Gly Gly Gly
    130                 135                 140

Gly Ser Gly Gly Gly Ser Ala Pro Asn Leu Leu Gly Gly Pro Ser
145                 150                 155                 160

Val Phe Ile Phe Pro Pro Lys Ile Lys Asp Val Leu Met Ile Ser Leu
                165                 170                 175

Ser Pro Ile Val Thr Cys Val Val Val Asp Val Ser Glu Asp Asp Pro
            180                 185                 190

Asp Val Gln Ile Ser Trp Phe Val Asn Asn Val Glu Val His Thr Ala
        195                 200                 205

Gln Thr Gln Thr His Arg Glu Asp Tyr Asn Ser Thr Leu Arg Val Val
    210                 215                 220

Ser Ala Leu Pro Ile Gln His Gln Asp Trp Met Ser Gly Lys Glu Phe
225                 230                 235                 240

Lys Cys Lys Val Asn Asn Lys Asp Leu Pro Ala Pro Ile Glu Arg Thr
            245                 250                 255

Ile Ser Lys Pro Lys Gly Ser Val Arg Ala Pro Gln Val Tyr Val Leu
        260                 265                 270

Pro Pro Pro Glu Glu Glu Met Thr Lys Lys Gln Val Thr Leu Thr Cys
    275                 280                 285

Met Val Thr Asp Phe Met Pro Glu Asp Ile Tyr Val Glu Trp Thr Asn
290                 295                 300

Asn Gly Lys Thr Glu Leu Asn Tyr Lys Asn Thr Glu Pro Val Leu Asp
305                 310                 315                 320

Ser Asp Gly Ser Tyr Phe Met Tyr Ser Lys Leu Arg Val Glu Lys Lys
                325                 330                 335

Asn Trp Val Glu Arg Asn Ser Tyr Ser Cys Ser Val Val His Glu Gly
            340                 345                 350

Leu His Asn His His Thr Thr Lys Ser Phe Ser Arg Thr Pro Gly Lys
        355                 360                 365

Gly Gly Gly Gly Ser Gly Gly Gly Gly Ser Gly Gly Gly Gly Ser Gly
    370                 375                 380

Gly Gly Ser Gly Gly Gly Ser Gly Ser Val Arg Ala Pro Gln
385                 390                 395                 400

Val Tyr Val Leu Pro Pro Pro Glu Glu Glu Met Thr Lys Lys Gln Val
                405                 410                 415

Thr Leu Thr Cys Met Val Thr Asp Phe Met Pro Glu Asp Ile Tyr Val
            420                 425                 430

Glu Trp Thr Asn Asn Gly Lys Thr Glu Leu Asn Tyr Lys Asn Thr Glu
        435                 440                 445

Pro Val Leu Asp Ser Asp Gly Ser Tyr Phe Met Tyr Ser Lys Leu Arg
    450                 455                 460

Val Glu Lys Lys Asn Trp Val Glu Arg Asn Ser Tyr Ser Cys Ser Val
465                 470                 475                 480

Val His Glu Gly Leu His Asn His His Thr Thr Lys Ser Phe Ser Arg
                485                 490                 495

Thr Pro Gly Lys
            500

<210> SEQ ID NO 89
<211> LENGTH: 506
<212> TYPE: PRT
<213> ORGANISM: Artificial
<220> FEATURE:
<223> OTHER INFORMATION: Format 2a murine

<400> SEQUENCE: 89

Glu Pro Arg Gly Pro Thr Ile Lys Pro Cys Pro Ala Pro Asn Leu Leu
1               5                   10                  15

Gly Gly Pro Ser Val Phe Ile Phe Pro Pro Lys Ile Lys Asp Val Leu
            20                  25                  30

Met Ile Ser Leu Ser Pro Ile Val Thr Cys Val Val Val Asp Val Ser
        35                  40                  45

Glu Asp Asp Pro Asp Val Gln Ile Ser Trp Phe Val Asn Asn Val Glu
    50                  55                  60

Val His Thr Ala Gln Thr Gln Thr His Arg Glu Asp Tyr Asn Ser Thr
65                  70                  75                  80

Leu Arg Val Val Ser Ala Leu Pro Ile Gln His Gln Asp Trp Met Ser
                85                  90                  95

-continued

```
Gly Lys Glu Phe Lys Cys Lys Val Asn Asn Lys Asp Leu Pro Ala Pro
                100                 105                 110
Ile Glu Arg Thr Ile Ser Lys Pro Lys Gly Gly Gly Ser Gly Gly
        115                 120                 125
Gly Gly Ser Gly Gly Gly Ser Gly Gly Gly Ser Gly Gly Gly
    130                 135                 140
Gly Ser Glu Pro Arg Gly Pro Thr Ile Lys Pro Cys Pro Ala Pro Asn
145                 150                 155                 160
Leu Leu Gly Gly Pro Ser Val Phe Ile Phe Pro Pro Lys Ile Lys Asp
                165                 170                 175
Val Leu Met Ile Ser Leu Ser Pro Ile Val Thr Cys Val Val Val Asp
                180                 185                 190
Val Ser Glu Asp Asp Pro Asp Val Gln Ile Ser Trp Phe Val Asn Asn
            195                 200                 205
Val Glu Val His Thr Ala Gln Thr Gln Thr His Arg Glu Asp Tyr Asn
            210                 215                 220
Ser Thr Leu Arg Val Val Ser Ala Leu Pro Ile Gln His Gln Asp Trp
225                 230                 235                 240
Met Ser Gly Lys Glu Phe Lys Cys Lys Val Asn Asn Lys Asp Leu Pro
                245                 250                 255
Ala Pro Ile Glu Arg Thr Ile Ser Lys Pro Lys Gly Ser Val Arg Ala
                260                 265                 270
Pro Gln Val Tyr Val Leu Pro Pro Glu Glu Met Thr Lys Lys
            275                 280                 285
Gln Val Thr Leu Thr Cys Met Val Thr Asp Phe Met Pro Glu Asp Ile
            290                 295                 300
Tyr Val Glu Trp Thr Asn Asn Gly Lys Thr Glu Leu Asn Tyr Lys Asn
305                 310                 315                 320
Thr Glu Pro Val Leu Asp Ser Asp Gly Ser Tyr Phe Met Tyr Ser Lys
                325                 330                 335
Leu Arg Val Glu Lys Lys Asn Trp Val Glu Arg Asn Ser Tyr Ser Cys
                340                 345                 350
Ser Val Val His Glu Gly Leu His Asn His His Thr Thr Lys Ser Phe
                355                 360                 365
Ser Arg Thr Pro Gly Lys Gly Gly Gly Ser Gly Gly Gly Gly Ser
    370                 375                 380
Gly Gly Gly Ser Gly Gly Gly Ser Gly Gly Gly Ser Gly
385                 390                 395                 400
Ser Val Arg Ala Pro Gln Val Tyr Val Leu Pro Pro Glu Glu
                405                 410                 415
Met Thr Lys Lys Gln Val Thr Leu Thr Cys Met Val Thr Asp Phe Met
                420                 425                 430
Pro Glu Asp Ile Tyr Val Glu Trp Thr Asn Asn Gly Lys Thr Glu Leu
            435                 440                 445
Asn Tyr Lys Asn Thr Glu Pro Val Leu Asp Ser Asp Gly Ser Tyr Phe
            450                 455                 460
Met Tyr Ser Lys Leu Arg Val Glu Lys Lys Asn Trp Val Glu Arg Asn
465                 470                 475                 480
Ser Tyr Ser Cys Ser Val Val His Glu Gly Leu His Asn His His Thr
                485                 490                 495
Thr Lys Ser Phe Ser Arg Thr Pro Gly Lys
                500                 505
```

```
<210> SEQ ID NO 90
<211> LENGTH: 507
<212> TYPE: PRT
<213> ORGANISM: Artificial
<220> FEATURE:
<223> OTHER INFORMATION: Format 1a murine

<400> SEQUENCE: 90

Glu Pro Arg Gly Pro Thr Ile Lys Pro Cys Pro Ala Pro Asn Leu Leu
1               5                   10                  15

Gly Gly Pro Ser Val Phe Ile Phe Pro Pro Lys Ile Lys Asp Val Leu
            20                  25                  30

Met Ile Ser Leu Ser Pro Ile Val Thr Cys Val Val Val Asp Val Ser
        35                  40                  45

Glu Asp Asp Pro Asp Val Gln Ile Ser Trp Phe Val Asn Asn Val Glu
    50                  55                  60

Val His Thr Ala Gln Thr Gln Thr His Arg Glu Asp Tyr Asn Ser Thr
65                  70                  75                  80

Leu Arg Val Val Ser Ala Leu Pro Ile Gln His Gln Asp Trp Met Ser
                85                  90                  95

Gly Lys Glu Phe Lys Cys Lys Val Asn Asn Lys Asp Leu Pro Ala Pro
            100                 105                 110

Ile Glu Arg Thr Ile Ser Lys Pro Lys Gly Ser Val Arg Ala Pro Gln
        115                 120                 125

Val Tyr Val Leu Pro Pro Pro Glu Glu Glu Met Thr Lys Lys Gln Val
    130                 135                 140

Thr Leu Thr Cys Met Val Thr Asp Phe Met Pro Glu Asp Ile Tyr Val
145                 150                 155                 160

Glu Trp Thr Asn Asn Gly Lys Thr Glu Leu Asn Tyr Lys Asn Thr Glu
                165                 170                 175

Pro Val Leu Asp Ser Asp Gly Ser Tyr Phe Met Tyr Ser Lys Leu Arg
            180                 185                 190

Val Glu Lys Lys Asn Trp Val Glu Arg Asn Ser Tyr Ser Cys Ser Val
        195                 200                 205

Val His Glu Gly Leu His Asn His His Thr Thr Lys Ser Phe Ser Arg
    210                 215                 220

Thr Pro Gly Lys Gly Gly Ser Ser Thr Ala Ser Gly Ser Gly Ser Gly
225                 230                 235                 240

Gly Ser Gly Thr Ala Gly Ser Ser Gly Gly Ala Gly Ser Ser Gly Gly
                245                 250                 255

Ser Thr Thr Ala Gly Gly Ser Ala Ser Gly Ser Gly Thr Gly Ser
            260                 265                 270

Gly Thr Gly Gly Ala Ser Ser Gly Gly Ala Ser Gly Ala Ser Gly Pro
        275                 280                 285

Cys Pro Ala Pro Asn Leu Leu Gly Gly Pro Ser Val Phe Ile Phe Pro
    290                 295                 300

Pro Lys Ile Lys Asp Val Leu Met Ile Ser Leu Ser Pro Ile Val Thr
305                 310                 315                 320

Cys Val Val Val Asp Val Ser Glu Asp Asp Pro Asp Val Gln Ile Ser
                325                 330                 335

Trp Phe Val Asn Asn Val Glu Val His Thr Ala Gln Thr Gln Thr His
            340                 345                 350

Arg Glu Asp Tyr Asn Ser Thr Leu Arg Val Val Ser Ala Leu Pro Ile
        355                 360                 365

Gln His Gln Asp Trp Met Ser Gly Lys Glu Phe Lys Cys Lys Val Asn
```

```
            370                 375                 380
Asn Lys Asp Leu Pro Ala Pro Ile Glu Arg Thr Ile Ser Lys Pro Lys
385                 390                 395                 400

Gly Ser Val Arg Ala Pro Gln Val Tyr Val Leu Pro Pro Glu Glu
                405                 410                 415

Glu Met Thr Lys Lys Gln Val Thr Leu Thr Cys Met Val Thr Asp Phe
                420                 425                 430

Met Pro Glu Asp Ile Tyr Val Glu Trp Thr Asn Asn Gly Lys Thr Glu
                435                 440                 445

Leu Asn Tyr Lys Asn Thr Glu Pro Val Leu Asp Ser Asp Gly Ser Tyr
            450                 455                 460

Phe Met Tyr Ser Lys Leu Arg Val Glu Lys Lys Asn Trp Val Glu Arg
465                 470                 475                 480

Asn Ser Tyr Ser Cys Ser Val Val His Glu Gly Leu His Asn His His
                485                 490                 495

Thr Thr Lys Ser Phe Ser Arg Thr Pro Gly Lys
                500                 505

<210> SEQ ID NO 91
<211> LENGTH: 641
<212> TYPE: PRT
<213> ORGANISM: Artificial
<220> FEATURE:
<223> OTHER INFORMATION: gp130 domain 1 fusion

<400> SEQUENCE: 91

Lys Leu Ala Thr Met Ser Val Pro Thr Gln Val Leu Gly Leu Leu
1               5                   10                  15

Leu Trp Leu Thr Asp Ala Arg Cys Glu Leu Leu Asp Pro Cys Gly Tyr
                20                  25                  30

Ile Ser Pro Glu Ser Pro Val Val Gln Leu His Ser Asn Phe Thr Ala
            35                  40                  45

Val Cys Val Leu Lys Glu Lys Cys Met Asp Tyr Phe His Val Asn Ala
        50                  55                  60

Asn Tyr Ile Val Trp Lys Thr Asn His Phe Thr Ile Pro Lys Glu Gln
65                  70                  75                  80

Tyr Thr Ile Ile Asn Arg Thr Ala Ser Ser Val Thr Phe Thr Asp Ile
                85                  90                  95

Ala Ser Leu Asn Ile Gln Leu Thr Cys Asn Ile Leu Thr Phe Gly Gln
            100                 105                 110

Leu Glu Gln Asn Val Tyr Gly Ile Thr Ile Ile Ser Gly Ser Ser Ala
        115                 120                 125

Val Pro Arg Asp Gly Gly Ser Lys Pro Gly Ile Cys Thr Val Pro Glu
    130                 135                 140

Val Ser Ser Val Phe Ile Phe Pro Pro Lys Pro Lys Asp Val Leu Thr
145                 150                 155                 160

Ile Thr Leu Thr Pro Lys Val Thr Cys Val Val Asp Ile Ser Lys
                165                 170                 175

Asp Asp Pro Glu Val Gln Phe Ser Trp Phe Val Asp Asp Val Glu Val
            180                 185                 190

His Thr Ala Gln Thr Gln Pro Arg Glu Glu Gln Phe Asn Ser Thr Phe
        195                 200                 205

Arg Ser Val Ser Glu Leu Pro Ile Met His Gln Asp Trp Leu Asn Gly
    210                 215                 220

Lys Glu Phe Lys Cys Arg Val Asn Ser Ala Ala Phe Pro Ala Pro Ile
```

```
                225                 230                 235                 240
        Glu Lys Thr Ile Ser Lys Thr Lys Gly Arg Pro Lys Ala Pro Gln Val
                        245                 250                 255
        Tyr Thr Ile Pro Pro Lys Glu Gln Met Ala Lys Asp Lys Val Ser
                        260                 265                 270
        Leu Thr Cys Met Ile Thr Asp Phe Phe Pro Glu Asp Ile Thr Val Glu
                    275                 280                 285
        Trp Gln Trp Asn Gly Gln Pro Ala Glu Asn Tyr Lys Asn Thr Gln Pro
                    290                 295                 300
        Ile Met Asp Thr Asp Gly Ser Tyr Phe Val Tyr Ser Lys Leu Asn Val
        305                 310                 315                 320
        Gln Lys Ser Asn Trp Glu Ala Gly Asn Thr Phe Thr Cys Ser Val Leu
                        325                 330                 335
        His Glu Gly Leu His Asn His His Thr Glu Lys Ser Leu Ser His Ser
                    340                 345                 350
        Pro Gly Lys Gly Gly Ser Ser Thr Ala Ser Gly Ser Gly Ser Gly Gly
                    355                 360                 365
        Ser Gly Thr Ala Gly Ser Ser Gly Gly Ala Gly Ser Ser Gly Gly Ser
            370                 375                 380
        Thr Thr Ala Gly Gly Ser Ala Ser Gly Ser Gly Ser Thr Gly Ser Gly
        385                 390                 395                 400
        Thr Gly Gly Ala Ser Ser Gly Gly Ala Ser Gly Ala Ser Gly Val Pro
                        405                 410                 415
        Arg Asp Gly Gly Ser Lys Pro Gly Ile Cys Thr Val Pro Glu Val Ser
                        420                 425                 430
        Ser Val Phe Ile Phe Pro Pro Lys Pro Lys Asp Val Leu Thr Ile Thr
                    435                 440                 445
        Leu Thr Pro Lys Val Thr Cys Val Val Val Asp Ile Ser Lys Asp Asp
                450                 455                 460
        Pro Glu Val Gln Phe Ser Trp Phe Val Asp Asp Val Glu Val His Thr
        465                 470                 475                 480
        Ala Gln Thr Gln Pro Arg Glu Glu Gln Phe Asn Ser Thr Phe Arg Ser
                        485                 490                 495
        Val Ser Glu Leu Pro Ile Met His Gln Asp Trp Leu Asn Gly Lys Glu
                    500                 505                 510
        Phe Lys Cys Arg Val Asn Ser Ala Ala Phe Pro Ala Pro Ile Glu Lys
                    515                 520                 525
        Thr Ile Ser Lys Thr Lys Gly Arg Pro Lys Ala Pro Gln Val Tyr Thr
                    530                 535                 540
        Ile Pro Pro Lys Glu Gln Met Ala Lys Asp Lys Val Ser Leu Thr
        545                 550                 555                 560
        Cys Met Ile Thr Asp Phe Phe Pro Glu Asp Ile Thr Val Glu Trp Gln
                        565                 570                 575
        Trp Asn Gly Gln Pro Ala Glu Asn Tyr Lys Asn Thr Gln Pro Ile Met
                    580                 585                 590
        Asp Thr Asp Gly Ser Tyr Phe Val Tyr Ser Lys Leu Asn Val Gln Lys
                    595                 600                 605
        Ser Asn Trp Glu Ala Gly Asn Thr Phe Thr Cys Ser Val Leu His Glu
                    610                 615                 620
        Gly Leu His Asn His His Thr Glu Lys Ser Leu Ser His Ser Pro Gly
        625                 630                 635                 640

Lys
```

```
<210> SEQ ID NO 92
<211> LENGTH: 5
<212> TYPE: PRT
<213> ORGANISM: Artificial Sequence
<220> FEATURE:
<223> OTHER INFORMATION: Synthetic

<400> SEQUENCE: 92

Gly Ser Gly Gly Ser
1               5

<210> SEQ ID NO 93
<211> LENGTH: 5
<212> TYPE: PRT
<213> ORGANISM: Artificial Sequence
<220> FEATURE:
<223> OTHER INFORMATION: synthetic

<400> SEQUENCE: 93

Gly Gly Gly Gly Ser
1               5

<210> SEQ ID NO 94
<211> LENGTH: 4
<212> TYPE: PRT
<213> ORGANISM: Artificial Sequence
<220> FEATURE:
<223> OTHER INFORMATION: synthetic

<400> SEQUENCE: 94

Gly Gly Gly Ser
1
```